(12) United States Patent
Shah

(10) Patent No.: US 9,428,565 B2
(45) Date of Patent: Aug. 30, 2016

(54) TREATMENT AND BIOLUMINESCENT VISUALIZATION USING MULTIMODAL TRAIL MOLECULES

(75) Inventor: Khalid Shah, Andover, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/982,343

(22) PCT Filed: Jan. 31, 2012

(86) PCT No.: PCT/US2012/023221
§ 371 (c)(1),
(2), (4) Date: Oct. 24, 2013

(87) PCT Pub. No.: WO2012/106281
PCT Pub. Date: Aug. 9, 2012

(65) Prior Publication Data
US 2014/0086907 A1    Mar. 27, 2014

Related U.S. Application Data

(60) Provisional application No. 61/437,843, filed on Jan. 31, 2011.

(51) Int. Cl.
| C07K 14/00 | (2006.01) |
| A61K 38/02 | (2006.01) |
| A61K 45/00 | (2006.01) |
| C07K 14/47 | (2006.01) |
| A61K 38/17 | (2006.01) |
| A61K 35/28 | (2015.01) |
| A61K 35/30 | (2015.01) |
| A61K 39/395 | (2006.01) |
| A61K 45/06 | (2006.01) |

(52) U.S. Cl.
CPC ........... *C07K 14/4747* (2013.01); *A61K 35/28* (2013.01); *A61K 35/30* (2013.01); *A61K 38/1761* (2013.01); *A61K 38/1774* (2013.01); *A61K 39/3955* (2013.01); *A61K 45/06* (2013.01); *A01K 2207/12* (2013.01); *C07K 2319/55* (2013.01); *C07K 2319/61* (2013.01); *C12N 2740/15043* (2013.01)

(58) Field of Classification Search
None
See application file for complete search history.

(56) References Cited

U.S. PATENT DOCUMENTS

| 5,037,743 | A | 8/1991 | Welch et al. |
| 5,143,830 | A | 9/1992 | Holland et al. |
| 5,288,641 | A | 2/1994 | Roizman |
| 6,284,236 | B1 * | 9/2001 | Wiley et al. ........... 424/85.1 |
| 6,444,640 | B1 * | 9/2002 | Nagane et al. ........... 514/19.3 |
| 6,998,116 | B1 * | 2/2006 | Ashkenazi ........... 424/85.1 |
| 7,052,834 | B1 * | 5/2006 | Kidd et al. ........... 435/6.14 |
| 7,063,835 | B2 | 6/2006 | Coffin |
| 7,790,451 | B2 | 9/2010 | Yazaki et al. |
| 8,216,819 | B2 | 7/2012 | Hermiston et al. |
| 8,222,036 | B2 | 7/2012 | Thompson et al. |
| 8,236,941 | B2 | 8/2012 | Yao |
| 2002/0128438 | A1 | 9/2002 | Seol et al. |
| 2004/0120928 | A1 | 6/2004 | Frenkel |
| 2005/0214266 | A1 | 9/2005 | Morris et al. |
| 2009/0155247 | A1 | 6/2009 | Ashkenazi |
| 2009/0175826 | A1 | 7/2009 | Subbiah |
| 2009/0325867 | A1 | 12/2009 | Cohen et al. |
| 2010/0240097 | A1 | 9/2010 | Young et al. |
| 2010/0272686 | A1 | 10/2010 | Kaur et al. |
| 2010/0305002 | A1 | 12/2010 | Chenchik et al. |
| 2010/0311948 | A1 * | 12/2010 | Hua et al. ........... 530/351 |
| 2010/0323399 | A1 | 12/2010 | Wiley et al. |
| 2011/0014656 | A1 | 1/2011 | Levin et al. |
| 2011/0177032 | A1 | 7/2011 | Martuza et al. |

FOREIGN PATENT DOCUMENTS

| WO | WO02/22175 | * | 3/2002 | ........... A61K 48/00 |
| WO | 2004/087930 A2 | | 10/2004 | |
| WO | 2005/000220 A2 | | 1/2005 | |
| WO | 2009/028870 A2 | | 3/2009 | |
| WO | 2009/029601 A2 | | 3/2009 | |
| WO | 2009/148488 A2 | | 12/2009 | |
| WO | 2012/106281 A2 | | 1/2012 | |
| WO | 2012/072815 A1 | | 6/2012 | |

OTHER PUBLICATIONS

An et al., Drug Interactions between the Proteasome Inhibitor Bortezomib and Cytotoxic Chemotherapy, Tumor Necrosis Factor (TNF) α, and TNFRelated Apoptosis-Inducing Ligand in Prostate Cancer. Clin.Ca. Res. 9, 4537-4545, 2003.*
LeBlanc et al., Apo2L/TRAIL and its death and decoy receptors. Cell Death and Diff. 10, 66-75, 2003.*
Lubkowsky et al. (The structural basis of phage display elucidated by the crystal structure of the N-terminal domains of g3p. Nature Struct.Biol. 5, 140-147, 1998.*
Hingtgen et al., Stem Cells, 28:832-841 (2010). "A Novel Molecule Integrating Therapeutic and Diagnostic Activities Reveals Multiple Aspects of Stem Cell-Based Therapy."
1. Ashkenazi A. et al., J Clin Oncol 2008; 26: 3621-30.
2. Baci-Onder, T., Wakimoto, H., Cameron, C. and Shah, K. Evaluating the efficacy of a dual PI3K/mTOR inhibitor and stem cell delivered TRAIL in mouse models of glioma. Cancer Research (2010 in press).
Bremer E, et al., Cancer Res 2005; 65: 3380-88.
Bremer E, et al., J Biol Chem 2005; 280: 10025-33.

(Continued)

*Primary Examiner* — Elly-Gerald Stoica
(74) *Attorney, Agent, or Firm* — Nixon Peabody LLP; David S. Resnick; Mark J. FitzGerald

(57) ABSTRACT

Described herein are novel compositions comprising multimodal TRAIL agents and cells engineered to express such multimodal TRAIL agents, including cells encapsulated in a scaffold or matrix, for use in the treatment of disorders such as cancer.

13 Claims, 15 Drawing Sheets

(56) References Cited

OTHER PUBLICATIONS

Bremer E, Samplonius D, Kroesen BJ et al. Exceptionally potent anti-tumor bystander activity of an scFv:sTRAIL fusion protein with specificity for EGP2 toward target antigen-negative tumor cells. Neoplasia 2004; 6: 636-645.
Bremer E. et al., J Mol Med 2008; 86: 909-24.
Compte et al., Stem Cells. 2009 "Tumor immunotherapy using gene-modified human mesenchymal stem cells loaded into synthetic extracellular matrix scaffolds" Mar;27(3):753-60.
Ehtesham, M. et al. Induction of glioblastoma apoptosis using neural stem cell-mediated delivery of tumor necrosis factor-related apoptosis-inducing ligand. Cancer Res 62,7170-4 (2002).
Hingtgen et al., Mol Cancer Ther. "Targeting multiple pathways in gliomas with stem cell and viral delivered S-TRAIL and Temozolomide" Nov. 2008;7(11):3575-85.
Hingtgen S, et al. A novel molecule integrating therapeutic and diagnostic activities reveals multiple aspects of stem cell-based therapy. Stem Cells 2010, 28: 832-841.
Kauer TM et al. Encapsulated therapeutic stem cells implanted in the tumor resection cavity induce cell death in gliomas, Nat Neurosci. Dec. 25, 2011; 15(2): 197-204.
Kelley SK, Harris LA, Xie D et al. Preclinical studies to predict the disposition of Apo2L/tumor necrosis factor-related apoptosis-inducing ligand in humans: Characterization of in vivo efficacy, pharmacokinetics, and safety. J Pharmacol Exp Ther 2001; 299: 31-38.
Kirshner et al., Journal of Virology, "Identification of TRAIL as an interferon regulatory factor 3 transcriptional target" 79 (14):9320-9324 (2005).
Kock N, Kasmieh R, Weissleder R, Shah K. Tumor therapy mediated by lentiviral expression of shBcl-2 and S-TRAIL. Neoplasia. 2007;9:435-442.
Kuijlen et al., Neuropathology and Applied Neurobiology, 36(3):168-182 (2010).
Sasportas LS et al., Proc Natl Acad Sci U S A 2009; 106: 4822-7.
Shah et al., Ann Neurol. "Glioma therapy and real-time imaging of neural precursor cell migration and tumor regression" Jan. 2005;57(1):34-41.
Shah K, Hingtgen S, Kasmieh R, et al. Bimodal viral vectors and in vivo imaging reveal the fate of human neural stem cells in experimental glioma model. J Neurosci. 2008;28:4406-4413.
Shah K, Tung CH, Yang K, Weissleder R, Breakefield XO. Inducible release of TRAIL fusion proteins from a proapoptotic form for tumor therapy. Cancer Res. 2004;64:3236-3242.
Shah, K. Tang, Y. Breakefield, X. & Weissleder, R. Real-time imaging of TRAIL-induced apoptosis of glioma tumors in vivo. Oncogene 22,6865-72 (2003).
Shah et al., Molecular Therapy, "In vivo imaging of S-TRAIL-mediated tumor regression and apoptosis" 11 (6) :926-931 (2005).
Shen J, Wu Y, Shi L et al. "Construction and characterization of two versions of bifunctional EGFP-sTRAIL fusion proteins" Appl Microbiol Biotechnol 2007; 76: 141-149.
Stieglmaier J, et al., Cancer Immunol Immunother 2008; 57: 233-46.
Badran et al., "Target cell-restricted apoptosis induction by 528scFv-TRAIL fusion protein specific for human EGFR and expressed in *Escherichia coli*," International Journal of Oncology, 36(5):1229-1234 (2010).
Aghi et al., "Oncolytic viral therapies—the clinical experience", Oncogene, 24: 7802-7816 (2005).
Allan et al., "Inhibition of caspase-9 through phosphorylation at Thr 125 by ERK MAPK", Nat Cell Biol 5(7): 647-654.
Barash et al., "Human secretory signal peptide description by hidden Markov model and generation of a strong artificial signal peptide for secreted protein expression", Biochemical and Biophysical Research Communications 294: 835-842 (2002).
Breitbach et al., "Intravenous delivery of a multi-mechanistic cancer-targeted oncolytic poxvirus in humans", Nature 477: 99-102 (2011).

Bremer et al., "Portent Systemic Anticancer Activity of Adenovirally Expressed EGFR-Selective TRAIL Fusion Protein", Molecular Therapy, 16(12): 1919-1926 (2008).
Choo et al., "SPdb—a signal peptide database", BMC Bioinformatics, 6: 249 (2005).
Corsten et al., "MicroRNA-21 Knockdown Disrupts Glioma Growth in vivo and Displays Synergistic Cytotoxicity with Neural Precursor Cell-Delivered S-TRAIL in Human Gliomas", Cancer Res, 67(19): 8994-9000 (2007).
Corsten et al., "Therapeutic stem-cells for cancer treatment: hopes and hurdles in tactical warfare", Lancet Oncol, 9: 376-384 (2008).
Erhardt et al., "B-Raf inhibits programmed cell death downstream of cytochrome c release from mitochondria by activating the MEK/Erk pathway", Mol Cell Biol, 19:5308-5315 (1999).
Fukuhara et al., "Triple gene-deleted oncolytic herpes simplex virus vector double-armed with interleukin 18 and soluble B7-1 constructed by bacterial artificial chromosome-mediated system", Cancer Res, 65:10663-10668b(2005).
Han et al., "Development of a second-generation oncolytic Herpes simplex virus expressing Tnf alpha for cancer therapy", J Gene Med, 9:99-106 (2007).
Hoffmann et al. "Comparison of herpes simplex virus- and conditionally replicative adenovirus-based vectors for glioblastoma treatment", Cancer Gene Ther, 14:627-639 (2007).
Holmstrom et al., "MAPK/ERK signaling in activated T cells inhibits CD95/Fas-mediated apoptosis downstream of DISC assembly", Embo J 19:5418-5428 (2000).
Jacobson et al., "Programmed cell death in animal development", Cell 88:347-354 (1997).
Johnstone et al., "The TRAIL apoptotic pathway in cancer onset, progression and therapy", Nat Rev Cancer 8(10): 782-798 (2008).
Kanai et al., "A Novel Oncolytic Herpes 1-15 Simplex Virus that Synergizes with Phosphoinositide 3-kinase/Akt Pathway Inhibitors to Target Glioblastoma Stem Cells", Clinical Cancer Research, 17(11):3686-3696 (2011).
Kirn et al., "Replication-selective virotherapy for cancer: Biological principles, risk management and future directions", Nat Med 7(7):781-787 (2001).
Kuroda et al., "Flip-Flop HSV-BAC: bacterial artificial chromosome based system for rapid generation of recombinant herpes simplex virus vectors using two independent site-specific recombinases", BMC Biotechnol 6:40 (2006).
Kurozumi et al., "Effect of tumor microenvironment modulation on the efficacy of oncolytic virus therapy", J Natl Cancer Inst 99(23):1768-1781 (2007).
Leopardi et al., "The herpes simplex virus major regulatory protein ICP4 blocks apoptosis induced by the virus or by hyperthermia", PNAS 93(18):9583-9587 (1996).
Leopardi et al., "The herpes simplex virus 1 protein kinase US3 is required for protection from apoptosis induced by the virus" PNAS 94(15):7891-7896 (1997).
Liu et al., "Clinical trial results with oncolytic virotherapy: a century of promise, a decade of progress", Nat Clin Pract Oncol 4(2):101-117 (2007).
Markert et al., "Conditionally replicating herpes simplex virus mutant G207 for the treatment of malingnt glioma: results of a phase I trial", Gene Ther 7(10):867-874 (2000).
Markert et al., "Phase lb trial of mutant herpes simplex virus G207 inoculated pre-and post-tumor resection for recurrent GBM", Mol Ther 1791):199-207 (2009).
Markert et al., "High diagnostic value of morphologic examination and molecular analysis of bone marrow biopsies in a case of BCR-ABL+ CML with clusters of blasts", Int J Hematol 89(3):294-297 (2009).
Martinelli et al., "Anti-epidermal growth factor receptor monoclonal antibodies in cancer therapy", Clinical and experimental immunology, 158:1-9 (2009).
Mineta et al., "Attenuated multi-mutated herpes simplex virus-1 for the treatment of malignant gliomas", Nat Med 1 (9):938-943 (1995).
Miyatake et al., "Transcriptional targeting of herpes simplex virus for cell-specific replication", J Virol. 1 (7):5124-5132 (1997).

(56) References Cited

OTHER PUBLICATIONS

Oliveira et al., "Downregulation of EGFR by a novel multivalent nanobody-liposome platform", Journal of Controlled Release 14:165-175 (2010).
Pan et al., "Synergistic induction of tumor cell death by combining cisplatin with an oncolytic adenovirus carrying TRAIL", Mol Cell Biochem 304:315-323 (2007).
Parato et al., "Recent progress in the battle between oncolytic viruses and tumors", Nat Rev Cancer 5:965-976 (2005).
Rieger et al., "Mechanisms of resistance of human glioma cells to Apo2 ligand/TNF-related apoptosis-inducing ligand", Cell Physiol Biochem 20:23-34 (2007).
Roovers et lal., "Efficient inhibition of EGFR signalling and of tumor growth by antagonistic anti EGFR nanobodies", Cancer Immunol Immunother 56:303-317 (2007).
Rozanov et al., "Engineering a leucine zipper-TRAIL homotrimer with improved cytotoxicity in tumor cells", Mol Cancer Ther. 8(6):1515-1525 (2009).
Saeki et al.,"Herpes simplex virus type 1 DNA amplified as bacterial artificial chromosome in *Escherichia coli*: rescue of replication-competent virus progeny and packaging of amplicon vectors", Human Gene Therapy, 9:2787-2794 (1998).
Smith et al., "The TNF receptor superfamily of cellular and viral proteins: Activation, Constimulation, and Death", 76:959-062 (1994).
Sprenger et al., "LOCATE: a mammalian protein subcellular localization database", Nucleic Acids Research, 36D230-D233 (2008).
Stern et al., "Improving mammalian cell factories: The selection of signal peptide has a major impact on recombinant protein synthesis and secretion in mammalian cells", Cell and Molecular Biology, 2:1-17 (2007).
Tamura et al., "Multimechanistic tumor targeted oncolytic virus overcomes resistance in brain tumor", The American Society of Gene and Cell Therapy, 21(1):68-77 (2013).
Tashker et al., "Post-cytochrome C protection from apoptosis conferred by a MAPK pathway in Xenopus egg extracts", Mol Biol Cell 13:393-401 (2002).
Todo et al., "Oncolytic herpes simplex virus vector with enhanced MHC class I presentation and tumor cell killing" PNAS 98(11):6396-6401 (2001).
Todo et al., "Armed" oncolytic herpes simplex viruses for brain tumor therapy, Cell Adh Migr 2(3):208-213 (2008).
Varghese et al., "Oncolytic herpes simplex virus vectors for cancer virotherapy", Cancer Gene Ther 9:967-978 (2002).
Wakimoto et al., "Human glioblastoma-derived cancer stem cells: establishment of invasive glioma models and treatment with oncolytic herpes simplex virus vectors", Cancer Res 69(8):3472-3481 (2009).
Wang et al., "In Vitro efficacy of Immuno-Chemotherapy with Anti-EGFR human fab-taxol conjugate A431 epidermoid carcinoma cells", Cancer Biology & Therapy, 6(6):980-987 (2007).
Wen et al., "Malignant gliomas in adults", N Engl J Med 359(5):492-507 (2008).
Wierzorek et al., "Death receptor agonists as a targeted therapy for cancer", Clin Cancer Res 16(6):1701-1708 (2010).
Wohlfahrt et al., "A capsid-modified, conditionally replicating oncolytic adenovirus vector expressing TRAIL Leads to enhanced cancer cell killing in human glioblastoma models", Cancer Res 67(8):8783-8790 (2007).
Xia et al., "Opposing effects of ERK and JNK-p38 MAP kinases on apoptosis", Science 270.5240:1326-1331 (1995).
Yamamoto et al., "Imaging immediate-early and strict-late promoter activity during oncolytic herpes simplex virus type 1 infection and replication in tumors", Gene Therapy 13:731-1736 (2006).
Yip et al., "Stem-cell based therapies for brain tumors", Curr Opin Mol Ther 10(4):334-342 (2008).

* cited by examiner

Figures 6A-6D
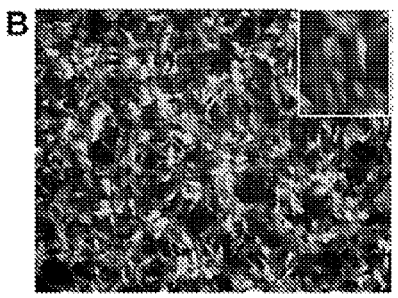
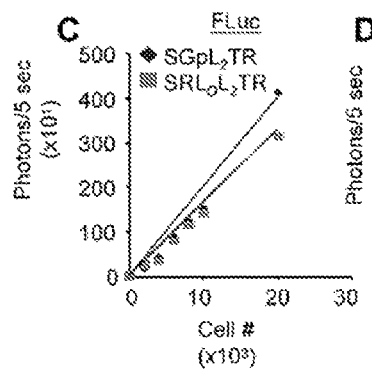
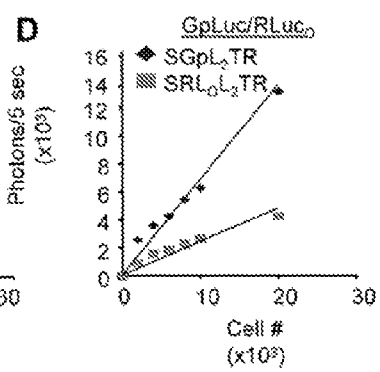
Figures 7A-7D
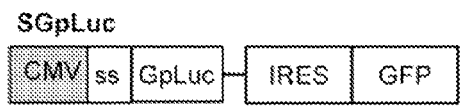
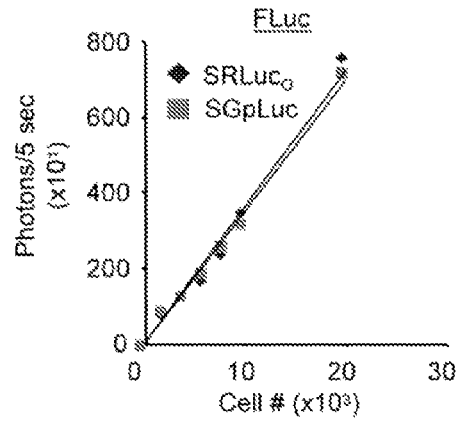
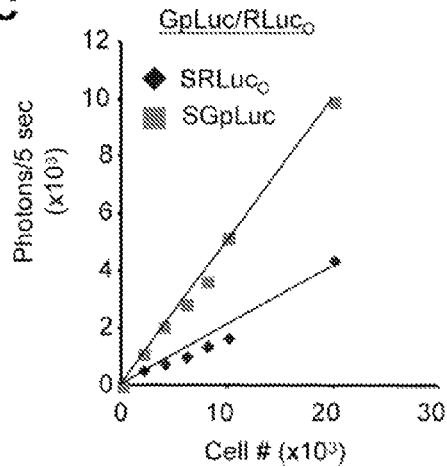
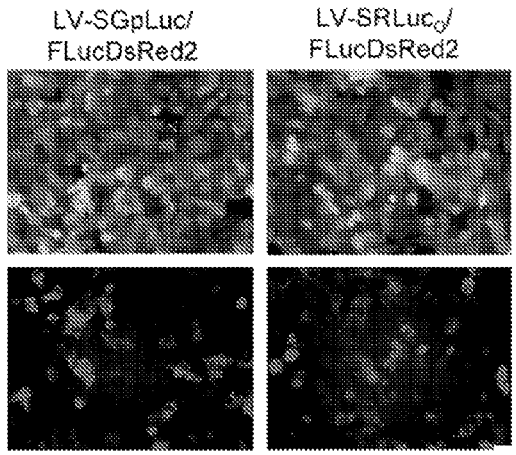

SEQUENCE LISTING

<160> NUMBER OF SEQ ID NOS: 4

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Gly Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 2
<211> LENGTH: 232
<212> TYPE: PRT
<213> ORGANISM: Mus musculus

<400> SEQUENCE: 2

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu

```
                    35                  40                  45
Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Leu Leu Leu
            180                 185                 190

Leu Leu Leu Leu Leu Pro Leu Thr Leu Val Leu Leu Ala Ala Ala
        195                 200                 205

Trp Gly Leu Arg Trp Gln Arg Ala Arg Arg Arg Gly Glu Leu His Pro
    210                 215                 220

Gly Val Pro Leu Pro Ser His Pro
225                 230

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ala Ser Gly Gly Pro Glu
1               5

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ser Thr Gly Gly Ser Gly Lys Pro Gly Ser Gly Glu Gly Ser Thr
1               5                   10                  15

Gly Gly
```

TREATMENT AND BIOLUMINESCENT VISUALIZATION USING MULTIMODAL TRAIL MOLECULES

CROSS-REFERENCE TO RELATED APPLICATIONS

This application is a 35 U.S.C. §371 National Phase Entry Application of International Application No. PCT/US2012/023221 filed Jan. 31, 2012, which designates the U.S., and which claims benefit under 35 U.S.C. §119(e) of U.S. Provisional Patent Application Ser. No. 61/437,843 filed on Jan. 31, 2011, the contents of which are incorporated herein by reference in their entireties.

GOVERNMENT SUPPORT

This invention was made with Government support under R21CA131980 awarded by the National Institutes of Health (NIH). The Government has certain rights in the invention.

SEQUENCE LISTING

The instant application contains a Sequence Listing which has been submitted electronically in ASCII format and is hereby incorporated by reference in its entirety. Said ASCII copy, created on Oct. 31, 2013, is named 030258-069242-US_SL.txt and is 5,339 bytes in size.

FIELD OF THE INVENTION

The field of the invention relates to multimodal TRAIL molecules and cells engineered to express multimodal therapeutic agents, such as TRAIL, for use in cellular therapies.

BACKGROUND

Cancer remains one of the most deadly threats to human health. In the U.S., cancer affects nearly 1.3 million new patients each year, and is the second leading cause of death after heart disease, accounting for approximately 1 in 4 deaths. It is also predicted that cancer may surpass cardiovascular diseases as the number one cause of death within the next decade. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making timely detection and treatment extremely difficult.

Glioblastoma (GBM) is the most frequent and aggressive type of tumor to develop from neuroepithelial tissue. GBMs are very heterogeneous with multiple clones that contain varied genetic imbalances within one tumour, making it very difficult to treat successfully. Even with improved surgical techniques and post-operative radiotherapy, the mean overall survival time of patients with GBM after neurosurgical debulking and radiotherapy is still limited to approximately 12 months. Currently, most chemotherapeutic agents have minimal effects on patient survival (J. M. A. Kuijlen et al., Neuropathology and Applied Neurobiology, 2010 Vol. 36 (3), pp. 168-182).

SUMMARY OF THE INVENTION

The compositions and methods comprising multimodal TRAIL agents described herein provide novel therapeutic approaches for treatment of cancers, such as glioblastoma. Shown herein is the development of novel multifunctional, multimodal TRAIL agents as molecules that have both diagnostic (in vivo tracking via, for example, optical reporters) and therapeutic (anti-tumor via a cytotoxic agent, e.g., TRAIL) properties. Further, their application in characterizing therapeutic delivery by engineered stem cells is demonstrated. These novel multimodal TRAIL agents are easily optically visualized for serial monitoring of cell-based pharmacokinetics, while retaining potent anti-tumor functions. Optical imaging permits elucidation of differences in pharmacokinetics, tissues distribution, and therapeutic efficacy of the multimodal TRAIL agents delivered to tumors by engineered stem cells or via i.v. injection. Further, visualization of therapeutic levels of the multimodal TRAIL agents in real-time demonstrated for the first time that a single administration of engineered neural stem cells expressing a multimodal TRAIL agent provides continuous sustained and localized delivery of the multimodal TRAIL agent that attenuates tumor growth, whereas a single i.v. infusion or direct administration of media containing the multimodal TRAIL agent results in widespread off-target binding and significantly shortened delivery window that correlates with minimal anti-tumor effects.

Demonstrated herein are new approaches to treatment of tumors, such as GBM, using therapeutic stem cells encapsulated in biodegradable, synthetic extracellular matrix (sECM), using, for example, mouse models of human GBM resection. Using multimodal imaging, quantitative surgical debulking of human GBM tumors in mice that resulted in increased survival is demonstrated. Next, as shown herein, sECM encapsulation of engineered stem cells increased their retention in the tumor resection cavity, permitted tumor-selective migration, and release of diagnostic and therapeutic proteins in vivo. Simulating the clinical scenario of GBM treatment, the release of tumor-selective S-TRAIL (secretable tumor necrosis factor apoptosis inducing ligand) from sECM-encapsulated stem cells in the resection cavity eradicated residual tumor cells by inducing caspase-mediated apoptosis, delayed tumor regrowth, and significantly increased survival of mice. The studies described herein demonstrate the efficacy and utility of encapsulated therapeutic stem cells in the treatment of cancers, such as GBM resection.

Accordingly, provided herein, in some aspects, are multimodal TRAIL agents comprising a reporter module and a therapeutic TRAIL module, where the therapeutic TRAIL module comprises an extracellular domain of human TRAIL.

In some embodiments of these aspects and all such aspects described herein, the extracellular domain of human TRAIL comprises amino acids 114-281 of SEQ ID NO: 1.

In some embodiments of these aspects and all such aspects described herein, the multimodal TRAIL agent further comprises a signal sequence. In some such embodiments, the signal sequence comprises SEQ ID NO: 2.

In some embodiments of these aspects and all such aspects described herein, the therapeutic TRAIL module further comprises an isoleucine zipper domain.

In some embodiments of these aspects and all such aspects described herein, the multimodal TRAIL agent further comprises a linker domain C-terminal to the reporter module and N-terminal to the therapeutic TRAIL module. In some such embodiments, the linker domain comprises at least eight amino acids. In some embodiments, the linker domain comprises the amino acid sequence of SEQ ID NO: 4.

In another aspect, provided herein, are pharmaceutical compositions comprising any of the multimodal TRAIL agents described herein comprising a reporter module and a therapeutic TRAIL module, where the therapeutic TRAIL module comprises an extracellular domain of human TRAIL, and a pharmaceutically acceptable carrier.

In some aspects, provided herein are vectors comprising a nucleic acid sequence encoding any of the multimodal TRAIL agents comprising a reporter module and a therapeutic TRAIL module described herein, where the therapeutic TRAIL module comprises an extracellular domain of human TRAIL, or one or more modules thereof, described herein. In some embodiments of these aspects and all such aspects described herein, the vector is a lentiviral vector or an adenoviral vector.

Also provided herein, in some aspects, are cells comprising a nucleic acid sequence encoding any of the multimodal TRAIL agents comprising a reporter module and a therapeutic TRAIL module described herein, where the therapeutic TRAIL module comprises an extracellular domain of human TRAIL. In other aspects, provided herein are cells comprising any of the vectors comprising a nucleic acid sequence encoding any of the multimodal TRAIL agents, or one or more modules thereof, described herein. In some embodiments of these aspects and all such aspects described herein, the cell is a stem cell. In some such embodiments, the stem cell is a neural stem cell or a mesenchymal stem cell. In some embodiments of these aspects and all such aspects described herein, the cell is encapsulated in a matrix or scaffold. In some embodiments, the matrix comprises a synthetic extracellular matrix. In some embodiments, the matrix is biodegradeable. In some embodiments, the synthetic extracellular matrix comprises a thiol-modified hyaluronic acid and a thiol reactive cross-linker molecule. In some embodiments, the thiol reactive cross-linker molecule is polyethylene glycol diacrylate.

In some aspects, provided herein are compositions comprising an isolated somatic cell that comprises an exogenously introduced nucleic acid encoding any of the multimodal TRAIL agents comprising a reporter module and a therapeutic TRAIL module described herein operably linked to at least one regulatory sequence.

In some embodiments of these aspects and all such aspects described herein, the isolated somatic cell is an adult stem cell. In some embodiments, the adult stem cell is a neural stem cell or a mesenchymal stem cell. In some embodiments, the neural stem cell is generated from a pluripotent stem cell.

In some embodiments of these aspects and all such aspects described herein, the isolated somatic cell is encapsulated in a matrix or scaffold. In some embodiments, the matrix comprises a synthetic extracellular matrix. In some embodiments, the matrix is biodegradeable. In some embodiments, the synthetic extracellular matrix comprises a thiol-modified hyaluronic acid and a thiol reactive cross-linker molecule. In some embodiments, the thiol reactive cross-linker molecule is polyethylene glycol diacrylate.

Also provided herein, in some aspects, are methods of treating a subject having a malignant condition comprising administering a therapeutically effective amount of any of the pharmaceutical compositions comprising the multimodal TRAIL agents described herein comprising a reporter module and a therapeutic TRAIL module, where the therapeutic TRAIL module comprises an extracellular domain of human TRAIL, and a pharmaceutically acceptable carrier.

In other aspects, provided herein are methods of treating a subject having a malignant condition comprising administering a therapeutically effective amount of cells comprising a nucleic acid sequence encoding any of the multimodal TRAIL agents described herein comprising a reporter module and a therapeutic TRAIL module, where the therapeutic TRAIL module comprises an extracellular domain of human TRAIL. In some embodiments of these methods and all such methods described herein, the cells are stem cells. In some such embodiments, the stem cell is a neural stem cell. In some embodiments of these methods and all such methods described herein, the cells are encapsulated in a matrix or scaffold. In some embodiments, the matrix comprises a synthetic extracellular matrix. In some embodiments, the matrix is biodegradeable. In some embodiments, the synthetic extracellular matrix comprises a thiol-modified hyaluronic acid and a thiol reactive cross-linker molecule. In some embodiments, the thiol reactive cross-linker molecule is polyethylene glycol diacrylate.

In some aspects, provided herein are methods of treating a subject having a malignant condition comprising administering a therapeutically effective amount of cells comprising any of the vectors comprising a nucleic acid sequence encoding any of the multimodal TRAIL agents comprising a reporter module and a therapeutic TRAIL module, where the therapeutic TRAIL module comprises an extracellular domain of human TRAIL, or one or more modules thereof, described herein. In some embodiments of these methods and all such methods described herein, the cells are stem cells. In some such embodiments, the stem cell is a neural stem cell. In some embodiments of these methods and all such methods described herein, the cells are encapsulated in a matrix or scaffold. In some embodiments, the matrix comprises a synthetic extracellular matrix. In some embodiments, the matrix is biodegradeable. In some embodiments, the synthetic extracellular matrix comprises a thiol-modified hyaluronic acid and a thiol reactive cross-linker molecule. In some embodiments, the thiol reactive cross-linker molecule is polyethylene glycol diacrylate.

In other aspects, provided herein are methods of treating a subject having a malignant condition comprising administering a therapeutically effective amount of a composition comprising an isolated somatic cell that comprises an exogenously introduced nucleic acid encoding any of the multimodal TRAIL agents comprising a reporter module and a therapeutic TRAIL module described herein operably linked to at least one regulatory sequence.

In some embodiments of these methods and all such methods described herein, the isolated somatic cell is an adult stem cell. In some embodiments, the adult stem cell is a neural stem cell or a mesenchymal stem cell. In some embodiments, the neural stem cell is generated from a pluripotent stem cell.

In some embodiments of these methods and all such methods described herein, the isolated somatic cell is encapsulated in a matrix or scaffold. In some embodiments, the matrix comprises a synthetic extracellular matrix. In some embodiments, the matrix is biodegradeable. In some embodiments, the synthetic extracellular matrix comprises a thiol-modified hyaluronic acid and a thiol reactive cross-linker molecule. In some embodiments, the thiol reactive cross-linker molecule is polyethylene glycol diacrylate.

In some embodiments of these methods and all such methods described herein, the extracellular domain of human TRAIL comprises amino acids 114-281 of SEQ ID NO: 1.

In some embodiments of these methods and all such methods described herein, the multimodal TRAIL agent further comprises a signal sequence. In some such embodiments, the signal sequence comprises SEQ ID NO: 2.

In some embodiments of these methods and all such methods described herein, the therapeutic TRAIL module further comprises an isoleucine zipper domain.

In some embodiments of these methods and all such methods described herein, the multimodal TRAIL agent further comprises a linker domain C-terminal to the reporter module and N-terminal to the therapeutic TRAIL module. In some such embodiments, the linker domain comprises at least eight amino acids. In some embodiments, the linker domain comprises the amino acid sequence of SEQ ID NO: 4.

In some embodiments of these methods and all such methods described herein, the malignant condition is a glioblastoma.

In some embodiments of these methods and all such methods described herein, the methods further comprise administering to the subject one or more additional chemotherapeutic agents, biologics, drugs, or treatments as part of a combinatorial therapy. In some such embodiments, the chemotherapeutic agent, biologic, drug, or treatment is selected from the group consisting of: radiation therapy, tumor resection surgery, gemcitabine, cisplastin, paclitaxel, carboplatin, bortezomib, AMG479, vorinostat, rituximab, temozolomide, rapamycin, ABT-737, and PI-103.

In some embodiments of these methods and all such methods described herein, the pharmaceutical compositions or cells are administered at a surgical site. In some embodiments, the surgical site is a tumor resection site.

Also provided herein, in some aspects, are pharmaceutical compositions comprising any of the multimodal TRAIL agents described herein comprising a reporter module and a therapeutic TRAIL module, where the therapeutic TRAIL module comprises an extracellular domain of human TRAIL, and a pharmaceutically acceptable carrier, for use in a method of treating a malignant condition.

In some aspects, provided herein are vectors comprising a nucleic acid sequence encoding any of the multimodal TRAIL agents comprising a reporter module and a therapeutic TRAIL module described herein, where the therapeutic TRAIL module comprises an extracellular domain of human TRAIL, or one or more modules thereof, for use in a method of treating a malignant condition.

In some embodiments of these uses and all such uses described herein, the vector is a lentiviral vector or an adenoviral vector.

Also provided herein, in some aspects, are cells comprising a nucleic acid sequence encoding any of the multimodal TRAIL agents comprising a reporter module and a therapeutic TRAIL module described herein, where the therapeutic TRAIL module comprises an extracellular domain of human TRAI for use in a method of treating a malignant condition.

In other aspects, provided herein are cells comprising any of the vectors comprising a nucleic acid sequence encoding any of the multimodal TRAIL agents, or one or more modules thereof, described herein for use in a method of treating a malignant condition. In some embodiments of these uses and all such uses described herein, the cell is a stem cell. In some such embodiments, the stem cell is a neural stem cell or a mesenchymal stem cell. In some embodiments of these methods and all such methods described herein, the cell is encapsulated in a matrix or scaffold. In some embodiments, the matrix comprises a synthetic extracellular matrix. In some embodiments, the matrix is biodegradeable. In some embodiments, the synthetic extracellular matrix comprises a thiol-modified hyaluronic acid and a thiol reactive cross-linker molecule. In some embodiments, the thiol reactive cross-linker molecule is polyethylene glycol diacrylate.

In some aspects, provided herein are compositions comprising an isolated somatic cell that comprises an exogenously introduced nucleic acid encoding any of the multimodal TRAIL agents comprising a reporter module and a therapeutic TRAIL module described herein operably linked to at least one regulatory sequence for use in a method of treating a malignant condition.

In some embodiments of these uses and all such uses described herein, the isolated somatic cell is an adult stem cell. In some embodiments, the adult stem cell is a neural stem cell or a mesenchymal stem cell. In some embodiments, the neural stem cell is generated from a pluripotent stem cell.

In some embodiments of these uses and all such uses described herein, the isolated somatic cell is encapsulated in a matrix or scaffold. In some embodiments, the matrix comprises a synthetic extracellular matrix. In some embodiments, the matrix is biodegradeable. In some embodiments, the synthetic extracellular matrix comprises a thiol-modified hyaluronic acid and a thiol reactive cross-linker molecule. In some embodiments, the thiol reactive cross-linker molecule is polyethylene glycol diacrylate.

In some embodiments of these uses and all such uses described herein, the malignant condition is a glioblastoma.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "multimodal TRAIL agent" refers to a molecule comprising at least two functional or biological activities—therapeutic and diagnostic. The therapeutic activity, e.g., cytotoxicity, is provided by the therapeutic TRAIL module, as the term is defined herein. The diagnostic activity is provided by the reporter module, as the term is defined herein.

As used herein, the terms "therapeutic TRAIL module" or "therapeutic TRAIL variant" refer to a polypeptide, or a nucleotide sequence encoding such a polypeptide, comprising an extracellular domain of human TRAIL as described in U.S. Pat. No. 6,284,236, the contents of which are herein incorporated in their entirety by reference.

As used herein, the term "reporter module" refers to a molecule that is selected, designed, or engineered to permit in vivo monitoring and visualization of the multimodal TRAIL agent. Preferably, the reporter module permits minimally invasive monitoring and visualization of the multimodal TRAIL agent.

As used herein, the terms "secretion signal sequence," "secretion sequence," "secretion signal peptide," or "signal sequence," refer to a sequence that is usually about 3-60 amino acids long and that directs the transport of a propeptide to the endoplasmic reticulum and through the secretory pathway during protein translation.

As used herein, a "leucine zipper domain" refers to a naturally occurring or synthetic peptide that promotes oligomerization of the proteins in which it is found.

The terms "patient," "subject," and "individual" are used interchangeably herein, and refer to an animal, particularly a human, to whom it is desirable to administer a composition comprising a multimodal TRAIL agent or cells expressing a multimodal TRAIL agent. The term "subject" or "patient" as used herein also refers to human and non-human animals. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and any domestic animal or pet, as well as non-mammals such as chickens, amphibians, reptiles etc. In one embodiment, the subject is human.

As used herein, the terms "patient sample" or "biological sample" refers to a fluid sample, a cell sample, a tissue sample or an organ sample obtained from a patient. In some embodiments, a cell or population of cells, or a quantity of tissue or fluid are obtained from a subject. Often, a "patient sample" will contain cells from the animal, but the term can also refer to non-cellular biological material, such as non-cellular fractions of blood, saliva, or urine. Biological samples include, but are not limited to, tissue biopsies, scrapes (e.g. buccal scrapes), whole blood, plasma, serum, urine, saliva, cell culture, tissue biopsies, mucous membrane samples, feces, intestinal lavage, joint fluid, cerebrospinal fluid, a biliary sample, a respiratory secretion, such as sputum, brochoalveolar lavage fluid sample, and the like. A biological sample or tissue sample can refer to a sample of tissue or fluid isolated from an individual, including but not limited to, for example, blood, plasma, serum, urine, stool, sputum, spinal fluid, pleural fluid, lymph fluid, the external sections of the skin, respiratory, intestinal, and genitourinary tracts, tears, saliva, and organs. Samples can include frozen or paraffin-embedded tissue. The term "sample" includes any material derived by processing such a sample. Derived samples may, for example, include nucleic acids or proteins extracted from the sample or obtained by subjecting the sample to techniques such as amplification or reverse transcription of mRNA, isolation and/or purification of certain components, etc.

The terms "stem cell" or "undifferentiated cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.). A stem cell is capable of proliferation and giving rise to more such stem cells while maintaining its developmental potential. In theory, self-renewal can occur by either of two major mechanisms. Stem cells can divide asymmetrically, which is known as obligatory asymmetrical differentiation, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered stem cells, the range of cell types each such stem cell can give rise to, i.e., their "developmental potential," can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity may be natural or may be induced artificially upon treatment with various factors. Cells that begin as stem cells might proceed toward a differentiated phenotype, but then can be induced to "reverse" and re-express the stem cell phenotype, a term often referred to as "dedifferentiation" or "reprogramming" or "retrodifferentiation" by persons of ordinary skill in the art.

The term "somatic stem cell" is used herein to refer to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally occurring somatic stem cells include, but are not limited to, neural stem cells, neural crest stem cells, mesenchymal stem cells, hematopoietic stem cells, and pancreatic stem cells.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cell forming the body of an organism, as opposed to a germline cell.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene. In some embodiments, an expression product is transcribed from a sequence that does not encode a polypeptide, such as a microRNA.

The terms "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

The term "transduction" as used herein refers to the use of viral particles or viruses to introduce exogenous nucleic acids into a cell.

The term "transfection" as used herein refers the use of methods, such as chemical methods, to introduce exogenous nucleic acids, such as the nucleic acid sequences encoding the multimodal TRAIL agents described herein, into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to, cyclodextrin, polymers, liposomes, nanoparticles, cationic lipids or mixtures thereof (e.g., DOPA, Lipofectamine and Upti-Fectin), and cationic polymers, such as DEAE-dextran or polyethylenimine.

The term "anti-cancer therapy" refers to a therapy useful in treating a malignancy or cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin®), anti-CD20 antibodies, an epidermal growth factor receptor (EGFR) antagonist (e.g., a tyrosine kinase inhibitor), HER1/EGFR inhibitor (e.g., erlotinib (Tarceva®)), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., .COPYRGT. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The multimodal TRAIL agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a malignant condition or cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s) of a malignant disease, diminishment of extent of a malignant disease, stabilized (i.e., not worsening) state of a malignant disease, delay or slowing of progression of a malignant disease, amelioration or palliation of the malignant disease state, and remission (whether partial or total), whether detectable or undetectable. The term "treatment" of a disease also includes providing relief from the symptoms or side-effects of the disease (including palliative treatment).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth.

BRIEF DESCRIPTION OF THE FIGURES

FIGS. 6A-6D depict a linear map of LV transfer vector, correlation of cell number, and in vitro photon emission. (6A) Schematic representations of self-inactivating lentiviral transfer plasmid based on HIV-1 (CS-CW2). The S-TRAIL and luciferase fusions were cloned downstream of the CMV promoter and upstream of and IRES element driving GFP expression. (6B) Representative photomicrograph showing transduction of 293T by LV encoding S-TRAIL and luciferase fusion proteins. (6C-6D) In vitro bioluminescence imaging showing the correlation between cell number and FLuc expression (6C) or GpLuc/RLucO photon emission (6D) in U251 cells transduced with LV-GFP-FLuc and LV-SGpL2TR or LV-SRLOL2TR.

FIGS. 7A-7D depict the effects of altered signal sequence and in vivo light emission. (7A) Schematic representation of lentiviral transfer vectors encoding fusions between Flt3L N-terminal signal sequence and GpLuc or SRLO. (7B-7D) Summary data showing the linear correlation between cell number and photon emission and representative fluorescent images of cells transduced with FLuc-DsRed2 and either SGp or SRLO of transduced cells.

DETAILED DESCRIPTION

Figure 1:
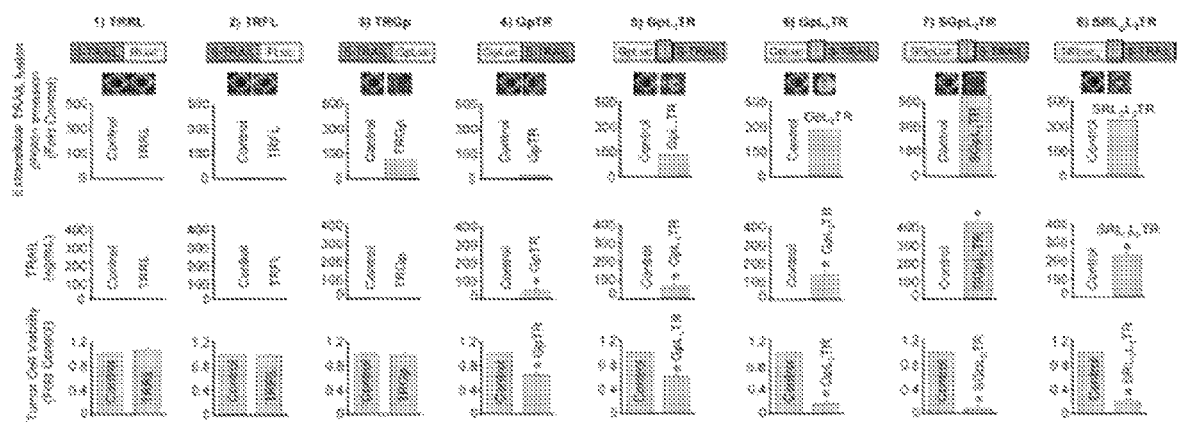
FIG. 1 depicts the engineering and screening of multiple S-TRAIL and luciferase fusions in vitro. Schematic representations of lentiviral transfer vectors bearing IRES-GFP cassettes and encoding various fusions between secreted variant of the pro-apoptotic protein tumor necrosis factor-related apoptosis-inducing ligand (S-TRAIL) and different luciferase proteins are shown. Direct fusion variants: (1) TRAIL-Rluc, (2) TRAIL-Fluc, (3) TRAIL-GpLuc, (4) GpLuc-TRAIL. Variants to test intramolecular spacing: (5) GpLuc-linker 1-TRAIL, (6) GpLuc-linker 2-TRAIL. Variants to test modification of secretion sequence: (7) SGpLuc-Linker 2-TRAIL, (8) SRlucO-linker 2-TRAIL. 293T cells were transduced with lentiviral vectors encoding the designated fusion variant. Bioluminescence imaging and enzyme-linked immunosorbent assay were performed on conditioned medium from the transduced cells to determine diagnostic luciferase activity or concentration of S-TRAIL, respectively. Therapeutic activity of each variant was determined by luciferase-based assay on human Gli36-EGFRvIII cells 24 hours after incubation with equal volumes of conditioned media from lentiviral transduced 293T cells. Abbreviations: GpL1TR, GpLuc-linker 1-TRAIL; GpL2TR, GpLuc-linker 2-TRAIL; GpTR, GpLuc-TRAIL; SGpL2TR, SGpLuc-Linker 2-TRAIL; SRLOL2TR, SRlucO-linker 2-TRAIL; TRFL, TRAIL-Fluc; TRGp, TRAIL-GpLuc; TRRL, TRAIL-Rluc.

Provided herein are novel, multimodal, therapeutic agents comprising a therapeutic, secretable domain, such as domain of tumor necrosis factor-related apoptosis-inducing ligand (TRAIL), and a reporter domain for use as multifunctional therapeutic and diagnostic agents in the treatment of cancers, such as glioblastoma. As described herein, the multimodal therapeutic agents, such as multimodal TRAIL agents, are useful in combinatorial therapies, such as with chemotherapy, radiotherapy, and surgical interventions. Activation of cell surface receptors, such as death receptors (DRs), by the multimodal therapeutic agents and cells expressing such agents, such as engineered stem cells, provided herein, represent attractive therapeutic strategies to promote apoptosis of tumor cells through the activation of extrinsic and intrinsic apoptotic pathways.

As described herein, diagnostic and therapeutic murine neural stem cells (NSCs) encapsulated in soluble extracellular matrix (sECM) were tested in a murine model of GBM resection. As demonstrated herein, sECM encapsulation of mNSC engineered to secrete a multimodal TRAIL agent significantly increased retention time in the GBM resection cavity, permitted robust tumor-selective migration and allowed secretion of anti-tumor multimodal TRAIL proteins from the sECM encapsulated stem cells in vivo. Mimicking the clinical scenario of GBM resection and subsequent treatment, TRAIL-secreting sECM encapsulated mNSC transplanted in the resection cavity eradicated residual tumor cells, delayed tumor re-growth and significantly increased survival of mice. Furthermore, we demonstrate herein that TRAIL-secreting sECM-encapsulated stem cells transplanted in the resection cavity significantly delayed tumor regrowth in mice bearing both established (U87) and primary invasive (GBM8) GBMs and significantly increased survival of mice bearing established GBMs.

In this study sECMs were employed that are based on a thiol-modified hyaluronic acid (HA) and a thiol reactive cross-linker (polyethylene glycol diacrylate) which provides biocompatibility, physiological relevance, and customizability (Xu et al. Prostaglandin Other Lipid Mediat 2009). Additionally, release profiles of sECM used in this study were ideal to permit both migratory stem cells and secreted therapeutic proteins to exit the sECM. sECM encapsulation dramatically increased the survival of mNSC in resection cavities as compared to non-sECM encapsulated cells over a period of 4 weeks. We demonstrate herein that sECM encapsulated engineered mNSC are effective by way of increasing the concentration of therapeutic stem cells at the site of tumor resection to extend the drug exposure time to tumor cells.

The ability of TRAIL to selectively target tumor cells while remaining harmless to most normal cells makes it an attractive candidate for an apoptotic therapy for highly malignant brain tumors. However, sustained levels of TRAIL are key to improving the efficiency and potency of TRAIL-based pro-apoptotic cancer therapy. The results described herein confirm that TRAIL is a potent inhibitor of brain tumor growth, and that encapsulated mNSC-S-TRAIL cytotoxic therapy is highly efficient in inducing apoptosis in residual GBM cells following GBM resection.

The studies described herein reveal the fate and therapeutic efficacy of engineered and sECM encapsulated mNSC in a mouse model of GBM resection. Using the compositions and methods described herein, advances can be made in the way stem cells can be engineered and used clinically in cancer patients, such as brain tumor patients. In some embodiments of the methods described herein, neurosurgical removal of the main tumor mass at the time of surgery can be combined with implantation of patient's own reprogrammed cells or mesenchymal stem cells, therapeutically engineered with anti-tumor agent(s) and encapsulated in sECM, into the resection cavity of the tumor. These cells would result in killing of both residual and invasive tumor cells with the ultimate goal of improving patient outcomes.

TRAIL and Apoptosis

Tumour necrosis factor-related apoptosis-inducing ligand (TRAIL) is normally expressed on both normal and tumour cells as a non-covalent homotrimeric type-II transmembrane protein (memTRAIL). In addition, a naturally occurring soluble form of TRAIL (solTRAIL) can be generated due to alternative mRNA splicing or proteolytic cleavage of the extracellular domain of memTRAIL and thereby still retaining tumour-selective pro-apoptotic activity. TRAIL utilizes an intricate receptor system comprising four distinct membrane receptors, designated TRAIL-R1, TRAIL-R2, TRAIL-R3 and TRAIL-R4. Of these receptors, only TRAIL-R1 and TRAIL-2 transmit an apoptotic signal. These two receptors belong to a subgroup of the TNF receptor family, the so-called death receptors (DRs), and contain the hallmark intracellular death domain (DD). This DD is critical for apoptotic signalling by death receptors (J. M. A. Kuijlen et al., Neuropathology and Applied Neurobiology, 2010 Vol. 36 (3), pp. 168-182).

Apoptosis is integral to normal, physiologic processes that regulate cell number and results in the removal of unnecessary or damaged cells. Apoptosis is frequently dysregulated in human cancers, and recent advancements in the understanding of the regulation of programmed cell death pathways has led to the development of agents to reactivate or activate apoptosis in malignant cells. This evolutionarily conserved pathway can be triggered in response to damage to key intracellular structures or the presence or absence of extracellular signals that provide normal cells within a multicellular organism with contextual information.

TRAIL activates the "extrinsic pathway" of apoptosis by binding to TRAIL-R1 and/or TRAIL-R2, whereupon the adaptor protein Fas-associated death domain and initiator caspase-8 are recruited to the DD of these receptors. Assembly of this "death-inducing signaling complex" (DISC) leads to the sequential activation of initiator and effector caspases, and ultimately results in apoptotic cell death. The extrinsic apoptosis pathway triggers apoptosis independently of p53 in response to pro-apoptotic ligands, such as TRAIL. TRAIL-R1 can induce apoptosis after binding non-cross-linked and cross-linked sTRAIL. TRAIL-R2 can only be activated by cross-linked sTRAIL. Death receptor binding leads to the recruitment of the adaptor FADD and initiator procaspase-8 and 10 to rapidly form the DISC. Procaspase-8 and 10 are cleaved into its activated configuration caspase-8 and 10. Caspase-8 and 10 in turn activate the effector caspase-3, 6 and 7, thus triggering apoptosis.

In certain cells, the execution of apoptosis by TRAIL further relies on an amplification loop via the "intrinsic mitochondrial pathway" of apoptosis. The mitochondrial pathway of apoptosis is a stress-activated pathway, e.g., upon radiation, and hinges on the depolarization of the mitochondria, leading to release of a variety of pro-apoptotic factors into the cytosol. Ultimately, this also triggers effector caspase activation and apoptotic cell death. This mitochondrial release of pro-apoptotic factors is tightly controlled by the Bcl-2 family of pro- and anti-apoptotic proteins. In the case of TRAIL receptor signaling, the Bcl-2 homology (BH3) only protein 'Bid' is cleaved into a truncated form (tBid) by active caspase-8. Truncated Bid subsequently activates the mitochondrial pathway.

TRAIL-R3 is a glycosylphosphatidylinositol-linked receptor that lacks an intracellular domain, whereas TRAIL-R4 only has a truncated and non-functional DD. The latter two receptors are thought, without wishing to be bound or limited by theory, to function as decoy receptors that modulate TRAIL sensitivity. Evidence suggests that TRAIL-R3 binds and sequesters TRAIL in lipid membrane microdomains. TRAIL-R4 appears to form heterotrimers with TRAIL-R2, whereby TRAIL-R2-mediated apoptotic signalling is disrupted. TRAIL also interacts with the soluble protein osteoprotegerin Diffuse expression of TRAIL has been detected on liver cells, bile ducts, convoluted tubules of the kidney, cardiomyocytes, lung epithelia, Leydig cells, normal odontogenic epithelium, megakaryocytic cells and erythroid cells. In contrast, none or weak expression of TRAIL was observed in colon, glomeruli, Henle's loop, germ and Sertoli cells of the testis, endothelia in several organs, smooth muscle cells in lung, spleen and in follicular cells in the thyroid gland. TRAIL protein expression was demonstrated in glial cells of the cerebellum in one study. Vascular brain endothelium appears to be negative for TRAIL-R1 and weakly positive for TRAIL-R2. With regard to the decoy receptors, TRAIL-R4 and TRAIL-R3 have been detected on oligodendrocytes and neurones.

TRAIL-R1 and TRAIL-R2 are ubiquitously expressed on a variety of tumour types. Importantly for the compositions and methods comprising multimodal TRAIL agents described herein, TRAIL-R1 and TRAIL-R2 are also expressed in the tumour tissue from astrocytoma grade II and glioblastoma patients. In a study on 62 primary GBM tumour specimens, TRAIL-R1 and TRAIL-R2 were expressed in 75% and 95% of the tumours, respectively. Of note, a statistically significant positive association was identified between agonistic TRAIL receptor expression and survival. Highly malignant tumours express a higher amount of TRAIL receptors in comparison with less malignant tumours or normal tissue. In general TRAIL-R2 is more frequently expressed on tumour cells than TRAIL-R1.

Accordingly, the term "Tumour necrosis factor-related apoptosis-inducing ligand" or "TRAIL" as used herein refers to the 281 amino acid polypeptide having the amino acid sequence of: MAMMEVQGGPSLGQTCVLIVIFTV-LLQSLCVAVTYVYFTNELKQMQDKYSKS-GIACFLKED DSYWDPNDEESMNSPCWQVKWQL-RQLVRKMILRTSEETISTVQEKQQNISPLVRERGPQRV AAHITGTRGRSNTLSSPNSKNEKALGRKINSWESS-RSGHSFLSNLHLRNGELVIHEKGFYYIYS QTY-FRFQEEIKENTKNDKQMVQYIYKYTSYPDPILLMK-SARNSCWSKDAEYGLYSIYQGGIF ELKENDRIFVS-VTNEHLIDMDHEASFFGAFLVG (SEQ ID NO: 1), as described by, e.g., NP_003801.1, together with any naturally occurring allelic, splice variants, and processed forms thereof. Typically, TRAIL refers to human TRAIL. The term TRAIL, in some embodiments of the aspects described herein, is also used to refer to truncated forms or fragments of the TRAIL polypeptide, comprising, for example, specific TRAIL domains or residues thereof. Reference to any such forms of TRAIL can be identified in the application, e.g., by "TRAIL (39-281)." The amino acid sequence of the human TRAIL molecule as presented in SEQ ID NO: 1 comprises an N-terminal cytoplasmic domain (amino acids 1-18), a transmembrane region (amino acids 19-38), and an extracellular domain (amino acids 39-281). The extracellular domain comprises the TRAIL receptor-binding region. TRAIL also has a spacer region between the C-terminus of the transmembrane domain and a portion of the extracellular domain This spacer region, located at the N-terminus of the extracellular domain, consists of amino acids 39 through 94 of SEQ ID NO: 1. Amino acids 138 through 153 of SEQ ID NO: 1 correspond to a loop between the β sheets of the folded (three dimensional) human TRAIL protein.

Multimodal TRAIL Agents

Described herein multimodal TRAIL agents comprising a therapeutic, secretable domain, such as domain of tumor necrosis factor-related apoptosis-inducing ligand (TRAIL), and a reporter domain for use as multifunctional therapeutic and diagnostic agents in the treatment of cancers, such as glioblastoma. These multimodal TRAIL agents are novel therapeutic tools for utilizing the apoptotic effects on cancer cells mediated by TRAIL, either by administering these agents directly or via expression of these agents in engineered cells, such as stem cells.

Preclinical studies have illustrated the promise of targeting TRAIL activity and using TRAIL as a therapeutic reagent in vivo with no or minimal toxicity. A variety of recombinant tumour necrosis factor-related apoptosis-inducing ligand (TRAIL) molecules and agonistic antibodies directed at TRAIL death receptors TRAIL-R1 and/or TRAIL-R1 have been developed. A recombinant trimeric form of TRAIL is being explored in an ongoing multicentre clinical trail for B-CLL patients. Importantly, no significant side effects have been reported so far, thus corroborating the safety of TRAIL treatment in humans. In addition, a number of agonistic antibodies (e.g., HGS-ETR1, HGS-ETR2, HGS-TR2J, LBY135, CS-1008, AMG 655) that selectively target TRAIL-R1 or TRAIL-R2 have been developed. All of these antibodies have potent tumouricidal activity in vitro and in vivo and appear to have a low toxicity profile in early-phase clinical studies.

However, the efficacy of using naturally occurring soluble TRAIL is hampered by various factors, including rapid clearance from the circulation by the kidney. Reports have demonstrated that soluble TRAIL has an approximate half-life of only 30 minutes in primates, and a similar pharmacokinetic profile in humans in a phase I clinical trial (Ashkenazi A. et al., J Clin Oncol 2008; 26: 3621-30, and Kelley S K et al., J Pharmacol Exp Ther 2001; 299: 31-8, the contents of which are herein incorporated by reference in their entireties). Some reports have attempted to overcome the rapid clearance by fusing soluble TRAIL with an antibody derivative, such as scFv245 (Bremer E. et al., J Mol Med 2008; 86: 909-24; Bremer E, et al., Cancer Res 2005; 65: 3380-88; Bremer E, et al., J Biol Chem 2005; 280: 10025-33, and Stieglmaier J, et al., Cancer Immunol Immunother 2008; 57: 233-46).

One of the primary challenges to achieving effective anti-tumor therapies is highly efficient delivery of the anti-tumor agent specifically to the tumor, while minimizing toxicity to nonmalignant tissue. Although simple to administer, systemic administration of therapies can lead to accumulation of the toxic compounds at high levels in the liver and kidneys, resulting in dose-limiting renal- and hepato-toxicity (Kelley et al. J Pharmacol Exp Ther 2001, Lin, Drug Metab Dispos 1998). TRAIL has been shown to have minimal cytotoxic effects on normal tissue; however, its short half-life and accumulation after systemic injection have been limitations to its potential use in clinics (Ashkenazi et al., J Clin Oncol 2008). Because of their potential to migrate to sites of disease and integrate into the cytoarchitecture of the brain, stem cells (e.g., neural stem cells, mesenchymal stem cells) have received much interest for the treatment of numerous neurologic disorders (Corsten and Shah, Lancet Oncology 2008, Singec et al. Annu Rev Med 2007). Previous studies from our lab and others demonstrated that neural stem cells (NSCs) and human mesenchymal stem cells (MNCs) migrate extensively throughout the murine brain and exhibit an inherent capacity to home to established gliomas (Sasportas et al. Proc Natl Acad Sci 2009, Shah et al Ann Neurol 2005, Shah et al. J Neurosci 2008, the contents of each of which are herein incorporated by reference in their entireties). Stem cells armed with S-TRAIL inhibited progression of gliomas in a xenogenic transplant model (Sasportas et al. Proc Natl Acad Sci 2009, Shah et al Ann Neurol 2005); however, assessing the pharmacokinetics of the molecules released by therapeutic NSC has been difficult.

Therapeutic TRAIL Modules

As demonstrated herein, the inventors have engineered multimodal TRAIL agents that have both increased apoptosis-inducing abilities and can be secreted from a cell, such as a neural stem cell, and can be imaged in real-time for diagnostic purposes, for use in the compositions and methods described herein (K. Shah et al., Cancer Research 2004, 64: 3236-3242; K. Shah et al., Molecular Therapy 2005, 11(6): 926-931; Shah K, et al., Ann Neurol 2005; 57: 34-41; Sasportas L S et al., Proc Natl Acad Sci USA 2009; 106: 4822-7; Shah K. et al., 1. J Neurosci 2008; 28: 4406-13; Hingtgen S et al., Mol Cancer Ther 2008; 7: 3575-85; the contents of each of which is herein incorporated by reference in their entireties). These multimodal TRAIL agents comprise a therapeutic TRAIL module or therapeutic TRAIL domain or variant thereof having TRAIL apoptotic activity. As used herein, a "therapeutic TRAIL module," "therapeutic TRAIL domain," or "therapeutic TRAIL variant" refers to a polypeptide, or a nucleotide sequence encoding such a polypeptide, comprising an extracellular domain of human TRAIL, such as a human TRAIL of SEQ ID NO: 1, and maintaining TRAIL apoptotic activity. In some embodiments of the aspects described herein, an N-terminal secretion signal sequence is fused to the N-terminal of the extracellular domain of human TRAIL. In some embodiments of the aspects described herein, the therapeutic TRAIL module can further comprise an isoleucine zipper domain.

Accordingly, provided herein, in some aspects, are multimodal TRAIL agents comprising a therapeutic human TRAIL domain or variant thereof, wherein the therapeutic human TRAIL domain comprises an extracellular domain of human TRAIL. In some embodiments of the aspects described herein, the extracellular domain of human TRAIL comprises amino acids 39-281 of SEQ ID NO: 1. In some embodiments of the aspects described herein, the extracellular domain of human TRAIL comprises amino acids 95-281 of SEQ ID NO: 1. In some embodiments of the aspects described herein, the extracellular domain of human TRAIL comprises amino acids 114-281 of SEQ ID NO: 1. In some embodiments of the aspects described herein, the extracellular domain of human TRAIL comprises a sequence having at least 90% identity to amino acids 114-281 of SEQ ID NO: 1 and retains TRAIL apoptotic activity. In some embodiments of the aspects described herein, the extracellular domain of human TRAIL used in a multimodal TRAIL agent consists essentially of amino acids 114-281 of SEQ ID NO: 1. In some embodiments of the aspects described herein, the extracellular domain of human TRAIL used in a multimodal TRAIL agent consists of amino acids 114-281 of SEQ ID NO: 1.

Variants and derivatives of native TRAIL proteins for use in the therapeutic TRAIL modules that retain a desired biological activity of TRAIL, such as "TRAIL apoptotic activity" are also within the scope of the compositions and methods described herein. In some embodiments, the biological or apoptotic activity of a therapeutic TRAIL module is essentially equivalent to the biological activity of a native TRAIL protein. In some such embodiments, biological activity of a native TRAIL protein is TRAIL apoptotic activity. One measurement of TRAIL apoptotic activity by a TRAIL variant or TRAIL domain is the ability to induce apoptotic death of Jurkat cells. Assay procedures for identifying biological activity of TRAIL variants by detecting apoptosis of target cells, such as Jurkat cells, are well known in the art. DNA laddering is among the characteristics of cell death via apoptosis, and is recognized as one of the observable phenomena that distinguish apoptotic cell death from necrotic cell death. Apoptotic cells can also be identified using markers specific for apoptotic cells, such as Annexin V, in combination with flow cytometric techniques, as known to one of skill in the art. Further examples of assay techniques suitable for detecting death or apoptosis of target cells include those described in the Examples section.

TRAIL variants can be obtained by mutations of native TRAIL nucleotide sequences, for example. A "TRAIL variant," as referred to herein, is a polypeptide substantially homologous to a native TRAIL, but which has an amino acid sequence different from that of native TRAIL because of one or a plurality of deletions, insertions or substitutions. "TRAIL encoding DNA sequences" encompass sequences that comprise one or more additions, deletions, or substitutions of nucleotides when compared to a native TRAIL DNA sequence, but that encode a TRAIL protein or fragment thereof that is essentially biologically equivalent to a native TRAIL protein, i.e., has the same apoptosis inducing activity.

The variant amino acid or DNA sequence preferably is at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to a native TRAIL sequence. The degree of homology or percent identity) between a native and a mutant sequence can be determined, for example, by comparing the two sequences using freely available computer programs commonly employed for this purpose on the world wide web.

Alterations of the native amino acid sequence can be accomplished by any of a number of known techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

TRAIL variants can, in some embodiments, comprise conservatively substituted sequences, meaning that one or more amino acid residues of a native TRAIL polypeptide are replaced by different residues, and that the conservatively substituted TRAIL polypeptide retains a desired biological activity, i.e., apoptosis inducing activity or TRAIL apoptotic activity, that is essentially equivalent to that of the native TRAIL polypeptide. Examples of conservative substitutions include substitution of amino acids that do not alter the secondary and/or tertiary structure of TRAIL.

In other embodiments, TRAIL variants can comprise substitution of amino acids that have not been evolutionarily conserved. Conserved amino acids located in the C-terminal portion of proteins in the TNF family, and believed to be important for biological activity, have been identified. These conserved sequences are discussed in Smith et al. (Cell, 73:1349, 1993, see page 1353 and FIG. 6); Suda et al. (Cell, 75:1169, 1993, see FIG. 7); Smith et al. (Cell, 76:959, 1994, see FIG. 3); and Goodwin et al. (Eur. J. Immunol., 23:2631, 1993, see FIG. 7 and pages 2638-39) hereby incorporated in their entireties by reference. Advantageously, in some embodiments, these conserved amino acids are not altered when generating conservatively substituted sequences. In some embodiments, if altered, amino acids found at equivalent positions in other members of the TNF family are substituted. Among the amino acids in the human TRAIL protein of SEQ ID NO:1 that are conserved are those at positions 124-125 (AH), 136 (L), 154 (W), 169 (L), 174 (L), 180 (G), 182 (Y), 187 (Q), 190 (F), 193 (Q), and 275-276 (FG) of SEQ ID NO:1. Another structural feature of TRAIL is a spacer region (i.e., TRAIL (39-94)) between the C-terminus of the transmembrane region and the portion of the extracellular domain that is believed to be important for biological apoptotic activity. In some embodiments, when the desired biological activity of TRAIL domain is the ability to bind to a receptor on target cells and induce apoptosis of the target cells substitution of amino acids occurs outside of the receptor-binding domain.

A given amino acid of a TRAIL domain can, in some embodiments, be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. TRAIL polypeptides comprising conservative amino acid substitutions can be tested in any one of the assays described herein to confirm that a desired TRAIL apoptotic activity of a native TRAIL molecule is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particularly preferred conservative substitutions for use in the TRAIL variants described herein are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any cysteine residue not involved in maintaining the proper conformation of the multimodal TRAIL agent also can be substituted, generally with serine, to improve the oxidative stability of the molecule and prevent aberrant crosslinking Conversely, cysteine bond(s) can be added to the multimodal TRAIL agent to improve its stability or facilitate oligomerization.

Signal Sequences

The multimodal TRAIL agents described herein can further comprise, in some embodiments, a secretion signal sequence that permits a cell engineered to express a multimodal TRAIL agent to secrete the agent. As used herein, the terms "secretion signal sequence," "secretion sequence," "secretion signal peptide," or "signal sequence," refer to a sequence that is usually about 3-60 amino acids long and that directs the transport of a propeptide to the endoplasmic reticulum and through the secretory pathway during protein translation. As used herein, a signal sequence, which can also be known as a signal peptide, a leader sequence, a prepro sequence or a pre sequence, does not refer to a sequence that targets a protein to the nucleus or other organelles, such as mitochondria, chloroplasts and apicoplasts. In some embodiments of the multimodal TRAIL agents described herein, a "secretion signal sequence" comprises 5 to 15 amino acids with hydrophobic side chains that are recognized by a cytosolic protein, SRP (Signal Recognition Particle), which stops translation and aids in the transport of an mRNA-ribosome complex to a translocon in the membrane of the endoplasmic reticulum. In some embodiments of the multimodal TRAIL agents described herein, the signal peptide comprises at least three regions: an amino-terminal polar region (N region), where frequently positive charged amino acid residues are observed, a central hydrophobic region (H region) of 7-8 amino acid residues and a carboxy-terminal region (C region) that includes the cleavage site. Commonly, the signal peptide is cleaved from the mature protein with cleavage occurring at this cleavage site.

The secretory signal sequence is operably linked to the sequence encoding the therapeutic TRAIL module of the multimodal TRAIL agents described herein, such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences can be positioned elsewhere in the nucleotide sequence of interest (see, e.g., Welch et al., U.S. Pat. No. 5,037,743; Holland et al., U.S. Pat. No. 5,143,830).

In some embodiments of the aspects described herein, the secretory sequence comprises amino acids 1-81 of the following Flt3L amino acid sequence: MTVLAPAWSP NSSLLLLLLL LSPCLRGTPD CYFSHSPISS NFKVK- FRELT DHLLKDYPVT VAVNLQDEKH CKALWSLFLA QRWIEQLKTV AGSKMQTLLE DVNTEIHFVT SCTFQ- PLPEC LRFVQTNISH LLKDTCQLL ALKPCIGKAC QNFSRCLEVQ CQPDSSTLLP PRSPIALEAT ELPEP- RPRQL LLLLLLLLPL TLVLLAAAWG LRWQRARRRG ELHPGVPLPS HP (SEQ ID NO: 2, GenBank Accession P49772), or a fragment thereof. In some embodiments of the aspects described herein, the signal peptide comprises amino acids 1-81 of SEQ ID NO: 2. In some embodiments of the aspects described herein, the secretory signal sequence comprises a sequence having at least 90% identity to amino acids 1-81 of SEQ ID NO: 2. In some embodiments of the aspects described herein, the secretory signal sequence consists essentially of amino acids 1-81 of SEQ ID NO: 2. In some embodiments of the aspects described herein, the secretory signal sequence consists of amino acids 1-81 of SEQ ID NO: 2.

While the secretory signal sequence can be derived from Flt3L, in other embodiments a suitable signal sequence can also be derived from another secreted protein or synthesized de novo. Other secretory signal sequences which can be substituted for the Flt3L signal sequence for expression in eukaryotic cells include, for example, naturally-occurring or modified versions of the human IL-17RC signal sequence, otPA pre-pro signal sequence, human growth hormone signal sequence, human CD33 signal sequence Ecdysteroid Glucosyltransferase (EGT) signal sequence, honey bee Melittin (Invitrogen Corporation; Carlsbad, Calif.), baculovirus gp67 (PharMingen: San Diego, Calif.) (US Pub. No. 20110014656). Additional secretory sequences include secreted alkaline phosphatase signal sequence, interleukin-1 signal sequence, CD-14 signal sequence and variants thereof (US Pub. No. 20100305002) as well as the following peptides and derivatives thereof: Sandfly Yellow related protein signal peptide, silkworm friboin LC signal peptide, snake PLA2, *Cyrpidina noctiluca* luciferase signal peptide, and pinemoth fibroin LC signal peptide (US Pub. No. 20100240097). Further signal sequences can be selected from databases of protein domains, such as SPdb, a signal peptide database described in Choo et al., BMC Bioinformatics 2005, 6:249, LOCATE, a mammalian protein localization database described in Sprenger et al. Nuc Acids Res, 2008, 36:D230D233, or identified using computer modeling by those skilled in the art (Ladunga, Curr Opin Biotech 2000, 1:13-18).

Selection of appropriate signal sequences and optimization or engineering of signal sequences is known to those skilled in the art (Stern et al., Trends in Cell & Molecular Biology 2007 2:1-17; Barash et al., Biochem Biophys Res Comm 2002, 294:835-842). In some embodiments, signal sequences can be used that comprise a protease cleavage site for a site-specific protease (e.g., Factor IX or Enterokinase). This cleavage site can be included between the pro sequence and the bioactive secreted peptide sequence, e.g., TRAIL domain, and the pro-peptide can be activated by the treatment of cells with the site-specific protease (US Pub. No. 20100305002).

Leucine Zippers

The therapeutic TRAIL modules and multimodal TRAIL agents described herein can, in some embodiments, further comprise a leucine zipper domain sequence. As used herein, "leucine zipper domains" refer to naturally occurring or synthetic peptides that promote oligomerization of the proteins in which they are found. The leucine zipper is a super-secondary structure that functions as a dimerization domain, and its presence generates adhesion forces in parallel alpha helices. A single leucine zipper comprises multiple leucine residues at approximately 7-residue intervals, which forms an amphipathic alpha helix with a hydrophobic region running along one side. The dimer formed by a zipper domain is stabilized by the heptan repeat, designated (abcdefg)$_n$ according to the notation of McLachlan and Stewart (J. Mol. Biol. 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix. The residues at position d (often leucine) contribute large hydrophobic stabilization energies, and are important for oligomer formation (Krystek et al., Int. J. Peptide Res. 38:229, 1991). This hydrophobic region provides an area for dimerization, allowing the motifs to "zip" together. Furthermore, the hydrophobic leucine region is absolutely required for DNA binding. Leucine zippers were originally identified in several DNA-binding proteins (Landschulz et al., Science 240: 1759, 1988), and have since been found in a variety of different proteins. Among the known leucine zippers are naturally occurring peptides and derivatives thereof that dimerize or trimerize.

Examples of zipper domains are those found in the yeast transcription factor GCN4 and a heat-stable DNA-binding protein found in rat liver (C/EBP; Landschulz et al., Science 243:1681, 1989). The nuclear transforming proteins, fos and jun, also exhibit zipper domains, as does the gene product of the murine proto-oncogene, c-myc (Landschulz et al., Science 240:1759, 1988). The fusogenic proteins of several different viruses, including paramyxovirus, coronavirus, measles virus and many retroviruses, also possess zipper domains (Buckland and Wild, Nature 338:547, 1989; Britton, Nature 353:394, 1991; Delwart and Mosialos, AIDS Research and Human Retrovirtises 6:703, 1990). The zipper domains in these fusogenic viral proteins are near the transmembrane region of the protein. Oligomerization of fusogenic viral proteins is involved in fusion pore formation (Spruce et al, Proc. Natl. Acad. Sci. U.S.A. 88:3523, 1991). Zipper domains have also been reported to play a role in oligomerization of heat-shock transcription factors (Rabindran et al., Science 259:230, 1993).

Examples of leucine zipper domains suitable for producing multimodal TRAIL agents include, but are not limited to, those described in PCT application WO 94/10308; U.S. Pat. No. 5,716,805; the leucine zipper derived from lung surfactant protein D (SPD) described in Hoppe et al., 1994, FEBS Letters 344:191; and Fanslow et al., 1994, Semin. Immunol. 6:267-278, the contents of each of which are hereby incorporated by reference in their entireties. In some embodiments of the multimodal TRAIL agents, leucine residues in a leucine zipper domain are replaced by isoleucine residues. Such peptides comprising isoleucine can also be referred to as isoleucine zippers, but are encompassed by the term "leucine zippers" as used herein.

Reporter Modules

The multimodal TRAIL agents described herein are engineered to have at least two functional activities—therapeutic and diagnostic. The therapeutic activity is provided by the therapeutic TRAIL module, which provides the agent the ability to induce apoptosis of target cells and cytotoxicity. The diagnostic activity is provided by the reporter module, which is selected, designed or engineered to permit in vivo monitoring and visualization of the multimodal TRAIL agent. Preferably, the reporter module permits minimally invasive monitoring and visualization of the multimodal TRAIL agent, as described herein.

A "reporter module," as used herein, refers to a molecule which provides an analytically identifiable signal allowing detection of a multimodal TRAIL agent by non-invasive means. Detection can be either qualitative or quantitative. Commonly used reporter modules include, for example, fluorophores, enzymes, biotin, chemiluminescent molecules, bioluminescent molecules, digoxigenin, avidin, streptavidin, or radioisotopes. Commonly used enzymes include, for example, horseradish peroxidase, alkaline phosphatase, glucose oxidase and beta-galactosidase, among others. Enzymes can be conjugated to avidin or streptavidin for use in a reporter module. Similarly, reporter modules can be conjugated to avidin or streptavidin for use with a biotinylated enzyme. The substrates to be used with these enzymes are generally chosen for the production, upon hydrolysis by the corresponding enzyme, of a detectable color change. For example, p-nitrophenyl phosphate is suitable for use with alkaline phosphatase reporter module; for horseradish peroxidase, 1,2-phenylenediamine, 5-aminosalicylic acid or tolidine are commonly used. Incorporation of a reporter module into a sequence encoding a multimodal TRAIL agent can be by any method known to the skilled artisan, for example by nick translation, primer extension, random oligo priming, by 3' or 5' end labeling or by other means (see, for example, Sambrook et al. *Molecular Biology: A laboratory Approach*, Cold Spring Harbor, N.Y. 1989).

In some embodiments of the aspects described herein, the reporter module comprises a variant of luciferase. In some such embodiments, the reporter module comprises an alternative form of *Renilla* luciferase designated RLo (Vesinik et al. Molec Imag Biol 2007, 9:267-77). In other embodiments, the luciferase can be firefly luciferase (FLuc), *Renilla* luciferase (Rluc), or *Gaussia princeps* luciferase (GpLuc). Other variants of luciferase can be used and are known to those skilled in the art (Greer and Szalay Luminesence 2002, 17:43-74). For example, *Arachnocampa* (Diptera) luciferases and uses thereof are taught in US Pub. No. 20110015095. Also, engineered forms of *Renilla* luciferase with greater stability and light emission than the native enzyme can be used (Loening et al., Nature Methods 2007 4:641-3). For example, firefly luciferase that is chemically modified by covalent linking or is a biotinylated fusion protein can provide near-infrared imaging capabilities using bioluminescence resonance energy transfer (BRET) (Branchini et al., Bioconjugate Chem 2010 21:2023-2030).

In other embodiments of the aspects described herein, the reporter module comprises HSV1-TK or its variants or mutants (e.g., HSV1-sr39TK). The two main categories of substrates for TK, uracil nucleoside derivatives labeled with radioactive iodine (e.g., FIAU or radiolabeled 2'-fluoro-2'-deoxyarabinofuranosyl-5-ethyl uracil (FEAU)), and acycloguanosine derivatives labeled with radioactive $^{18}$F-Fluorine (e.g., fluoropenciclovir [FPCV] or 9-(4-[$^{18}$F]-fluoro-3-hydroxymethylbutyl)-guanine [FHBG]), have been investigated in the last few years as reporter probes for imaging HSV1-tk reporter gene expression. These radiolabeled reporter probes are phosphorylated by TK. If HSV1-TK is expressed intracellularly, the phosphorylation of the substrate will trap it in the cell expressing HSV1-TK. When used in non-pharmacological tracer doses, these substrates can serve as positron emission tomography (PET) or single photon emission computed tomography (SPECT) targeted reporter probes by their accumulation in those locations where HSV1-TK is present. Additionally, a mutant version of this gene, HSV1-sr39tk was derived using site-directed mutagenesis to obtain an enzyme (HSV1-sr39TK) more effective at phosphorylating ganciclovir/penciclovir, and also less efficient at phosphorylating thymidine, with consequent gain in imaging signal (Yaghoubi and Gambhir Nat Protoc 2006 1:3069-75; Najjar et al. J Nuc Med 2009 50:409-16; Alauddin et al. Curr Topics Med Chem 2010 10:1617-32; Likar et al. Eur J Nuc Med Mol Imag 2009 36:1273-82; Soghomonyan et al., Nat Protoc 2007 2:416-23, the contents of each of which are herein incorporated by reference in their entireties).

In some embodiments, the reporter module can comprise the Dopamine Type 2 Receptor (D2R) PET reporter module which specifically binds 3-(2'-[18F]fluoroethyl)spiperone (FESP) and is imaged by PET or SPECT (Aung et al., Nucl Med Commun 2005 26:259-68). In other embodiments, the reporter module can comprise a sequence that binds MRI contrast agents (US Pub. No. 20100322861, the contents of which are herein incorporated by reference in their entireties). In other embodiments, the reporter module, can comprise a somatostatin Type 2 receptor (Henze et al., J Nucl Med 2001, 42:1053-6) and Sodium/Iodide Symporter (Terrovitis et al., J Am Coll Cardiol 2008, 52:1652-60), the activity of which may be detected by PET or SPECT. In other embodiments, the reporter module can comprise (green/red) fluorescent protein and variants thereof, like EGFP (enhanced green fluorescent protein), RFP (red fluorescent protein, like DsRed or DsRed2), CFP (cyan fluorescent protein), BFP (blue green fluorescent protein), YFP (yellow fluorescent protein), beta.-galactosidase, or chloramphenicol acetyltransferase, and the like (Ray et al. Semin Nucl Med 2001 31:312-20; Deroose et al. Curr Gene Ther 2009 9:212-38; Nair-Gill et al. Immunol Rev 2008 221:214-28; Holmberg and Ahlgren Diabetologia 2008 51:2148-2154). For example, GFP can be from *Aequorea victoria* (U.S. Pat. No. 5,491,084). A plasmid encoding the GFP of *Aequorea victoria* is available from the ATCC Accession No. 87451. Other mutated forms of this GFP including, but not limited to, pRSGFP, EGFP, RFP/DsRed, and EYFP, BFP, YFP, among others, are commercially available from, inter alia, Clontech Laboratories, Inc. (Palo Alto, Calif.). For example, DsRed2 is also available from Clontech Laboratories, Inc. (Palo Alto, Calif.).

Linker Modules

As described herein, the inventors have further elucidated and determined that increased intramolecular spacing between the reporter and the therapeutic TRAIL modules of a multimodal TRAIL agent is surprisingly critical for the effectiveness of the multifunctional properties of the multimodal TRAIL agents. As described herein, a multimodal TRAIL module comprising a linker domain having the 7 amino acids (EASGGPE; SEQ ID NO: 3), as shown in Example 1 and FIG. 1, resulted in much less reporter module expression and TRAIL functional activity than a multimodal TRAIL module comprising a linker domain having 18 amino acids (GSTGGSGKPGSGEGSTGG; SEQ ID NO: 4). Thus, in some embodiments of the aspects described herein, the multimodal TRAIL agents further comprise a linker domain C-terminal to the reporter module and N-terminal to the therapeutic TRAIL module.

As used herein, a "linker module" refers to a peptide, or a nucleotide sequence encoding such a peptide, of at least 8 amino acids in length. In some embodiments of the aspects described herein, the linker module comprises at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 30 amino acids, at least 35 amino acids, at least 40 amino acids, at least 45 amino acids, at least 50 amino acids, at least 55 amino acids, at least 56 amino acids, at least 60 amino acids, or least 65 amino acids. In some embodiments of the aspects described herein, a linker module comprises a peptide of 18 amino acids in length. In some embodiments of the aspects described herein, a linker module comprises a peptide of at least 8 amino acids in length but less than or equal to 56 amino acids in length, i.e., the length of the spacer sequence in the native TRAIL molecule of SEQ ID NO: 1. In some embodiments, the linker molecule comprises the spacer sequence of human TRAIL, i.e., amino acids 39-94 of SEQ ID NO: 1, or a sequence having at least 80%, at least 85%, at least 90%, at least 95%, at least 99% identity to amino acids 39-94 of SEQ ID NO: 1.

In some embodiments of the aspects described herein, a linker module comprises an amino acid sequence of SEQ ID NO: 4. In some embodiments of the aspects described herein, a linker module consists essentially of an amino acid sequence of SEQ ID NO: 4. In some embodiments of the aspects described herein, a linker module consists of an amino acid sequence of SEQ ID NO: 4.

Modes of Direct Administration

The multimodal TRAIL agents described herein can be administered directly as a pharmaceutical composition to a subject in need thereof by any appropriate route which results in an effective treatment in the subject. As used herein, the terms "administering," and "introducing" are used interchangeably and refer to the placement of a multimodal TRAIL agent into a subject by a method or route which results in at least partial localization of such agents at a desired site, such as a cancerous or tumor site or a tumor resection site, such that a desired effect(s) is produced.

In some embodiments of the methods described herein, the multimodal TRAIL agent is administered to a subject in need thereof by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the multimodal TRAIL agents for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the multimodal TRAIL agent other than directly into a target site, tissue, or organ, such as a tumor site, such that it enters the subject's circulatory system and, thus, is subject to metabolism and other like processes.

For the clinical use of the methods described herein, administration of the multimodal TRAIL agents can include formulation into pharmaceutical compositions or pharmaceutical formulations for parenteral administration, e.g., intravenous; mucosal, e.g., intranasal; ocular, or other mode of administration. In some embodiments of the methods, the multimodal TRAIL agents described herein can be administered along with any pharmaceutically acceptable carrier compound, material, or composition which results in an effective treatment in the subject. Thus, a pharmaceutical formulation for use in the methods described herein can comprise a multimodal TRAIL agent as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, a multimodal TRAIL agent. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The multimodal TRAIL agents described herein can be specially formulated for administration to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a multimodal TRAIL agent can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

Some further embodiments of the formulations and modes of direct administration of the multimodal TRAIL agents that can be used in the methods described herein are illustrated below.

Parenteral Dosage Forms.

Parenteral dosage forms of the multimodal TRAIL agents can also be administered to a subject in need thereof, such as a cancer patient, by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Controlled and Delayed Release Dosage Forms.

In some embodiments of the aspects described herein, a multimodal TRAIL agent can be administered to a subject by controlled- or delayed-release means. Ideally, the use of an optimally designed controlled-release preparation in medical treatment is characterized by a minimum of drug/agent substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a multimodal TRAIL agent's onset of action, duration of action, plasma levels within the therapeutic window, and peak blood levels. In particular, controlled- or extended-release dosage forms or formulations can be used to ensure that the maximum effectiveness of a multimodal TRAIL agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the multimodal TRAIL agents described herein. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed agents and thus effect controlled delivery of the drug. Examples of specific anion exchangers include, but are not limited to, Duolite® A568 and Duolite® AP143 (Rohm&Haas, Spring House, Pa. USA).

In some embodiments, a multimodal TRAIL agent for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are preferred when the disorder occurs continuously in the subject, for example where the subject has a chronic disorder such as cancer. Each pulse dose can be reduced and the total amount of a multimodal TRAIL agent administered over the course of treatment to the patient is minimized.

The interval between pulses, when necessary, can be determined by one of ordinary skill in the art. Often, the interval between pulses can be calculated by administering another dose of a composition comprising a multimodal TRAIL agent when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Vectors and Genetic Engineering

Gene therapy or transgene compositions and methods thereof are also contemplated for use with the multimodal TRAIL agents described herein. Such methods allow clinicians to introduce a nucleic acid sequence encoding a multimodal TRAIL agent or component thereof of interest directly into a patient (in vivo gene therapy) or into cells isolated from a patient or a donor (ex vivo gene therapy). Therapeutic multimodal TRAIL agents produced by transduced cells after gene therapy can be maintained at a relatively constant level in, for example, the CNS of a subject, as compared to a protein that is administered directly. Such sustained production of a multimodal TRAIL agent is particularly appropriate in the treatment of chronic diseases, such as cancers. Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292).

Further, regulatable genetic constructs using small molecule inducers have been developed that can be included in vectors to be used in some embodiments of the aspects described herein. (Rivera et al. (1996) Nat. Med. 2:1028-32; No et al. (1996) Proc. Natl. Acad. Sci. USA, 93:3346-51; Gossen and Bujard (1992) Proc. Natl. Acad. Sci. USA 89:5547-51; the GeneSwitch® system (Valentis, Inc., Burlingame, Calif.)). These systems are based on the use of engineered transcription factors the activity of which is controlled by a small molecule drug, and a transgene, the expression of which is driven by the regulated transcription factor (Rivera et al. (1996) Nat. Med. 2:1028-32; Pollock et al. (2000) Proc. Natl. Acad. Sci. USA 97:13221-26; U.S. Pat. Nos. 6,043,082 and 6,649,595; Rivera et al. (1999) Proc. Natl. Acad. Sci. USA 96:8657-62).

In some of the aspects described herein, a nucleic acid sequence encoding a multimodal TRAIL agent, or any module thereof, is operably linked to a vector. In general, as used herein, the term "vector" refers to any genetic element, such as a plasmid, phage, transposon, cosmid, chromosome, virus, virion, etc., that is capable of replication when associated with the proper control elements and that can transfer gene sequences to cells. Thus, the term includes cloning and expression vehicles, as well as viral vectors. By "recombinant vector" is meant a vector that includes a heterologous nucleic acid sequence, or "transgene" that is capable of expression in vivo. It should be understood that the vectors described herein can, in some embodiments, be combined with other suitable compositions and therapies. Vectors useful for the delivery of a sequence encoding a multimodal TRAIL agent or component thereof can include one or more regulatory elements (e.g., promoter, enhancer, etc.) sufficient for expression of the multimodal TRAIL agent or component thereof in the desired target cell or tissue. The regulatory elements can be chosen to provide either constitutive or regulated/inducible expression.

Plasmid-Directed Delivery

A nucleic acid sequence encoding a multimodal TRAIL agent or any module thereof, can, in some embodiments, be delivered using non-viral, plasmid-based nucleic acid delivery systems, as described in U.S. Pat. Nos. 6,413,942, 6,214,804, 5,580,859, 5,589,466, 5,763,270 and 5,693,622, all of which are incorporated herein by reference in their entireties. Such plasmids comprise the sequence encoding the multimodal TRAIL agent, or a component thereof, operably linked to control elements that direct the expression of the multimodal TRAIL agent in a target cell, and are well known to those of ordinary skill in the art.

In some embodiments, plasmid vectors comprising nucleic acid sequence(s) encoding a multimodal TRAIL agent or any module thereof can be packaged in liposomes prior to delivery to a subject or to cells, as described in U.S. Pat. Nos. 5,580,859, 5,549,127, 5,264,618, 5,703,055, all incorporated herein by reference in their entireties. For a review of the use of liposomes as carriers for delivery of nucleic acids, see, Hug and Sleight (1991) Biochim. Biophys. Acta. 1097:1-17; Straubinger et al. (1983) in Methods of Enzymology Vol. 101, pp. 512-27; de Lima et al. (2003) Current Medicinal Chemistry, Volume 10(14): 1221-31. The DNA can also be delivered in cochleate lipid compositions similar to those described by Papahadjopoulos et al. (1975) Biochem. Biophys. Acta. 394:483-491. See also U.S. Pat. Nos. 4,663,161 and 4,871,488, incorporated herein by reference in their entireties.

Biolistic delivery systems employing particulate carriers such as gold and tungsten can also be used to deliver nucleic acid sequence encoding a multimodal TRAIL agent, or any module thereof. See, e.g., U.S. Pat. Nos. 4,945,050, 5,036, 006, 5,100,792, 5,179,022, 5,371,015, and 5,478,744, all incorporated herein by reference in their entireties.

A wide variety of other methods can be used to deliver the vectors comprising nucleic acid sequence(s) encoding a multimodal TRAIL agent or any module thereof. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, peptoid delivery, or microinjection. See, e.g., Sambrook et al (1989) Molecular Cloning, A Laboratory Manual, Cold Spring Harbor Laboratories, New York, for a discussion of techniques for transforming cells of interest; and Felgner, P. L. (1990) Advanced Drug Delivery Reviews 5:163-87, for a review of delivery systems useful for gene transfer. Exemplary methods of delivering DNA using electroporation are described in U.S. Pat. Nos. 6,132,419; 6,451, 002, 6,418,341, 6,233,483, U.S. Patent Publication No. 2002/0146831, and International Publication No. WO/0045823, all of which are incorporated herein by reference in their entireties.

In other embodiments of the aspects described herein, plasmid vectors comprising nucleic acid sequence(s) encoding a multimodal TRAIL agent or any module thereof can also be introduced directly into the CNS by intrathecal (IT) injection, as described herein in greater detail with regard to protein administration. Plasmid DNA can be complexed with cationic agents such as polyethyleneimine (PEI) or Lipofectamine 2000 to facilitate uptake.

Retroviral Delivery

Retroviruses, such as lentiviruses, provide another convenient platform for delivery of nucleic acid sequences encoding a multimodal TRAIL agent of interest. A selected nucleic acid sequence can be inserted into a vector and packaged in retroviral particles using techniques known in the art. These retroviral vectors contain the components necessary for the correct packaging of the viral genome and integration into the host cell DNA. The recombinant virus can then be isolated and delivered to cells of the subject either in vivo or ex vivo. The nucleic acid sequences encoding a multimodal TRAIL agent or module thereof are cloned into one or more vectors, which facilitates delivery of the nucleic acid into a patient. Retroviral systems are described in, for example, U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Miller et al., Meth. Enzymol. 217: 581-599 (1993); Burns et al. (1993) Proc. Natl. Acad. Sci. USA 90:8033-37; Boris-Lawrie and Temin (1993) Curr. Opin. Genet. Develop. 3:102-09. Greater detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy include: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993), the contents of each of which are herein incorporated by reference in their entireties.

In some embodiments of the aspects described herein, a lentiviral system is used to deliver a nucleic acid sequence encoding a multimodal TRAIL agent of interest. Lentiviral vectors contemplated for use include, for example, the HIV based vectors described in U.S. Pat. Nos. 6,143,520; 5,665,557; and 5,981,276, the contents of which are herein incorporated by reference in their entireties.

Adenoviral Delivery

In some embodiments, a nucleotide sequence encoding a multimodal TRAIL agent of interest or module thereof is inserted into an adenovirus-based expression vector Unlike retroviruses, which integrate into the host genome, adenoviruses persist extrachromosomally thus minimizing the risks associated with insertional mutagenesis (Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76). Adenoviral vectors have several advantages in gene therapy. They infect a wide variety of cells, have a broad host-range, exhibit high efficiencies of infectivity, direct expression of heterologous sequences at high levels, and achieve long-term expression of those sequences in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. For all these reasons vectors derived from human adenoviruses, in which at least the E1 region has been deleted and replaced by a gene of interest, have been used extensively for gene therapy experiments in the pre-clinical and clinical phase.

Adenoviral vectors for use with the compositions and methods described herein can be derived from any of the various adenoviral serotypes, including, without limitation, any of the over 40 serotype strains of adenovirus, such as serotypes 2, 5, 12, 40, and 41. The adenoviral vectors used herein are replication-deficient and contain the sequence of interest under the control of a suitable promoter, such as any of the promoters discussed below with reference to adeno-associated virus. For example, U.S. Pat. No. 6,048,551, incorporated herein by reference in its entirety, describes replication-deficient adenoviral vectors that include a human gene under the control of the Rous Sarcoma Virus (RSV) promoter. Other recombinant adenoviruses of various serotypes, and comprising different promoter systems, can be created by those skilled in the art. See, e.g., U.S. Pat. No. 6,306,652, incorporated herein by reference in its entirety.

Other useful adenovirus-based vectors for delivery of nucleic acid sequence encoding a multimodal TRAIL agent of interest or module thereof include, but are not limited to: "minimal" adenovirus vectors as described in U.S. Pat. No. 6,306,652, which retain at least a portion of the viral genome required for encapsidation (the encapsidation signal), as well as at least one copy of at least a functional part or a derivative of the ITR; and the "gutless" (helper-dependent) adenovirus in which the vast majority of the viral genome has been removed and which produce essentially no viral proteins, thus allowing gene therapy to persist for over a year after a single administration (Wu et al. (2001) Anesthes. 94:1119-32; Parks (2000) Clin. Genet. 58:1-11; Tsai et al. (2000) Curr. Opin. Mol. Ther. 2:515-23).

Adeno Associated Virus (AAV) Delivery

In some embodiments of the compositions and methods described herein, a nucleotide sequence encoding a multimodal TRAIL agent of interest is inserted into an adeno-associated virus-based expression vector. AAV is a parvovirus which belongs to the genus *Dependovirus* and has several features not found in other viruses. AAV can infect a wide range of host cells, including non-dividing cells. AAV can infect cells from different species. AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions, facilitating production, storage and transportation.

AAV is a helper-dependent virus; that is, it requires co-infection with a helper virus (e.g., adenovirus, herpesvirus or vaccinia) in order to form AAV virions in the wild. In the absence of co-infection with a helper virus, AAV establishes a latent state in which the viral genome inserts into a host cell chromosome, but infectious virions are not produced. Subsequent infection by a helper virus rescues the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

Adeno-associated virus (AAV) has been used with success in gene therapy. AAV has been engineered to deliver genes of interest by deleting the internal nonrepeating portion of the AAV genome (i.e., the rep and cap genes) and inserting a heterologous sequence (in this case, the sequence encoding the multimodal TRAIL agent) between the ITRs. The heterologous sequence is typically functionally linked to a heterologous promoter (constitutive, cell-specific, or inducible) capable of driving expression in the patient's target cells under appropriate conditions.

Recombinant AAV virions comprising a nucleic acid sequence encoding a multimodal TRAIL agent of interest can be produced using a variety of art-recognized techniques, as described in U.S. Pat. Nos. 5,139,941; 5,622,856;

5,139,941; 6,001,650; and 6,004,797, the contents of each of which are incorporated by reference herein in their entireties. Vectors and cell lines necessary for preparing helper virus-free rAAV stocks are commercially available as the AAV Helper-Free System (Catalog No. 240071) (Stratagene, La Jolla, Calif.).

Other Viral Vectors for Delivery

Additional viral vectors useful for delivering nucleic acid molecules encoding a multimodal TRAIL agent of interest include those derived from the pox family of viruses, including vaccinia virus and avian poxvirus. Alternatively, avipoxviruses, such as the fowlpox and canarypox viruses, can be used to deliver the genes. The use of avipox vectors in human and other mammalian species is advantageous with regard to safety because members of the avipox genus can only productively replicate in susceptible avian species. Methods for producing recombinant avipoxviruses are known in the art and employ genetic recombination, see, e.g., WO 91/12882; WO 89/03429; and WO 92/03545.

Molecular conjugate vectors, such as the adenovirus chimeric vectors, can also be used for delivery of sequence encoding a multimodal TRAIL agent or component thereof (Michael et al. (1993) J. Biol. Chem. 268:6866-69 and Wagner et al. (1992) Proc. Natl. Acad. Sci. USA 89:6099-6103). Members of the *Alphavirus* genus, for example the Sindbis and Semliki Forest viruses, can also be used as viral vectors for delivering a nucleic acid sequence encoding a multimodal TRAIL agent of interest (See, e.g., Dubensky et al. (1996) J. Virol. 70:508-19; WO 95/07995; WO 96/17072).

Cell Types

Essentially any cell type can be engineered with a sequence encoding the multimodal TRAIL agents, as described herein, for use in cellular therapies. Thus, differentiated somatic cells and stem cells, as well as cells of a cell line, can be engineered to express, using any method known to one of skill in the art, a desired multimodal TRAIL agent. In some embodiments of the aspects described herein, a cell can be transduced with a delivery vector comprising a nucleic acid sequence encoding a multimodal TRAIL agent or module thereof. In other embodiments of the compositions and methods described herein, a cell can be transfected with a nucleic acid sequence encoding a multimodal TRAIL agent. Provided herein are exemplary stem cells, somatic cells, and cell line sources useful with the methods and compositions described herein. However, the description herein is not meant to be limiting and any cell known or used in the art can be genetically modified or engineered to express and secrete a multimodal TRAIL agent. In some embodiments, the cells to be engineered can be from an autologous, i.e., from the same subject, or from one or more heterologous sources.

Stem Cells

Stem cells are undifferentiated cells defined by their ability at the single cell level to both self-renew and differentiate to produce progeny cells, including self-renewing progenitors, non-renewing progenitors, and terminally differentiated cells. Stem cells, depending on their level of differentiation, are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. (See, e.g., Potten et al., Development 110: 1001 (1990); U.S. Pat. Nos. 5,750,376, 5,851,832, 5,753, 506, 5,589,376, 5,824,489, 5,654,183, 5,693,482, 5,672,499, and 5,849,553, all herein incorporated in their entireties by reference).

The stem cells for use with the compositions and methods comprising multimodal TRAIL agents described herein can be naturally occurring stem cells or "induced" stem cells, such as "induced pluripotent stem cells" (iPS cells) generated using any method or composition known to one of skill in the art. Stem cells can be obtained or generated from any mammalian species, e.g. human, primate, equine, bovine, porcine, canine, feline, rodent, e.g. mice, rats, hamster, etc. In some embodiments of the aspects described herein, a stem cell is a human stem cell.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and the cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Stem cells of interest for use in the compositions and methods described herein include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Cells derived from embryonic sources can include embryonic stem cells or stem cell lines obtained from a stem cell bank or other recognized depository institution.

In some embodiments of the aspects described herein, a cell engineered to express or secrete a multimodal TRAIL agent is an adult or somatic stem cell. Adult stem cells are generally limited to differentiating into different cell types of their tissue of origin. However, if the starting stem cells are derived from the inner cell mass of the embryo, they can generate many cell types of the body derived from all three embryonic cell types: endoderm, mesoderm and ectoderm. Stem cells with this property are said to be "pluripotent." Embryonic stem cells are one kind of pluripotent stem cell. Thus, pluripotent embryonic stem cells can be differentiated into many specific cell types. Since the embryo is a potential source of all types of precursor cells, it is possible to differentiate, for example, engineered embryonic stem cells into other lineages by providing the appropriate signals, such as the expression of proteins, using any method known to one of skill in the art, to embryonic stem cells.

Somatic or adult stem cells have major advantages, for example, as using somatic stem cells allows a patient's own cells to be expanded in culture and then re-introduced into the patient. Natural somatic stem cells have been isolated from a wide variety of adult tissues including blood, bone marrow, brain, olfactory epithelium, skin, pancreas, skeletal muscle, and cardiac muscle. Each of these somatic stem cells can be characterized based on gene expression, factor responsiveness, and morphology in culture. Exemplary naturally occurring somatic stem cells include, but are not limited to, neural stem cells, neural crest stem cells, mesenchymal stem cells, hematopoietic stem cells, and pancreatic stem cells. In addition, iPS cells generated from a patient provide a source of cells that can be engineered to express a multimodal TRAIL agent, expanded, and re-introduced to the patient, before or after stimulation to differentiate to a desired lineage or phenotype, such as a neural stem cell. In some embodiments of the aspects described herein, a somatic stem cell engineered to express a multimodal TRAIL agent is a neural stem cell. In some embodiments of the aspects described herein, a somatic stem cell engineered to express a multimodal TRAIL agent is a mesenchymal stem cell. In some embodiments of the aspects described herein, a somatic stem cell engineered to express a multimodal TRAIL agent is an iPS cell differentiated into a neural stem cell. In some embodiments of the aspects described herein, a somatic stem cell engineered to express a multimodal TRAIL agent is an iPS cell differentiated into a mesenchymal stem cell.

Cord blood cells are used as a source of transplantable stem and progenitor cells and as a source of marrow repopulating cells for the treatment of malignant diseases (e.g, acute lymphoid leukemia, acute myeloid leukemia, chronic myeloid leukemia, myelodysplastic syndrome, and neuroblastoma) and non-malignant diseases such as Fanconi's anemia and aplastic anemia (Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503). Accordingly, in some aspects, cells to be engineered to secrete or express a multimodal TRAIL agent can also be derived from human umbilical cord blood cells (HUCBC), which are recognized as a rich source of hematopoietic and mesenchymal stem cells (Broxmeyer et al., 1992 Proc. Natl. Acad. Sci. USA 89:4109-4113). One advantage of HUCBC for use with the methods and compositions described herein is the immature immunity of these cells, which is very similar to fetal cells, and thus significantly reduces the risk for rejection by the host (Taylor & Bryson, 1985 J. Immunol. 134:1493-1497).

In some embodiments of the aspects described herein, iPS cells are engineered to express or secrete the multimodal TRAIL agents described herein. In some embodiments of the aspects described herein, iPS cells are engineered to express or secrete the multimodal TRAIL agents prior to being differentiated into another desired cell type. In some embodiments of the aspects described herein, iPS cells are engineered to express or secrete the multimodal TRAIL agents after differentiation into another desired cell type.

In other embodiments of the aspects described herein, cancer stem cells can be engineered to express or secrete the multimodal TRAIL agents described herein. It has been recently discovered that stem-like cells are present in some human tumors and, while representing a small minority of the total cellular mass of the tumor, are the subpopulation of tumor cells responsible for growth of the tumor. In contrast to normal stem cells, "tumor stem cells" or "cancer stem cells" are defined as cells that can undergo self-renewal, as well as abnormal proliferation and differentiation to form a tumor. Functional features of tumor stem cells are that they are tumorigenic; they can give rise to additional tumorigenic cells by self-renewal; and they can give rise to non-tumorigenic tumor cells. The developmental origin of tumor stem cells can vary among different types of cancers. It is believed, without wishing to be bound or limited by theory, that tumor stem cells can arise either as a result of genetic damage that deregulates normal mechanisms of proliferation and differentiation of stem cells (Lapidot et al., Nature 367(6464): 645-8 (1994)), or by the dysregulated proliferation of populations of cells that acquire stem-like properties.

Neural Stem Cells

Recent studies have shown that intracranially or intravenously injected neural stem cells (NSCs) or neural precursor cells migrate towards injured or pathological central nervous system (CNS) sites. This chemotropic property of NSCs has been utilized for cell-based therapies to treat diverse neurological diseases as described herein and in T. Bagci-Onder et al., Cancer Research 2011, 71:154-163; Hingtgen S. et al., Stem Cells 2010, 28(4):832-41; Hingtgen S. et al., Mol Cancer Ther. 2008, 7(11): 3575-85; Brustle O. et al., 6 Current Opinion in Neurobiology. 688 (1996); Flax J. D., et al., 16 Nature Biotechnology. 1033. (1998); Kim S. U., 24. Neuropathology. 159 (2004); Lindvall O et al., 10 (suppl) Nature Medicine. S42 (2004); Goldman S., 7. Nature Biotechnology. 862 (2005); Muller F. et al., 7 Nature Reviews Neuroscience. 75 (2006); Lee, J. P., et al. 13 Nature Medicine 439 (2007), and Kim S. U. et al., 87 Journal of Neuroscience Research 2183 (2009), the contents of each of which are herein incorporated in their entireties by reference.

Administration of delivery vectors can be performed intracranially or extracranially using known techniques. Stem cells, such as neural stem cells, have been shown to cross the blood-brain barrier and home towards injury in brain. Thus, for example stem cells engineered to produce the secreted multimodal TRAIL agents described herein can be administered intravenously and are expected to reach desired areas of the brain, such as the site of a glioblastoma. Further, and importantly from a diagnostic aspect, as the multimodal TRAIL agents comprise a reporter module, delivery of the cells and agents to a desired area can be visualized.

Accordingly, in some embodiments of the compositions and methods described herein, a pharmaceutically acceptable composition comprising a neural stem cell and a multimodal TRAIL agent can be administered to a subject. In some such embodiments, the neural stem cell is genetically engineered to express or secrete a multimodal TRAIL agent. Because NSCs can be engineered to package and release replication-defective retroviral particles or replication-conditional herpes virus vectors which, in turn, can serve as vectors for the transfer of sequences to CNS cells, neural progenitor/stem cells can serve to magnify the efficacy of viral-mediated gene delivery to large regions in the brain. In some such embodiments, the neural stem cell can comprise a vector encoding a multimodal TRAIL agent. Additional vectors that can be used in the embodiments described herein include herpes simplex virus vectors, SV 40 vectors, polyoma virus vectors, papilloma virus vectors, picarnovirus vectors, vaccinia virus vectors, and a helper-dependent or gutless adenovirus. In one embodiment, the vector can be a lentivirus. Methods for preparing genetically engineered neural stem cells and compositions thereof for therapeutic treatment have been described in U.S. Pat. No. 7,393,526 and U.S. Pat. No. 7,655,224, the contents of which are incorporated herein by reference in their entirety.

In various embodiments of the compositions and methods described herein, the neural stem cells that can be used include, but are not limited to, human neural stem cells, mouse neural stem cells HSN-1 cells, fetal pig cells and neural crest cells, bone marrow derived neural stem cells, and hNT cells. HSN-1 cells can be prepared, for example, as described in, e.g., Ronnett et al. (Science 248, 603-605, 1990). The preparation of neural crest cells in described in U.S. Pat. No. 5,654,183. hNT cells can be prepared as described in, e.g, Konubu et al. (Cell Transplant 7, 549-558, 1998). In some embodiments of the compositions and methods described herein, the neural stem cells that can be used are neural stem cells derived or differentiated from a precursor stem cell, such as a human embryonic stem cell or an induced pluripotent stem (iPS) cell. Such neural stem cells can be generated from or differentiated from human embryonic stem cells, using, for example, compositions and methods described in Nature Biotechnology 27, 275-280 (2009), "Highly efficient neural conversion of human ES and iPS cells by dual inhibition of SMAD signaling," the contents of which are herein incorporated by reference in their entireties. Such neural stem cells can be generated from or differentiated from iPS cells, using, for example, the compositions and methods described in US Patent Publication US 2010/0021437 A1, "NEURAL STEM CELLS DERIVED FROM INDUCED PLURIPOTENT STEM CELLS," the contents of which are herein incorporated by reference in their entireties.

Accordingly, as used herein, "neural stem cells" refers to a subset of pluripotent cells which have partially differentiated along a neural cell pathway and express some neural markers including, for example, nestin. Neural stem cells can differentiate into neurons or glial cells (e.g., astrocytes and oligodendrocytes). Thus, "neural stem cells derived or differentiated from iPS cells" refers to cells that are pluripotent but have partially differentiated along a neural cell pathway (i.e., express some neural cell markers), and themselves are the result of in vitro or in vivo differentiation iPS cells.

Neural selection factors that can be used to differentiate pluripotent stem cells, such as embryonic stem cells or iPS cells into neural stem cells, include, for example, sonic hedgehog (SHH), fibroblast growth factor-2 (FGF-2), and fibroblast growth factor-8 (FGF-8), which can be used alone or in pairwise combination, or all three factors may be used together. In some embodiments, iPS cells are cultured in the presence of at least SHH and FGF-8. In other embodiments, FGF-2 is omitted. Preferably, the neural stem cells derived from iPS cells express nestin. In some embodiments, the pluripotent stem cells are cultured in the presence of the one or more neural selection factors for 4, 5, 6, 7, 8, 9, 10, 12, 14, 16, 18, 20 days or more. Preferably, the population of neural stem cells is characterized in that at least 50%, at least 75%, at least 85%, at least 90%, at least 95%, or at least 99% of the cells of the population expresses nestin. Preferably, the nestin-expressing cells further express at least one of En-1, Pitx3, and Nurr-1. In other embodiments, the population of neural stem cells has been depleted of at least 50%, 75%, 85%, 95%, or 99% of the cells expressing surface markers of immature embryonic stem cells including, for example, SSEA-1, SSEA-3, SSEA-4, Tra-1-81, and Tra-1-60. Preferably, the population of neural stem cells contains less than 10%, less than 5%, less than 2.5%, less than 1%, or less than 0.1% of cells that express the selected marker (e.g., SSEA-4).

Somatic Cells

In some embodiments, the cells engineered to express or secrete the multimodal TRAIL agents described herein are primary somatic cells. Some non-limiting examples of primary cells include, but are not limited to, fibroblast, epithelial, endothelial, neuronal, adipose, cardiac, skeletal muscle, immune cells, hepatic, splenic, lung, circulating blood cells, gastrointestinal, renal, bone marrow, and pancreatic cells. The cell can be a primary cell isolated from any somatic tissue including, but not limited to, brain, liver, lung, gut, stomach, intestine, fat, muscle, uterus, skin, spleen, endocrine organ, bone, etc. The term "somatic cell" further encompasses primary cells grown in culture, provided that the somatic cells are not immortalized.

Cell Lines

In some embodiments, the cells engineered to express or secrete the multimodal TRAIL agents described herein described herein comprise cells of a cell line.

Exemplary human cell lines include, but are not limited to, 293T (embryonic kidney), BT-549 (breast), DMS 114 (small cell lung), DU145 (prostate), HT-1080 (fibrosarcoma), HEK 293 (embryonic kidney), HeLa (cervical carcinoma), HepG2 (hepatocellular carcinoma), HL-60(TB) (leukemia), HS 578T (breast), HT-29 (colon adenocarcinoma), Jurkat (T lymphocyte), M14 (melanoma), MCF7 (mammary), MDA-MB-453 (mammary epithelial), PERC6® (E1-transformed embryonal retina), RXF 393 (renal), SF-268 (CNS), SF-295 (CNS), THP-1 (monocyte-derived macrophages), TK-10 (renal), U293 (kidney), UACC-257 (melanoma), and XF 498 (CNS).

Examples of non-human primate cell lines useful in the compositions and methods provided herein include, but are not limited to, monkey kidney (CVI-76) cells, African green monkey kidney (VERO-76) cells, green monkey fibroblast (Cos-1) cells, and monkey kidney (CVI) cells transformed by SV40 (Cos-7). Additional mammalian cell lines are known to those of ordinary skill in the art and are catalogued at the American Type Culture Collection catalog (ATCC®, Mamassas, Va.).

Examples of rodent cell lines useful in the compositions and methods provided herein include, but are not limited to, mouse Sertoli (TM4) cells, mouse mammary tumor (MMT) cells, rat hepatoma (HTC) cells, mouse myeloma (NS0) cells, murine hybridoma (Sp2/0) cells, mouse thymoma (EL4) cells, Chinese Hamster Ovary (CHO) cells and CHO cell derivatives, murine embryonic (NIH/3T3, 3T3 L1) cells, rat myocardial (H9c2) cells, mouse myoblast (C2C12) cells, and mouse kidney (miMCD-3) cells.

Cellular Therapies and Cellular Administration

The compositions and methods comprising multimodal TRAIL agents are particularly useful in patients in need of cellular therapies. Accordingly, various aspects and embodiments of the methods and compositions described herein involve administration of an effective amount of a cell or a population of cells, generated using any of the compositions comprising a multimodal TRAIL agent described herein, or engineered to express a multimodal TRAIL agent as described herein, to an individual or subject in need of a cellular therapy. The cell or population of cells being administered can be an autologous population, or be derived from one or more heterologous sources. The cell can be, for example, a stem cell, such as a lineage-restricted progenitor cell, multipotent cell, or an oligopotent cell, or a fully or partially differentiated progeny of a stem cell. In some embodiments, cells engineered to secrete a multimodal TRAIL agent can be introduced via a scaffold or encapsulated in a biodegradable extracellular matrix to enhance retention and release of secreted multimodal TRAIL agents in a subject in need thereof.

A variety of means for administering cells to subjects are known to those of skill in the art. Such methods can include systemic injection, for example, i.v. injection, or implantation of cells into a target site in a subject, such as a surgical site. Cells can be inserted into a delivery device which facilitates introduction by injection or implantation into the subject. Such delivery devices can include tubes, e.g., catheters, for injecting cells and fluids into the body of a recipient subject. In some embodiments, the tubes additionally have a needle, e.g., through which the cells can be introduced into the subject at a desired location. The cells can be prepared for delivery in a variety of different forms. For example, cells can be suspended in a solution or gel or embedded in a support matrix when contained in such a delivery device. Cells can be mixed with a pharmaceutically acceptable carrier or diluent in which the cells remain viable.

Pharmaceutically acceptable carriers and diluents include saline, aqueous buffer solutions, solvents and/or dispersion media. The use of such carriers and diluents is well known in the art. The solution is preferably sterile and fluid. Preferably, prior to the introduction of cells as described herein, the solution is stable under the conditions of manufacture and storage and preserved against the contaminating action of microorganisms such as bacteria and fungi through the use of agents such as parabens, chlorobutanol, phenol, ascorbic acid, thimerosal, and the like.

It is preferred that the mode of cell administration is relatively non-invasive, for example by intravenous injection, pulmonary delivery through inhalation, topical, or intranasal administration. However, the route of cell administration will depend on the tissue to be treated and can include implantation. Methods for cell delivery are known to those of skill in the art and can be extrapolated by one skilled in the art of medicine for use with the methods and compositions described herein.

In some embodiments of the methods described herein, a cell or population of cells engineered to express a multimodal TRAIL agent is directly placed or administered to a surgical site, such as a surgical resection site. By placing the cell or population of cells engineered to express a multimodal TRAIL agent at a surgical site, enhanced clearance of the target cancer cells can be achieved, as demonstrated herein. Such direct administration to a surgical site can include administration of a suspension of engineered cells, or encapsulation of engineered cells at the surgical site, such as, as described herein in Example 2.

In some embodiments of the methods described herein, a cell or population of cells engineered to express a multimodal TRAIL are administered to a surgical site or lesion (e.g., cancer) site by intraparenchymal (e.g., intracerebral) grafting of the cell or cell populations into the surgical or lesioned region. The cells engineered to express a multimodal TRAIL can be delivered to a specific site by stereotaxic injection. Conventional techniques for grafting are described, for example, in Bjorklund et al. (Neural Grafting in the Mammalian CNS, eds. Elsevier, pp 169-178, 1985), Leksell et al. (Acta Neurochir., 52:1-7, 1980) and Leksedl et al. (J. Neurosturg., 66:626-629, 1987).

In some embodiments, administration of engineered cells into selected regions of a patient's brain can be made by drilling a hole and piercing the dura to permit the needle of a microsyringe to be inserted. Alternatively, in other embodiments, the cells can be injected into the brain ventricles or intrathecally into a spinal cord region.

Direct injection techniques for cell administration can also be used to stimulate transmigration of cells through the entire vasculature, or to the vasculature of a particular organ, such as for example liver, or kidney or any other organ. This includes non-specific targeting of the vasculature. One can target any organ by selecting a specific injection site, e.g., a liver portal vein. Alternatively, the injection can be performed systemically into any vein in the body. In another example, compositions comprising neural stem cells or precursor cells engineered to secrete a multimodal TRAIL agent can be transplanted directly into parenchymal or intrathecal sites of the central nervous system, according to the disease being treated, such as for example, the site of a glioblastoma. Grafts can be done using single cell suspensions or small aggregates at a density of 25,000-500,000 cells per mL (U.S. Pat. No. 5,968,829, the contents of which are herein incorporated in their entireties by reference).

If so desired, a mammal or subject can be pre-treated with an agent, for example an agent is administered to enhance cell targeting to a tissue (e.g., a homing factor) and can be placed at that site to encourage cells to target the desired tissue. For example, direct injection of homing factors into a tissue can be performed prior to systemic delivery of ligand-targeted cells.

Scaffolds and Encapsulation of Cells

It is further contemplated that, in some embodiments of these aspects, cells engineered to express the multimodal TRAIL agents described herein, can not only be administered to a subject in need as cells in suspension, but also as cells populating a matrix, scaffold, or other support, to enhance retention of cells and delivery of the multimodal TRAIL agents at a site. Encapsulation of stem cells has shown to permit enhanced delivery of engineered stem cells, as described in, for example, Compte M. et al., Stem Cells 2009, 27(3):753-760, the contents of which are herein incorporated in their entireties by reference, and as demonstrated herein in the Examples (see, for example, FIGS. 13A-13G, and 17A-17L).

In some embodiments, a "support" refers to any suitable carrier material to which cells, such as engineered neural stem cells expressing a multimodal TRAIL agent described herein, are able to attach themselves or adhere, and can be used in order to form a corresponding cell composite, e.g. an artificial tissue. In some embodiments, a matrix or carrier material, respectively, is present already in a three-dimensional form desired for later application.

In some such embodiments, a matrix or a scaffold comprises a "biocompatible substrate" that can be used as a material that is suitable for implantation into a subject onto which a cell population can be deposited. A biocompatible substrate does not cause toxic or injurious effects once implanted in the subject. The biocompatible substrate can provide the supportive framework that allows cells to attach to it, and grow on it. Cultured populations of cells can then be grown on the biocompatible substrate, which provides the appropriate interstitial distances required for cell-cell interaction.

A matrix, structure, or scaffold can be used to aid in further controlling and directing a cell or population of cells expressing or secreting a multimodal TRAIL agent described herein. A matrix or scaffold can be designed or selected to provide environmental cues to control and direct the migration of cells to a site of injury or disease. A structure or scaffold can be engineered from a nanometer to micrometer to millimeter to macroscopic length, and can further comprise or be based on factors such as, but not limited to, material mechanical properties, material solubility, spatial patterning of bioactive compounds, spatial patterning of topological features, soluble bioactive compounds, mechanical perturbation (cyclical or static strain, stress, shear, etc. . . . ), electrical stimulation, and thermal perturbation.

A scaffold can be in any desired geometric conformation, for example, a flat sheet, a spiral, a cone, a v-like structure and the like. A scaffold can be shaped into, e.g., a heart valve, vessel (tubular), planar construct or any other suitable shape. Such scaffold constructs are known in the art (see, e.g., WO02/035992, U.S. Pat. Nos. 6,479,064, 6,461,628, the contents of which are herein incorporated in their entireties by reference). In some embodiments, after culturing the cells on the scaffold, the scaffold is removed (e.g., bioabsorbed or physically removed), and the cells maintain substantially the same conformation as the scaffold, such that, for example, if the scaffold was spiral shaped, the cells form a 3D-engineered tissue that is spiral shaped.

Biopolymer structures can be generated by providing a transitional polymer on a substrate; depositing a biopolymer on the transitional polymer; shaping the biopolymer into a structure having a selected pattern on the transitional polymer (poly(N-Isopropylacrylamide); and releasing the biopolymer from the transitional polymer with the biopolymer's structure and integrity intact. A biopolymer can be selected from a natural or synthetic extracellular matrix (ECM) protein, growth factor, lipid, fatty acid, steroid, sugar and other biologically active carbohydrates, a biologically derived homopolymer, nucleic acids, hormone, enzyme, pharmaceutical composition, cell surface ligand and receptor, cytoskeletal filament, motor protein, silks, polyprotein (e.g., poly(lysine)) or any combination thereof.

The biopolymers used in the generation of the matrices and scaffolds for the embodiments directed to cellular therapies using multimodal TRAIL agents described herein include, but are not limited to, a) extracellular matrix proteins to direct cell adhesion and function (e.g., collagen, fibronectin, laminin, etc.); (b) growth factors to direct cell function specific to cell type (e.g., nerve growth factor, bone morphogenic proteins, vascular endothelial growth factor, etc.); (c) lipids, fatty acids and steroids (e.g., glycerides, non-glycerides, saturated and unsaturated fatty acids, cholesterol, corticosteroids, sex steroids, etc.); (d) sugars and other biologically active carbohydrates (e.g., monosaccharides, oligosaccharides, sucrose, glucose, glycogen, etc.); (e) combinations of carbohydrates, lipids and/or proteins, such as proteoglycans (protein cores with attached side chains of chondroitin sulfate, dermatan sulfate, heparin, heparan sulfate, and/or keratan sulfate); glycoproteins [e.g., selectins, immunoglobulins, hormones such as human chorionic gonadotropin, Alpha-fetoprotein and Erythropoietin (EPO), etc.]; proteolipids (e.g., N-myristoylated, palmitoylated and prenylated proteins); and glycolipids (e.g., glycoglycerolipids, glycosphingolipids, glycophosphatidylinositols, etc.); (f) biologically derived homopolymers, such as polylactic and polyglycolic acids and poly-L-lysine; (g) nucleic acids (e.g., DNA, RNA, etc.); (h) hormones (e.g., anabolic steroids, sex hormones, insulin, angiotensin, etc.); (i) enzymes (types: oxidoreductases, transferases, hydrolases, lyases, isomerases, ligases; examples: trypsin, collegenases, matrix metallproteinases, etc.); (j) pharmaceuticals (e.g., beta blockers, vasodilators, vasoconstrictors, pain relievers, gene therapy, viral vectors, anti-inflammatories, etc.); (k) cell surface ligands and receptors (e.g., integrins, selectins, cadherins, etc.); (l) cytoskeletal filaments and/or motor proteins (e.g., intermediate filaments, microtubules, actin filaments, dynein, kinesin, myosin, etc.), or any combination thereof. For example, a biopolymer can be selected from the group consisting of fibronectin, vitronectin, laminin, collagen, fibrinogen, silk or silk fibroin.

In some embodiments of the compositions and methods described herein, cells engineered to express or secrete a multimodal TRAIL agent are encapsulated in an extracellular matrix comprising a thiol-modified hyaluronic acid and a thiol-reactive cross-linker, such as, for example, polyethylene glycol diacrylate.

In some embodiments of the compositions and methods described herein, cells engineered to express or secrete a multimodal TRAIL agent are encapsulated within permeable membranes prior to implantation. Several methods of cell encapsulation can be employed. In some embodiments, cells will be individually encapsulated. In other instances, many cells will be encapsulated within the same membrane. Several methods of cell encapsulation are well known in the art, such as described in European Patent Publication No. 301,777, or U.S. Pat. Nos. 4,353,888, 4,744,933, 4,749,620, 4,814,274, 5,084,350, and 5,089,272.

In one method of cell encapsulation, the isolated cells are mixed with sodium alginate and extruded into calcium chloride so as to form gel beads or droplets. The gel beads are incubated with a high molecular weight (e.g., MW 60-500 kDa) concentration (0.03-0.1% w/v) polyamino acid (e.g., poly-L-lysine) to form a membrane. The interior of the formed capsule is re-liquified using sodium citrate. This creates a single membrane around the cells that is highly permeable to relatively large molecules (MW .about. 200-400 kDa), but retains the cells inside. The capsules are incubated in physiologically compatible carrier for several hours in order that the entrapped sodium alginate diffuses out and the capsules expand to an equilibrium state. The resulting alginate-depleted capsules is reacted with a low molecular weight polyamino acid which reduces the membrane permeability (MW cut-off 40-80 kDa).

Other exemplary materials suitable for use in matrices and scaffolds include, but are not limited to, PEG diacylate, hyaluronic acid, polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon, nylon silicon, and shape memory materials, such as poly(styrene-block-butadiene), polynorbornene, hydrogels, metallic alloys, and oligo(-caprolactone)diol as switching segment/oligo(p-dioxyanone)diol as physical crosslink. Other suitable polymers can be obtained by reference to The Polymer Handbook, 3rd edition (Wiley, N.Y., 1989), the contents of which are herein incorporated in their reference by entirety.

In some embodiments, additional bioactive substances can be added to a biopolymer matrix or scaffold comprising the cells engineered to express a multimodal TRAIL agent described herein, such as, but not limited to, demineralized bone powder as described in U.S. Pat. No. 5,073,373 the contents of which are incorporated herein by reference; collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digestors; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added bioactive substances can vary widely with optimum levels being readily determined in a specific case by routine experimentation.

Cancer

The limited availability of non-invasive methods to monitor multiple molecular events has been one of the main limitations in testing the efficacy of various therapy paradigms against malignant conditions. The multimodal TRAIL agents, and cells engineered to express these agents, described herein permit simultaneous therapeutic and diagnostic functionalities for use in developing and monitoring cancer therapies. Accordingly, provided herein are methods to treat a subject having a malignant condition comprising administering an effective amount of a pharmaceutical composition comprising a multimodal TRAIL agent, or cells engineered to express or secrete a multimodal TRAIL agent. In some embodiments of these methods, the cells engineered to express or secrete a multimodal TRAIL agent are stem cells. In some such embodiments, the cells are neural stem cells. In some embodiments, the cells engineered to express or secrete a multimodal TRAIL agent are encapsulated in a matrix.

The terms "malignancy," "malignant condition," "cancer," or "tumor," as used herein, refer to an uncontrolled growth of cells which interferes with the normal functioning of the bodily organs and systems. A subject that has a malignancy (i.e., cancer or a tumor) is a subject having objectively measurable malignant or cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments of the methods described herein, a subject having a malignant condition has a brain cancer, brain tumor, or intracranial neoplasm. Intracranial neoplasms or cancers can arise from any of the structures or cell types present in the CNS, including the brain, meninges, pituitary gland, skull, and even residual embryonic tissue. The overall annual incidence of primary brain tumors in the United States is 14 cases per 100,000. The most common primary brain tumors are meningiomas, representing 27% of all primary brain tumors, and glioblastomas, representing 23% of all primary brain tumors (whereas glioblastomas account for 40% of malignant brain tumor in adults). Many of these tumors are aggressive and of high grade. Primary brain tumors are the most common solid tumors in children and the second most frequent cause of cancer death after leukemia in children.

In some embodiments of the methods described herein, a subject having a malignant condition has a glioma or glioblastoma (GBM). Gliomas are brain tumors originating from glial cells in the nervous system. "Glial cells," commonly called neuroglia or simply glia, are non-neuronal cells that provide support and nutrition, maintain homeostasis, form myelin, and participate in signal transmission in the nervous system. The two most important subgroups of gliomas are astrocytomas and oligodendrogliomas. Belonging to the subgroup of astrocytomas, glioblastoma multiforme (referred to as glioblastoma hereinafter) is the most common malignant brain tumor in adults and accounts for approximately 40% of all malignant brain tumors and approximately 50% of gliomas. It aggressively invades the central nervous system and is ranked at the highest malignancy level (grade IV) among all gliomas. Although there has been steady progress in their treatment due to improvements in neuroimaging, microsurgery, diverse treatment options, such as temozolomide or radiation, glioblastomas remain incurable. The lethal rate of this brain tumor is very high: the average life expectancy is 9 to 12 months after first diagnosis. The 5-year survival rate during the observation period from 1986 to 1990 was 8.0%. To date, the five-year survival rate following aggressive therapy, including gross tumor resection, is still less than 10%.

Glioblastoma is the most common primary brain tumor in adults with a very poor prognosis. Treatment for GBM is maximal surgical tumor resection or "debulking" followed by radiation therapy, with concomitant and adjuvant chemotherapy. However, recurrence rates of GBM and the associated patient mortality are nearly 100%. Although resection of the primary tumor mass has shown clinical benefit, adjuvant chemotherapy has provided limited extra benefit. One of the main impediments to the efficient delivery of many therapeutic molecules is the blood brain barrier and vascular dysfunction in the tumor, which prevent many drugs from reaching brain tumor cells. Additionally, many drugs have short systemic half-lives and peak concentrations, which prevent drugs from ultimately reaching the brain and accumulating to therapeutic concentrations in individual brain tumor cells. Tumor cells of glioblastomas are the most undifferentiated ones among brain tumors, so the tumor cells have high potential of migration and proliferation and are highly invasive, leading to very poor prognosis. Glioblastomas lead to death due to rapid, aggressive, and infiltrative growth in the brain. The infiltrative growth pattern is responsible for the unresectable nature of these tumors. Glioblastomas are also relatively resistant to radiation and chemotherapy, and, therefore, post-treatment recurrence rates are high. In addition, the immune response to the neoplastic cells is rather ineffective in completely eradicating all neoplastic cells following resection and radiation therapy.

Glioblastoma is classified into primary glioblastoma (de novo) and secondary glioblastoma, depending on differences in the gene mechanism during malignant transformation of undifferentiated astrocytes or glial precursor cells. Secondary glioblastoma occurs in a younger population of up to 45 years of age. During 4 to 5 years, on average, secondary glioblastoma develops from lower-grade astrocytoma through undifferentiated astrocytoma. In contrast, primary glioblastoma predominantly occurs in an older population with a mean age of 55 years. Generally, primary glioblastoma occurs as fulminant glioblastoma characterized by tumor progression within 3 months from the start with no clinical or pathological abnormalities.

Glioblastoma migrates along myelinated nerves and spreads widely in the central nervous system. In most cases surgical treatment shows only limited sustainable therapeutic effect. Malignant glioma cells evade detection by the host's immune system by producing immunosuppressive agents that impair T cell proliferation and production of the immune-stimulating cytokine IL-2.

Accordingly, in some embodiments of the methods described herein, a subject having a malignant condition has or has had a glioblastoma. In some such embodiments, the composition comprising a multimodal TRAIL agent or cell engineered to express a multimodal TRAIL agent is administered to the subject during or following a surgical procedure, such as a gross tumor resection. In some such embodiments, the composition comprising a multimodal TRAIL agent or cell engineered to express a multimodal TRAIL agent is directly administered to a gross tumor resection site.

In some embodiments, the methods further comprise administering the pharmaceutical composition comprising a multimodal TRAIL agent, or cells engineered to express or secrete a multimodal TRAIL agent, to a subject having a malignant condition, such as a brain tumor (e.g., glioblastoma), along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, gemcitabine, cisplastin, paclitaxel, carboplatin, bortezomib, AMG479, vorinostat, rituximab, temozolomide, rapamycin, ABT-737, and PI-103. In some embodiments, the biologic can comprise a sequence encoding a microRNA or RNA-based inhibitor molecule, such as an inhibitor RNA or iRNA.

In some embodiments of the methods described herein, the methods further comprise administering one or more chemotherapeutics agent to the subject being administered the pharmaceutical composition comprising a multimodal TRAIL agent, or cells engineered to express or secrete a multimodal TRAIL agent. Non-limiting examples of chemotherapeutic agents can include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as flu-darabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the multimodal TRAIL agents or cells engineered to express or secrete a multimodal TRAIL agent described herein to a subject in order to alleviate a symptom of a cancer. As used herein, "alleviating a symptom of a cancer" is ameliorating any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique.

The term "effective amount" as used herein refers to the amount of a multimodal TRAIL agent or cells engineered to express or secrete a multimodal TRAIL agent needed to alleviate at least one or more symptom of the disease or disorder, and relates to a sufficient amount of pharmacological composition to provide the desired effect. The term "therapeutically effective amount" therefore refers to an amount of a multimodal TRAIL agent or cells engineered to express or secrete a multimodal TRAIL agent using the methods as disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the multimodal TRAIL agent), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Some aspects and embodiments disclosed herein can be illustrated by, for example any of the following numbered paragraphs:

1. A multimodal TRAIL agent comprising a reporter module and a therapeutic TRAIL module, wherein said therapeutic TRAIL module comprises an extracellular domain of human TRAIL.
2. The multimodal TRAIL agent of paragraph 1, wherein the extracellular domain of human TRAIL comprises amino acids 114-281 of SEQ ID NO: 1.
3. The multimodal TRAIL agent of any one of paragraphs 1 or 2, further comprising a signal sequence.
4. The multimodal TRAIL agent of paragraph 3, wherein the signal sequence comprises SEQ ID NO: 2.
5. The multimodal TRAIL agent of any one of paragraphs 1-4, wherein the therapeutic TRAIL module further comprises an isoleucine zipper domain.
6. The multimodal TRAIL agent of any one of paragraphs 1-5, further comprising a linker domain C-terminal to the reporter module and N-terminal to the therapeutic TRAIL module.
7. The multimodal TRAIL agent of paragraph 6, wherein the linker domain comprises at least eight amino acids.
8. The multimodal TRAIL agent of paragraph 6, wherein the linker domain comprises the amino acid sequence of SEQ ID NO: 4.
9. A pharmaceutical composition comprising the multimodal TRAIL agent of any one of paragraphs 1-8 and a pharmaceutically acceptable carrier.
10. A vector comprising a nucleic acid sequence encoding the multimodal TRAIL agent of any one of paragraphs 1-8.
11. The vector of paragraph 10, wherein the vector is a lentiviral vector or an adenoviral vector.
12. A cell comprising the nucleic acid sequence encoding the multimodal TRAIL agent of any of paragraphs 1-8.
13. A cell comprising the vector of any one of paragraphs 10 or 11.
14. The cell of any one of paragraphs 12 or 13, wherein the cell is a stem cell.
15. The cell of paragraph 14, wherein the stem cell is a neural stem cell or a mesenchymal stem cell.
16. The cell of any one of paragraphs 12-15, wherein the cell is encapsulated in a matrix or scaffold.
17. The cell of paragraph 16, wherein the matrix comprises a synthetic extracellular matrix.
18. The cell of any one of paragraphs 16 or 17, wherein the matrix is biodegradeable.
19. The cell of any one of paragraphs 17 or 18, wherein the synthetic extracellular matrix comprises a thiol-modified hyaluronic acid and a thiol reactive cross-linker molecule.
20. The cell of paragraph 19, wherein the thiol reactive cross-linker molecule is polyethylene glycol diacrylate.
21. A composition comprising an isolated somatic cell that comprises an exogenously introduced nucleic acid encoding a multimodal TRAIL agent of any one of paragraphs 1-8 operably linked to at least one regulatory sequence.
22. The composition of paragraph 21, wherein the isolated somatic cell is an adult stem cell.
23. The composition of paragraph 22, wherein the adult stem cell is a neural stem cell or a mesenchymal stem cell.
24. The composition of paragraph 23, wherein the neural stem cell is generated from a pluripotent stem cell.
25. The composition of any one of paragraphs 21-24, wherein the isolated somatic cell is encapsulated in a matrix or scaffold.
26. The composition of paragraph 25, wherein the matrix comprises a synthetic extracellular matrix.
27. The composition of any one of paragraphs 25 or 26, wherein the matrix is biodegradeable.
28. The composition of any one of paragraphs 26 or 27, wherein the synthetic extracellular matrix comprises a thiol-modified hyaluronic acid and a thiol reactive cross-linker molecule.
29. The composition of paragraph 29, wherein the thiol reactive cross-linker molecule is polyethylene glycol diacrylate.
30. A method of treating a subject having a malignant condition comprising administering a therapeutically effective amount of the pharmaceutical composition of paragraph 9.
31. A method of treating a subject having a malignant condition comprising administering a therapeutically effective amount of the cells of any of paragraphs 12-20 or the composition of paragraphs 21-29.
32. The method of any one of paragraphs 30 or 31, wherein the malignant condition is a glioblastoma.
33. The method of any one of paragraphs 30-32, further comprising administering to the subject, one or more additional chemotherapeutic agents, biologics, drugs, or treatments as part of a combinatorial therapy.
34. The method of paragraph 33, wherein the chemotherapeutic agent, biologic, drug, or treatment is selected from the group consisting of: radiation therapy, tumor resection surgery, gemcitabine, cisplastin, paclitaxel, carboplatin, bortezomib, AMG479, vorinostat, rituximab, temozolomide, rapamycin, ABT-737, and PI-103.
35. The method of any one of paragraphs 30-34, wherein the pharmaceutical composition of paragraph 9, the cells of any of paragraphs 12-20, or the composition of paragraphs 21-29 is administered at a surgical site.
36. The method of paragraph 35, wherein the surgical site is a tumor resection site.
37. The pharmaceutical composition of paragraph 9 for use in a method of treating a malignant condition.
38. The cells of any one of paragraphs 12-20 for use in a method of treating a malignant condition.
39. The composition of any one of paragraphs 21-29 for use in a method of treating a malignant condition.
40. The use of any of paragraphs 37-39, wherein the malignant condition is a glioblastoma.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

EXAMPLES

Example 1

A MultiModal TRAIL Agent Integrating Therapeutic and Diagnostic Activities Reveals Multiple Aspects of Stem Cell-Based Therapy Engineering and Screening of Optimized Therapeutic and Diagnostic Luciferase-S-TRAIL Fusions To create novel multimodal TRAIL agents that can both be easily visualized for serial monitoring of cell-based pharmacokinetics and retain potent anti-tumor function, numerous lentiviral vectors (LV) encoding fusion molecules between S-TRAIL, i.e., a therapeutic, secretable TRAIL module, and various luciferases, as reporter modules, were generated. (FIG. 1, FIG. 6A-6D, Table 1). To select the molecule with optimized diagnostic and therapeutic activity, 293T cells were transduced with LV encoding each construct at multiplicity of infection (MOI) 1 (FIG. 6B), and conditioned media from transfected cells was screened for light emission, S-TRAIL concentration, and anti-tumor efficacy. To first select the appropriate molecular composition and orientation, direct fusions of firefly luciferase (FLuc), *Renilla* luciferase (RLuc), or *Gaussia princeps* luciferase (GpLuc) to the C-terminus of S-TRAIL were screened (FIG. 1, constructs 1-3). Of these fusions, only TRAIL-GpLuc (TRGp, construct 3) showed light emission by bioluminescence imaging on media from transduced cells; however, no S-TRAIL was detected in the conditioned media and no killing of Gli36-EGFRvIII human cancer cells was observed from TRGp-containing media (FIG. 1, construct 3; Table 1). In contrast, when GpLuc was fused to the N-terminus of S-TRAIL (GpTR, construct 4), detectable levels of light emission, S-TRAIL concentration, and reduction in tumor cell viability were observed (FIG. 1, Table 1).

As GpTR showed maximal diagnostic and therapeutic activity, the effects of intramolecular spacing were investigated by engineering GpLuc and S-TRAIL fusions separated by two different linker modules. As shown in FIG. 1, increased intramolecular spacing increased the function of both GpLuc and S-TRAIL as the fusion variant containing linker-2 (GpL2TR, construct 6) showed markedly increased diagnostic and therapeutic activity compared to the GpTR direct fusion.

Lastly, to maximize delivery by optimizing extracellular secretion, two additional multimodal TRAIL fusion variants were engineered in which the endogenous secretion sequence was replaced by the signal sequence from Flt3 ligand, a sequence known to induce highly efficient protein secretion (Shah et al. Cancer Research 2004) (FIG. 1). The first variant was based on GpL2TR (SGpL2TR, construct 7). In the second (SRLucOL2TR, construct 8), GpLuc was replaced by an alternative form of *Renilla* luciferase (RlucO) optimized for extracellular light production and suggested to have increased in vivo luciferase activity compared to GpLuc (Venisnik et al. Mol Imaging Biol 2007). The results showed that the modified secretion sequence in SGpL2TR led to over a 1.5-fold increase in photon emission compared to that in GpL2TR (FIG. 1, Table 1). Similarly, greater S-TRAIL concentration and tumor cell killing were observed by SGpL2TR. Although SRLucOL2TR demonstrated significant diagnostic and therapeutic activity, in vitro levels of bioluminescence signal, S-TRAIL concentration, and tumor cell killing were less than those observed for SGpL2TR yet greater than or equal to those for GpL2TR (FIG. 1, Table 1).

Characterizing Optimized Luciferase-S-TRAIL Fusions In Vivo

Figures 2A, 2B, 2C, 2D, 2E:
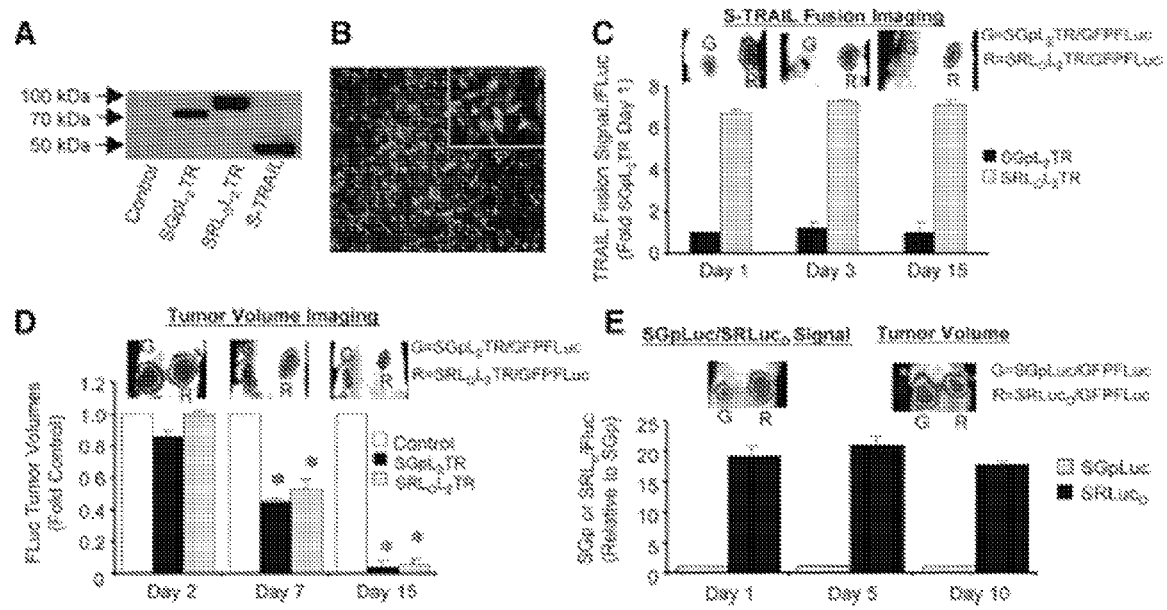
FIGS. 2A-2E depict screening S-TRAIL and luciferase fusion variants in vivo. (2A): Western blot analysis of lysates from 293T cells transduced with LV demonstrating expression of SGpL2TR and SRLOL2TR. (2B): Representative green fluorescent protein (GFP) photomicrograph (large micrograph, 4×; inset, 10×) of human U251 glioma cells co-transduced with equal MOI of lentiviral vectors (LV) encoding SGpL2TR, SRLOL2TR, or control virus and GFP-FLuc. GFP appears as light spots. (2C-2D): Areas with fluorescence appear as dark zones ringed with a lighter zone. U251 glioma cells co-expressing GFP-FLuc and SGpL2TR, SRLOL2TR, or control virus were implanted subcutaneously in mice and imaged on days 1, 3, and 15 to monitor secretion of TRAIL fusion proteins (GpLuc or RLucO intensities, (2C)) and on days 2, 7, and 15 to follow changes in tumor volume (FLuc intensities, (2D)). (2E): Representative images and summary data of similar experiments as those described in (2C and 2D) instead using nontherapeutic SGpLuc or SRLucO. Subcutaneous tumors were imaged on days 1, 5, and 10 for FLuc intensities to determine tumor volume or to monitor secretion of SGpLuc or SRLucO by coelenterazine injection. Representative day 10 images are shown. In all panels, *, $p<0.05$ versus control. Abbreviations: SGpL2TR, SGpLuc-Linker 2-TRAIL; SRLOL2TR, SRlucO-linker 2-TRAIL; S-TRAIL, secreted variant of the pro-apoptotic protein tumor necrosis factor-related apoptosis-inducing ligand.

As the results above indicate, the multimodal TRAIL agents SGpL2TR and SRLucOL2TR described herein had the greatest diagnostic and therapeutic activities in vitro, so they were investigated for their activity in vivo. To first confirm proper expression of the proteins, Western blot analysis was performed on lysates from transduced cells using an anti-TRAIL antibody. As shown in FIG. 2A, both SGpL2TR and SRLucOL2TR were detected at high levels and at the anticipated size. For in vivo characterization of SGpL2TR and SRLucOL2TR, U251 cancer cells that have been previously shown to have a slow rate of TRAIL-induced cell death (Kock et al. Neoplasia 2007, Hingtgen et al. Mol Cancer Ther 2008) were utilized. To track changes in tumor volume, U251 cells were first transduced with LV vectors encoding GFP-FLuc, followed by transduction with SGpL2TR, SRLOL2TR, or control virus (FIG. 2B, FIG. 6A-6D). Following subcutaneous implantation, GpLuc or RLucO imaging was performed to track fusion proteins and Fluc imaging was performed to monitor changes in tumor volume. As shown in FIGS. 2C-2D, SGpL2TR or SRLucOL2TR imaging on days 1, 3, and 15 demonstrated stable secretion of the luciferase-S-TRAIL fusion proteins from the infected cells when expressed relative to FLuc photon emission (FIG. 2C). This stable delivery coincided with a gradual yet significant reduction in tumor volume determined by FLuc imaging on days 2, 7, and 15 (FIG. 2D). Interestingly, in contrast to the results observed in vitro, tumors transduced with SRLOL2TR showed greater photon emission than SGpL2TR-transduced tumor in vivo. The enhanced photon emission by RLucO-containing fusion was not due to differences in TRAIL-induced reduction in tumor volume, as further side-by-side in vivo comparison using nontherapeutic forms of SGpLuc and SRLucO confirmed greater light emission from RLucO tumors (FIG. 2E, FIGS. 7A-7D). As both SGpL2TR and SRLOL2TR display similar anti-tumor activity, yet SRLOL2TR shows enhanced light emission allowing improved in vivo detection (data summarized in Table 1), all further studies described in this Example utilized SRLOL2TR. Together, these results demonstrate the engineering and optimization of SRLOL2TR to follow delivery and therapeutic efficacy of the multimodal TRAIL agent protein in vitro and in vivo. Additionally, they demonstrate the importance of molecular organization, intermolecular spacing, optimized secretion, and in vivo activity in developing multifunctional and multimodal TRAIL molecules.

Figures 3A, 3B, 3C, 3D, 3E, 3F, 3G, 3H, 3I, 3J:
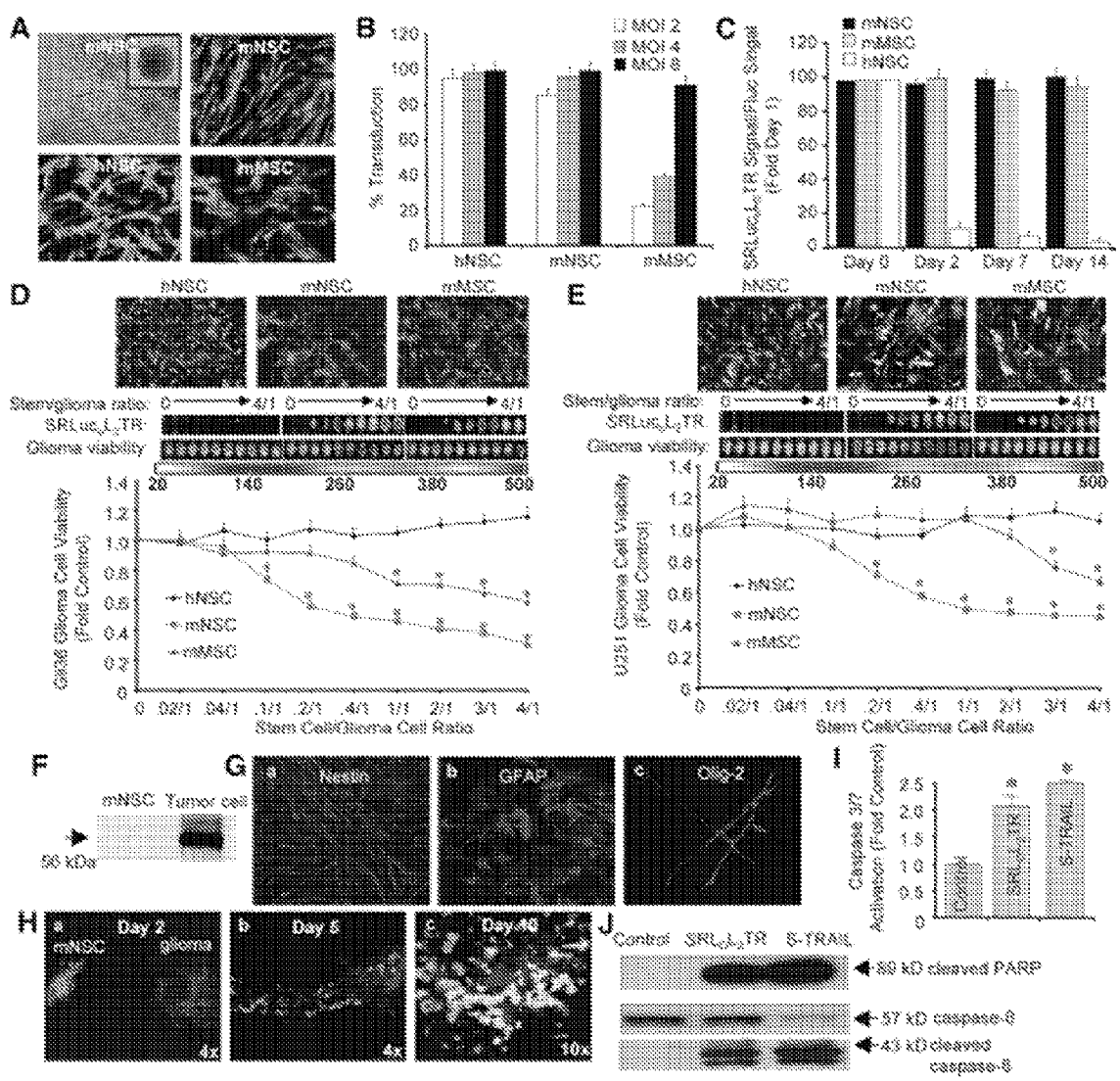
FIGS. 3A-3J present imaging of SRLOL2TR that reveals differences in stem cell secretion and cancer cell killing (3A): Representative images of mNSC, hNSC, and mMSC transduced with LV encoding SRLOL2TR. GFP activity appears as lighter areas in panels other than top left which is a brightfield image. (3B): Summary data demonstrating differences in transduction efficiency between mNSC, hNSC, and mMSC 24 hours post-transduction with increasing MOI of LV-SRLOL2TR. Green fluorescent protein (GFP)-positive cells were counted and expressed as a ratio of total cell number for each stem cell type. (3C): Photon emission from mNSC, hNSC, and mMSC transduced with LV-SRLOL2TR were assayed at days 0, 2, 7, and 14 post-transduction. (3D and 3E): Representative images and summary graphs demonstrating the effects of different stem cell lines secreting SRLOL2TR co-cultured at increasing stem cell to tumor cell ratios with Gli36-EGFRvIII (3D) or U251 human cancer cells. Green fluorescence appears as the darkest grey, red fluorescence as the medium grey, and the lightest zones are those where red and overlap. (3E). After 24 hours of co-culture, levels of SRLOL2TR secretion by the stem cells were visualized by RLucO bioluminescence imaging and tumor cell killing was visualized by Fluc bioluminescence imaging and quantified using a luminometer. Luminesence appears as lighter zones. (3F): Western blot analysis of cell lysates from mNSC or Gli36-EGFRvIII tumor cells demonstrating the expression of DR4 in each cell line. (3G): Immunocytochemical analysis of undifferentiated mNSC stained with an antibody against NSC marker Nestin (a), or following 10 days of differentiation using antibodies against glial fibrillary acidic protein (GFAP) (b) or Olig-2 (c). Green fluorescence appears as the darkest grey, red fluorescence as the medium grey, and the lightest zones are those where red and overlap. (3H): Representative photomicrographs demonstrating the migration of transduced mNSC towards gliomas over time. GFP-expressing mNSC were implanted 1 mm lateral to established Gli36-EGFRvIII-FD intracranial gliomas. On days 2 (a), 5 (b), and 10 (c) post-mNSC, implantation mice were sacrificed, brains were removed and sectioned, and both mNSC and glioma volumes were visualized using fluorescence confocal microscopy. Panels a and b: 4× magnification; Panel c: 10× magnification. (3I and 3J): Human Gli36-EGFRvIII glioma cells were incubated with conditioned media from mNSC transduced with control vector, SRLOL2TR, or purified S-TRAIL and caspase-3/7 activity (I), cleaved caspase-8 levels (3J), and cleaved PARP levels (3J) were determined by luciferase-based caspase 3/7 assay (3I) and Western blot analysis (3J). In all panels, *, $p<0.05$ versus control. Abbreviations: hNSC, human neural stem cells; mMSC, primary mouse mesenchymal stem cells; mNSC, primary mouse neural stem cells; SRLucOL2TR, SRlucO-linker 2-TRAIL.
Figures 8A, 8B:
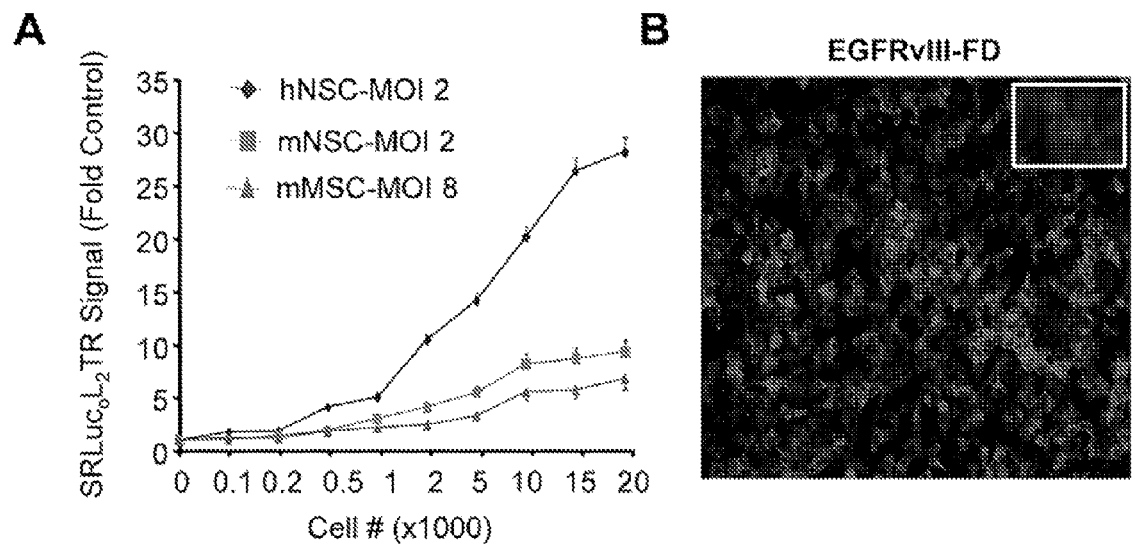
FIGS. 8A-8B depict mNSC secretion and characterization of Gli36-EGFRvIII-FD fluorescence. (8A) Summary graph demonstrating differences in the levels of SRLOL2TR secretion from equally transduced mNSC, hNSC, and mMSC. After transduction with LV-SRLOL2TR, mNSC (MOI 2), hNSC (MOI 2), and mMSC (MOI 8) were plated at increasing cell numbers. Secretion levels were determined by visualization of SRLOL2TR levels in equal volumes of conditioned media by bioluminescence imaging. (8B) Representative images of Gli36-EGFRvIII expressing FLuc-DsRed2.

SRLOL2TR Reveals Stem Cell Lines Exhibit Different Secretion Kinetics that Effect Cancer Cell Killing Different stem cell lines were investigated for evidence of different secretion levels and duration of delivery that influence anti-tumor efficacy. To this end, three different stem cell lines, (1) primary mouse neural stem cells (mNSC), (2) human neural stem cells (hNSC), and (3) primary mouse mesenchymal stem cells (mMSC), were transduced with increasing MOI of lentivirus (LV) encoding SRLOL2TR (FIGS. 3A-3B). For transduction of mNSC, cells were first seeded on coated tissue culture plates to establish a monolayer that ensured efficient LV-mediated transduction (FIG. 3A). As shown in FIG. 3B, hNSC and mNSC were robustly transduced at low MOI, whereas mMSC required MOI of 8 to reach the same percentage of transduction as hNSC or mNSC. Serial bioluminescence imaging performed on media from equally transduced cells showed that, despite early robust secretion of SRLOL2TR by hNSC (FIG. 8A), levels rapidly declined and were nearly absent by 48 hours (FIG. 3C) due to TRAIL-induced death of hNSC. In contrast, mNSC and mMSC retained stable secretion of SRLOL2TR through 14 days, although mNSC secretion of SRLOL2TR was markedly greater than levels detected from mMSC (FIG. 8A).

To determine if differences in secretion between the three stem cell lines translated to differences in anti-tumor cell efficacy, co-culture studies were performed using different ratios of stem cells expressing SRLOL2TR and glioma lines with different sensitivities to TRAIL-mediated apoptosis (Gli36-EGFRvIII, highly TRAIL sensitive; U251, less TRAIL sensitive), both engineered to express mCherryF-Luc. The imaging of hNSC secretion showed extremely low levels of SRLOL2TR in the media at the time point assayed, and this translated to minimal effects on either Gli36-EGFRvII (FIG. 3D) or U251 (FIG. 3E) tumor cell viability. Imaging of media from mNSC showed robust levels of SRLOL2TR that increased as the stem cell/tumor cell ratio increased, with a ratio of 0.04/1 leading to detectable amounts of SRLOL2TR. Importantly, the efficient secretion of SRLOL2TR lead to stem cell/tumor cell ratios as low as 0.1/1 and 0.2/1, significantly decreasing the viability of Gli36-EGFRvII (FIG. 3D) or U251 (FIG. 3E) cells, respectively, in a dose-dependent manner. Imaging of the third stem cell line, mMSC, showed markedly lower levels of SRLOL2TR compared to mNSC, suggesting significantly lower delivery of therapeutic proteins (FIGS. 3D-3E). Similarly, Gli36-EGFRvIII cell viability was decreased but required 10-fold more therapeutic mMSC to induce killing compared to mNSCs (FIG. 3D), whereas U251 cells required a mMSC/tumor ratio of 3/1 before a significant difference in tumor cell viability was detected (FIG. 3E). Together, these results show that imaging of the multimodal TRAIL agent SRLOL2TR revealed marked differences in the delivery of therapeutics by hNSC, mNSC, and mMSC, which resulted in significant differences in the ability of each line to induce tumor cell killing in human cancer cell lines both highly sensitive and less sensitive to TRAIL. Additionally, mNSC secreted the highest levels of SRLOL2TR and induced the largest decrease in cancer cell viability at the lowest stem cell/cancer cell ratio.

On the basis of these results, mNSC secreting SRLOL2TR were selected as the stem cell line for further investigation. Western blot analysis confirmed that mNSC did not express TRAIL death receptors (FIG. 3F). Immunocytochemistry revealed that these cells robustly expressed the NSC marker Nestin (FIG. 3Ga) and possessed the capacity to generate cells of neural lineage (FIGS. 3Gb-3Gc). In addition, when transduced stem cells were implanted 1 mM adjacent to established Gli36-EGFRvIII human gliomas expressing FLuc-DsRed2 (Gli36-EGFRvIII-FD; FIG. 8B) in the frontal lobe of mice, two distinct populations of green stem cells and red gliomas were observed 2 days post-implantation (FIG. 3 Ha). However, stem cells were observed specifically migrating towards the glioma by day 5 (FIG. 3 Hb) and showed accumulation in the tumor by day 10 (FIG. 3 Hc). Demonstrating the role of the extrinsic apoptotic cascade in stem cell-secreted SRLOL2TR-induced cancer cell death, Western blot analysis and luciferase-based assay on Gli36-EGFRvIII cells treated with SRLOL2TR conditioned media revealed significant activation of caspase 3/7 (FIG. 3I) and increases in cleavage of caspase-8 and Poly(ADP-ribose) polymerase (PARP) (FIG. 3J). These results show that transduced mNSC retain all the characteristics of NSC in vitro and also migrate specifically to gliomas in mice bearing intracranial tumors.

Figures 4A, 4B, 4C, 4D, 4E, 4F, 4G, 4H, 4I:
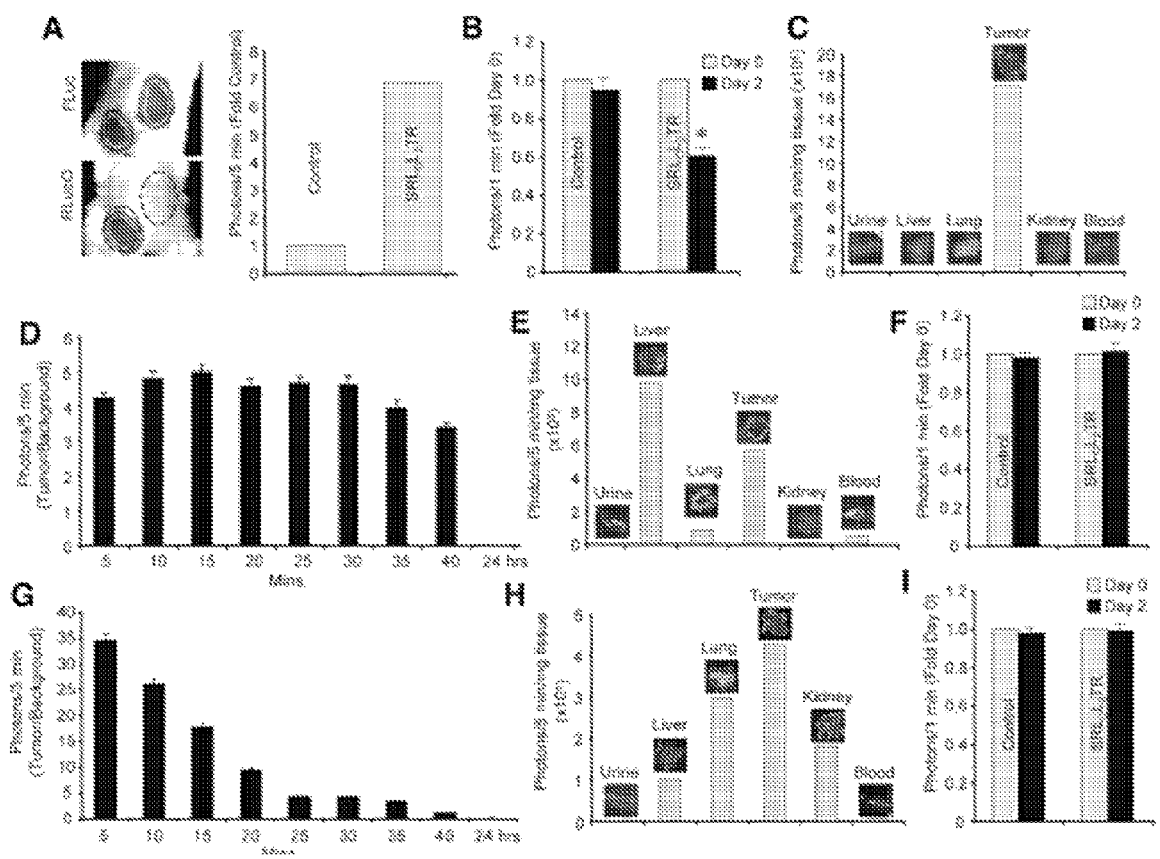
FIGS. 4A-4I demonstrate that delivery by engineered stem cells improves SRLOL2TR pharmacokinetics in vivo. (4A): Representative images and summary graphs showing SRLOL2TR levels when delivered to tumors by engineered stem cells. Gli36-EGFRvIII-FD glioma cells were implanted subcutaneously in mice, and 24 hours later FLuc imaging was performed to demonstrate the localization of the tumor. 24 hours post-imaging, mNSC secreting SRLOL2TR were injected around one of the established tumors, and SRLOL2TR imaging was performed to visualize the secretion of SRLOL2TR. (4B): Summary graph showing the effects on tumor volume of control mNSC or mNSC secreting SRLOL2TR 48 hours after implantation around established Gli36-EGFRvIII-FD tumors assessed by FLuc imaging. (4C): Ex vivo analysis of biodistribution of mNSC-delivered fusion proteins assessed by RLucO imaging of organs removed 1-hour post injection of coelenterazine. (4D-4I): In vivo bioluminescence imaging of conditioned medium from LV-SRLOL2TR transduced cells injected into mice bearing established Gli36-EGFRvIII-FD subcutaneous tumors by i.v. infusion (4D) or direct intratumoral administration (4G) and analyzed at different time points after coelenterazine injection. Ex vivo bioluminescence imaging of organs and tumor tissue from mice 1-hour post-injection of media administered by i.v. infusion (4E) or direct injection (4H) followed by coelenterazine. Forty-eight hours after media injection, Fluc imaging was performed to determine changes in tumor volumes (4F, 4I). In all panels, *, $p<0.05$ versus control. Abbreviations: SRLOL2TR, SRlucO-linker 2-TRAIL. Luminesence appears as grey areas or black areas ringed by grey.
Figures 9A, 9B, 9C:
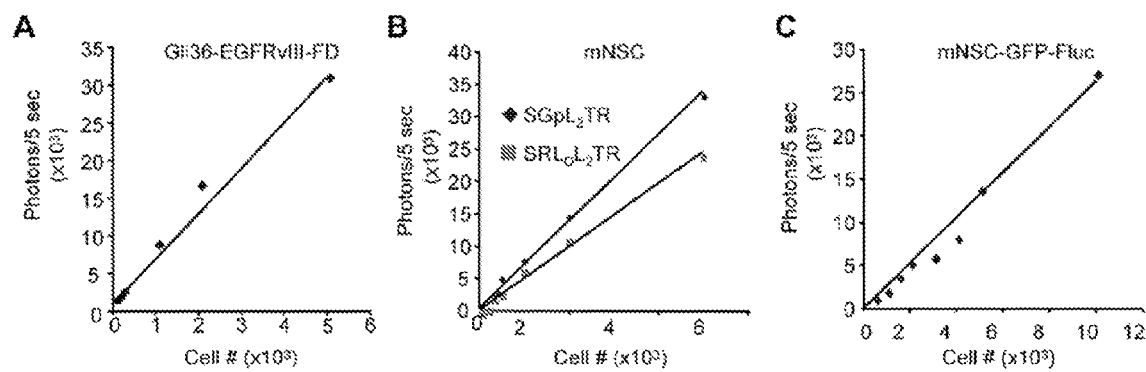
FIGS. 9A-9C depict the linear correlation of Gli36-EGFRvIII-FD and mNSC-SRLOL2TR photon emission. (9A-9C) In vitro bioluminescence imaging showing correlation of luciferase activity with different numbers of Gli36-EGFRvIII-FD cells (9A), mNSC-SRLOL2TR (9B) or mNSC-GFP-FLuc (9C) plated at increasing number.

Stem Cell-Based Delivery Significantly Improves Pharmacokinetics and Efficacy of Therapies Determined by Noninvasive Imaging of SRLOL2TR In clinics, numerous chemotherapies are administered to patients via i.v. infusion or direct injection, yet these methods can lead to significant levels of the drugs accumulating in normal organs, resulting in dose-limiting toxicities. In stem cell-based delivery, the cells are typically engrafted around the tumor to provide sustained levels of therapeutic protein for direct targeting of tumor cells. It was determined if SRLOL2TR could be used to visualize differences between the pharmacokinetics of delivery to tumors by mNSC and i.v. or intratumoral injection of purified protein in vivo in models designed to mimic the clinical settings. First, the bioluminescence signal from both Gli36-EGFRvIII-FD and mNSC engineered with SRLOL2TR were shown to correlate directly with cell number (FIGS. 9A-9B). Next, mice were implanted with mNSC expressing SRLOL2TR around established Gli36-EGFRvIII-FD tumors to mimic clinical engraftment of cell-based therapies. RLucO imaging performed 24 hours after implantation of mNSC revealed a robust bioluminescence signal that co-localized with the established tumor (FIG. 4A). FLuc bioluminescence imaging showed a significant reduction in tumor volume by 48 hours (FIG. 4B). Ex vivo analysis demonstrated RLucO signal was present in the excised tumor but absent from other organs and tissues (FIG. 4C). Alternatively, when media containing SRLOL2TR was delivered by i.v. injection to mimic the systemic delivery of chemotherapies, a signal was detectable that persisted through 40 minutes but was absent by 24 hours (FIG. 4D). Furthermore, the bioluminescence signal was detected in the liver, lung, kidney, and blood as well as the tumor (FIG. 4E) and did not have any effect on tumor volume (FIG. 4F). Lastly, to determine if SRLOL2TR could be used to visualize differences in delivery of purified protein administered in the same manner as stem cells, media containing SRLOL2TR was injected directly into established tumors. As shown in FIGS. 4G-4I, the direct injection of media resulted initially in a robust signal present at the site injection that gradually decreased to baseline near baseline levels by 40 minutes and was entirely absent at 24 hours (FIG. 4G). Similar to i.v. infusion, the direct injection of media to the tumor led to detectable accumulation of the SRLOL2TR in the liver, lung, and kidney in addition to the tumor (FIG. 4H) and also had minimal effect on tumor volume (FIG. 4I).

The results described herein indicate that combining the novel SRLOL2TR protein and optical imaging permits elucidation of differences in pharmacokinetics, tissues distribution, and therapeutic efficacy of anti-cancer proteins delivered to tumors by engineered stem cells or i.v. injection. As SRLOL2TR allows visualization of therapeutic levels in real-time, we show that a single administration of engineered stem cells provides continuous sustained and localized delivery of therapeutics that attenuates tumor growth, whereas a single i.v. infusion or direct administration of media containing SRLOL2TR results in widespread off-target binding and significantly shortened delivery window that correlates with minimal anti-tumor effects.

Figures 5A, 5B, 5C, 5D:
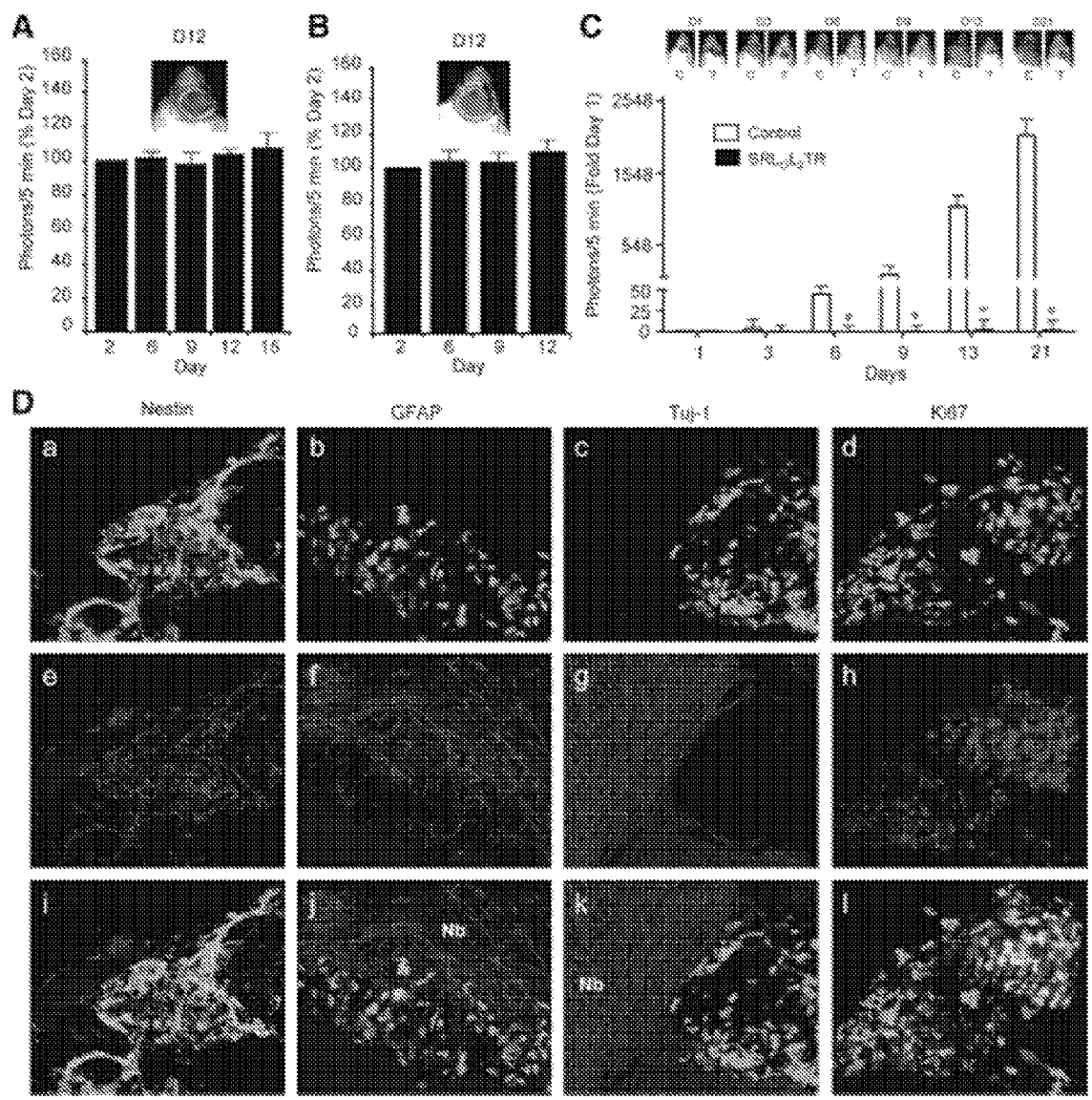
FIGS. 5A-5D demonstrate that stem cells efficiently deliver SRLOL2TR to eradicate intracranial glioblastoma. (5A): Representative FLuc bioluminescent images and summary data of mice implanted intracranially with mNSC transduced with LV-GFP-FLuc, mixed with Gli36-EGFRvIII, and serially imaged for 15 days. (5B-5D): mNSC were transduced with control vector or SRLOL2TR, and implanted with Gli36 EGFRvIII-FD intracranially in mice. On days 2, 6, 9, and 12 post-implantation, SRLOL2TR mice were injected with coelenterazine and RLucO imaging was performed to visualize SRLOL2TR secretion (5B). Mice were injected with D-Luciferin and FLuc imaging was performed to visualize changes in glioma on days 1, 3, 6, 9, 13, and 21 post-implantation. (5C): Representative images and summary data are shown. C=Control; T=SRLOL2TR. (5D): Immunohistochemistry was performed on sections from brains containing GFP-FLuc-expressing mNSC 4 days post-implantation. Representative merged images are shown of brain sections containing mNSC (light grey) and stained with antibodies (darker grey) against nestin (a, e, i), glial fibrillary acidic protein (GFAP) (b, f, j), Tuj-1 (c, g, k), or Ki67 (d, h, l). Nb=normal brain; T=tumor. In all panels, *, $p<0.05$ versus control. GFP is visualized as a light grey and LUC as a darker grey. Abbreviations: SRLOL2TR, SRlucO-linker 2-TRAIL.

Stem Cells Lead to Sustained Delivery of SRLOL2TR for Treatment of Highly Malignant Intracranial Glioblastoma Lastly, the above cell-based approaches were tested in an intracranial glioma model, a disease where effective delivery of therapeutic agents is further limited by the blood-brain barrier. To first investigate the survival of mNSC in the context of glioma, mNSC expressing GFP-FLuc (FIG. 9C) were mixed with Gli36-EGFRvIII human glioma cells and implanted intracranially in mice. FLuc bioluminescence imaging revealed the presence of transduced mNSC in the brain, and the levels remained constant through 15 days (FIG. 5A). After confirming intracranial survival of transduced mNSC, therapeutic mNSC engineered to express SRLOL2TR were implanted intracranially in severe combined immunodeficiency (SCID) mice together with Gli36-EGFRvIII-FD. RLucO imaging on days 2, 6, 9, and 12 showed robust and stable delivery of SRLOL2TR by mNSC (FIG. 5B). Serial FLuc imaging revealed that mNSC delivery of SRLOL2TR led to marked attenuation in glioma progression, with significant decrease in FLuc signal in SRLOL2TR-treated mice by day 6 (FIG. 5C). Post-mortem immunohistochemical analysis performed 4 days post-implantation confirmed the presence of GFP-expressing mNSC (FIG. 5D) and demonstrated expression of the NSC marker Nestin (FIGS. 5Da, 5De, 5Di). Furthermore, mNSC did not stain positive for the astrocyte marker glial fibrillary acidic protein (GFAP) (FIGS. 5Db, 5Df, 5Dj), the neuronal marker Tuj-1 (FIGS. 5Dc, 5Dg, 5Dk), or the proliferation marker Ki67 (FIGS. 5D-d,h,l), which showed strong staining of the highly proliferating glioma cells. By simultaneously monitoring therapeutic delivery by mNSC in the brain and intracranial glioma volumes, these results show that therapeutic stem cells secreting SRLOL2TR are effective anti-glioma therapies.

Conclusions

Demonstrated herein is the development of novel multi-functional, multimodal TRAIL agents as molecules that have both diagnostic (in vivo tracking via optical reporters) and therapeutic (anti-tumor via the cytotoxic agent TRAIL) properties. Further, their application in characterizing therapeutic delivery by engineered stem cells is demonstrated. To develop molecules with the greatest optical reporter activity and highest tumor cell toxicity, it is critical to select both the appropriate luciferase and orientation for the fusion to TRAIL (N- or C-terminus). After screening fusion proteins containing several different luciferase proteins, the results showed fusion proteins containing GpLuc produced the greatest light emission in vitro, while SRLucO containing fusions performed better in vivo.

Furthermore, it was shown that fusion of luciferase proteins to the N-terminus of TRAIL permitted retention of both the imaging properties of the luciferase and anti-tumor properties of TRAIL, whereas C-terminal fusions inactivated the multimodal TRAIL agent. Without wishing to be bound or limited by theory, the inactivation of S-TRAIL is most likely due to the fact that the C-terminus of S-TRAIL contains the cell-binding domain of TRAIL (Wiley et al, Immunity 1995), and therefore, the fusion of proteins to the C-terminus of TRAIL either prevents proper folding of the protein or interferes with interaction of S-TRAIL with its receptors, DR4 and DR5, which is in agreement with the structure of other TRAIL fusion proteins (Shen et al. Appl Microbiol Biotechnol 2007, Bremer et al. Neoplasia 2004). Furthermore, previous reports have emphasized the importance of protein linkers in order to achieve optimal activity of luciferase fusion proteins (Venisnik et al. Protein Eng Des Sel 2006, Ray et al. Cancer Res 2003). In agreement with these reports, greater extracellular BLI signal, TRAIL levels, and cell killing were observed with the inclusion of longer intracellular linkers. Without wishing to be bound or limited by theory, the increased intramolecular spacing between the therapeutic, secretable module, S-TRAIL, and the reporter module, luciferase, by inclusion of linker-2 better preserved the functionality of both the luciferase and S-TRAIL modules, thus leading to the observed increases in photon emission, S-TRAIL concentration, and cell killing Taken together, the multimodal TRAIL agent SRLOL2TR combines the potent anti-tumor properties of S-TRAIL with the simple noninvasive assessment of therapeutic delivery afforded by luciferase imaging.

One of the primary challenges to achieving effective anti-tumor therapy is highly efficient delivery of the anti-tumor agent specifically to the tumor, while minimizing toxicity to nonmalignant tissue. Although simple to administer, systemic administration of therapies often leads to accumulation of the toxic compounds at high levels in the liver and kidneys, resulting in dose-limiting renal- and hepatotoxicity (Kelley et al. J Pharmacol Exp Ther 2001, Lin, Drug Metab Dispos 1998). TRAIL has been shown to have minimal cytotoxic effects on normal tissue; however, its short half-life and accumulation after systemic injection have been limitations to its potential use in clinics (Ashkenazi et al., J Clin Oncol 2008). Because of their potential to migrate to sites of disease and integrate into the cytoarchitecture of the brain, stem cells (NSC, MSC) have received much interest for the treatment of numerous neurologic disorders (Corsten and Shah, Lancet Oncology 2008, Singec et al. Annu Rev Med 2007). Previous studies from our lab and others demonstrated that NSC and human MSC migrate extensively throughout the murine brain and exhibit an inherent capacity to home to established gliomas (Sasportas et al. Proc Natl Acad Sci 2009, Shah et al Ann Neurol 2005, Shah et al. J Neurosci 2008). Stem cells armed with S-TRAIL inhibited progression of gliomas in a xenogenic transplant model (Sasportas et al. Proc Natl Acad Sci 2009, Shah et al Ann Neurol 2005); however, assessing the pharmacokinetics of the molecules released by therapeutic NSC has been difficult.

As described herein, the combination of SRLOL2TR and real-time imaging demonstrated the advantages of stem cell-based delivery. Noninvasive monitoring of SRLOL2TR pharmacokinetics revealed a markedly increased delivery time and reduced nonspecific biodistribution that culminated in effective reduction in tumor burden. In contrast, i.v. or intratumoral injection of SRLOL2TR resulted in rapid clearance, widespread biodistribution, and minimal effects on the tumor. The results provided herein permit the first real-time comparison of pharmacokinetics when therapies are delivered by stem cells or systemic administration.

The ability to serially monitor the level of therapeutic protein delivered by stem cells, such as NSCs, is critical to effective cell-based therapy. Longitudinal imaging of therapies permits confirmation of the initial levels delivered, permits confirmation of whether there is a need to increase dose by injection of additional therapeutic NSC should inhibition of tumor growth not be observed, or indicates the need for re-administration if the dose begins to decline. The examples shown herein of intracranial glioblastoma xenograft using the combination of mNSC and SRLOL2TR revealed robust and sustained delivery of TRAIL fusion as early as 2 days post-implantation and showed that sustained SRLOL2TR persisted through day 12. Importantly, the continuous delivery of SRLOL2TR by stem cells markedly decreased glioma burden as early as day 6. These results demonstrate the effectiveness of stem cell-mediated delivery of SRLOL2TR as an anti-glioma therapy, as significant tumor regression was achieved with a single administration of therapeutically engineered stem cells. In the event that SRLOL2TR levels decrease at time points beyond those described herein, the diagnostic functionality of SRLOL2TR would reveal these changes, and stem cells could be re-administered to ensure continued suppression of tumor growth.

In conclusion, shown herein is the engineering of novel fusion multimodal TRAIL agents with both diagnostic and therapeutic functionalities, and utilization of the novel multimodal TRAIL agent SRLOL2TR as a means to determine vital aspects of stem cell-based therapies. These studies showed, in part, how differences in delivery efficiency between different cell lines affected their therapeutic application, how improved pharmacokinetics mediated by stem cell delivery influenced anti-tumor efficacy of a therapy, and how selection of the optimal therapeutic stem cell line can effectively attenuate highly malignant tumors in vivo.

Example 2

Figures 10A, 10B, 10C, 10D, 10E, 10F, 10G, 10H, 10I, 10J:
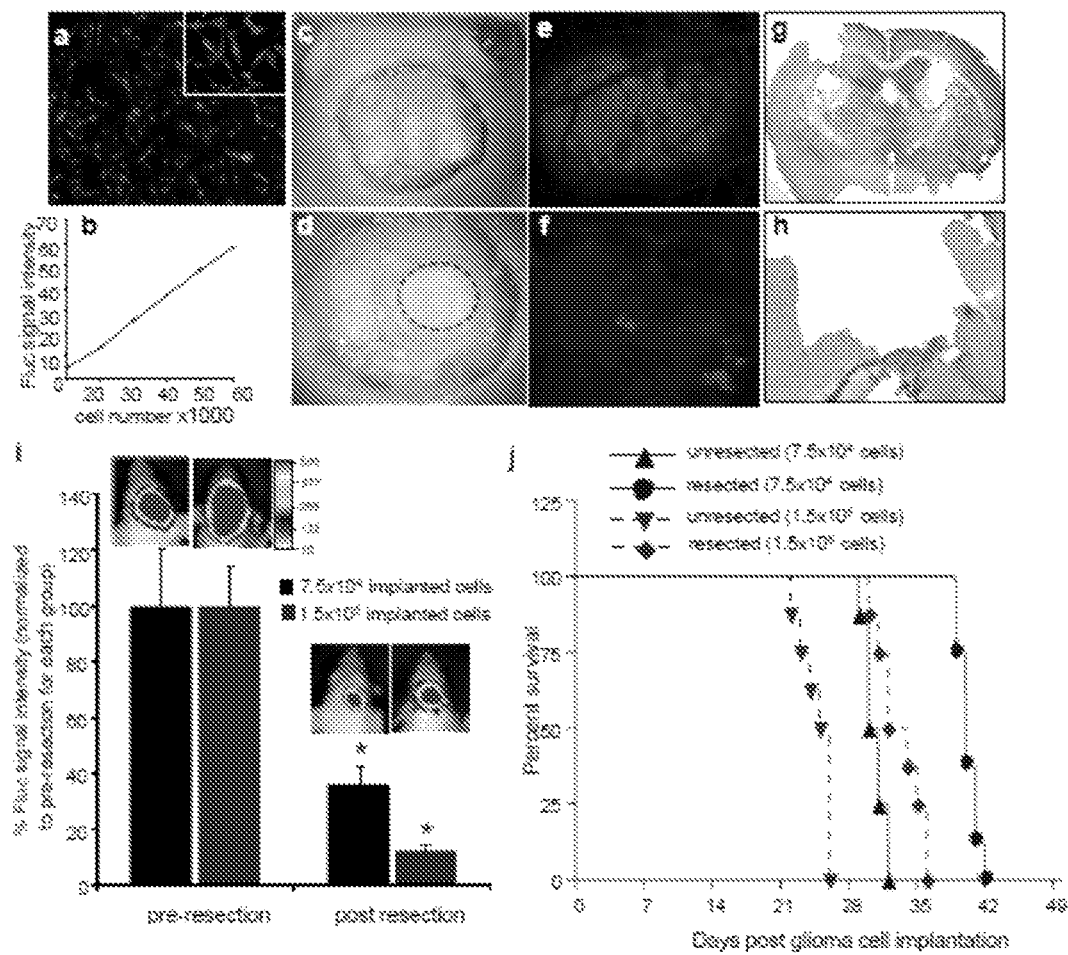
FIGS. 10A-10J demonstrate that tumor resection prolongs survival of mice bearing GBM. (10A-10B) Human U87 GBM cells were transduced with LV-Fluc-mCherry and 48 hrs later cells imaged for mCherry expression (light grey) and Fluc activity (dark grey). Photomicrograph of U87 cells expressing Fluc-mCherry (10A) and plot revealing the correlation between U87-Fluc-mCherry cell number and Fluc activity (10B) are shown. (10C-10F) A cranial window was established in mice and U87-Fluc-mCherry cells ($7.5 \times 10^4$ or $1.5 \times 10^5$) were implanted in the cranial window. Light images of the mouse skull with skin removed (10C), drilled rim around the cranial window (10D). Dashed circle indicates the tumor growing area in the cranial window. (10E-10F) Mice with established U87-Fluc-mCherry GBMs in the cranial window were injected with a blood pool agent, Anigiosense-750 and imaged by intravital microscopy. Photomicrographs pre- (10E) and post- (10F) tumor resection are shown. (10G-10H) Photomicrographs of low (10G) and high (10H) magnification H&E staining of brain sections showing tumor resection cavity. (10I) Plot of the relative mean Fluc signal intensity and representative images pre- and post-tumor resection of mice implanted with $7.5 \times 10^4$ (resected on day 14 post implantation) or $1.5 \times 10^5$ (resected on day 21 post implantation) GBM cells are shown ($p<0.05$ versus pre-resection for each group). (10J) Kaplan-Meier survival curves of mice with and without resected U87-Fluc-mCherry tumors. Scale bars, 100 µm (10A, 10E, 10F, 10H) and 400 µm (10G). Original magnifications: ×2 (10C) and ×4 (10D).
Figures 14A, 14B, 14C:
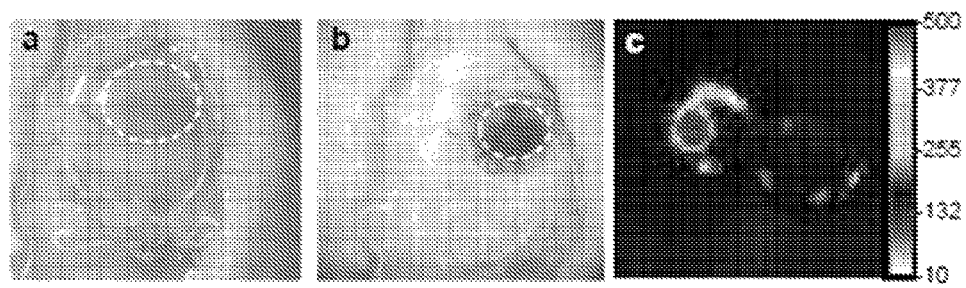
FIGS. 14A-14C depict tumor resection. U87-Fluc-mCherry tumor cells were implanted in mice with cranial window. Light images of the established intracranial U87-Fluc-mCherry tumor (14A) and the resected tumor (14B) in a cranial window. (14C) Resected U87-mCherry-Fluc tumor specimen imaged for Fluc bioluminescence. Dotted circle indicates the tumor implantation site (in 14A) and tumor resection site (in 14B).

Encapsulated Therapeutic Stem Cells Transplanted in the Tumor Resection Cavity Eradicate Brain Tumors Creating a Mouse Model of GBM Resection To develop a mouse surgical resection model of GBM, malignant GBM cells engineered with fluorescent and bioluminescent proteins were employed. Human GBM cells, U87 were transduced with lentiviral construct LV-Fluc-mCherry, sorted and screened for mCherry (FIG. 10A) and Fluc expression (FIG. 10B). A direct correlation was seen between the Fluc expression and the cell number (FIG. 10B). U87-Fluc-mCherry human GBM cells were implanted in a cranial window created by removal of a small circular portion of the skull (FIGS. 10C-10D, FIGS. 14A-14B) and mice were imaged for tumor progression/volumes over time by fluorescence intravital microscopy (IVM) and Fluc bioluminescence imaging, (FIGS. 10E, 10I). Established GBM tumors in mice generated by implantation of low ($7.5 \times 10^4$) and high ($1.5 \times 10^5$) number of GBM cells were resected and IVM and BLI imaging post resection were used to determine the extent of resection (FIGS. 10F, 10I). Fluc imaging confirmed greater than 60% of the tumor was resected in mice bearing small tumors, while over 80% of the tumor was resected in mice with large tumors that were easier to visualize (FIG. 10I, FIG. 14C). High resolution IVM and IHC confirmed the efficiency of resection (FIG. 10E-10I) and Kaplan-Meier survival curves showed a significant increase in the survival of resected tumor mice as compared to the mice with un-resected tumors in both tumor types (FIG. 10J).

Figures 11A, 11B, 11C, 11D, 11E, 11F, 11G, 11H, 11I:
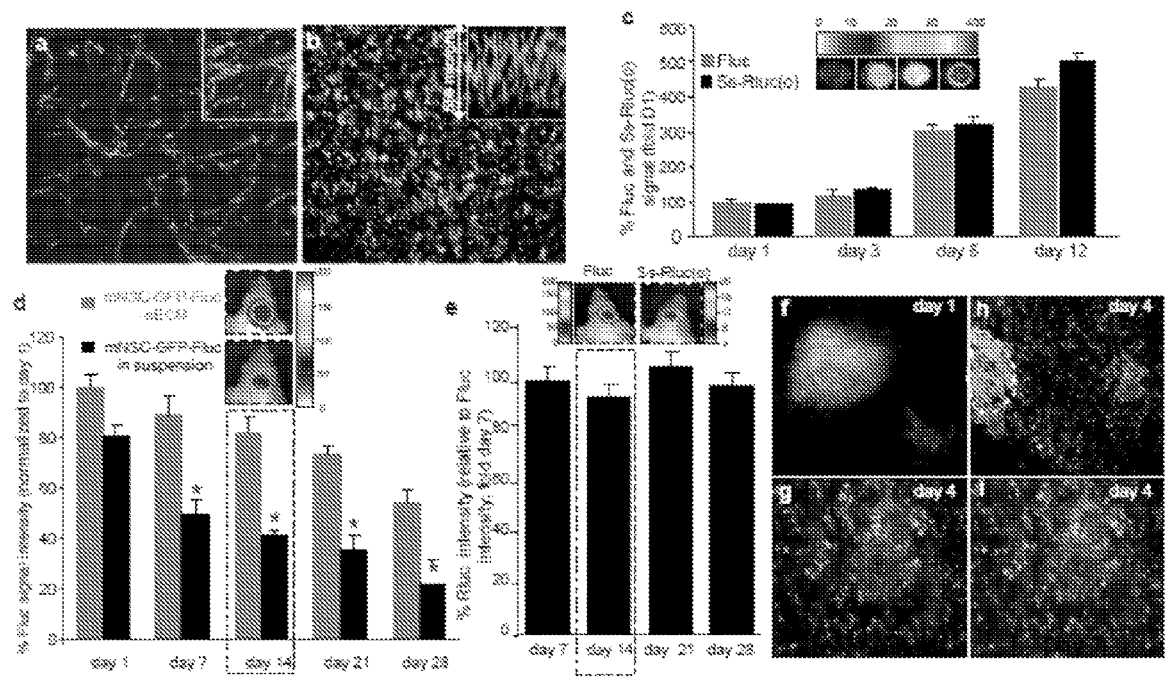
FIGS. 11A-11I depict the characterization of engineered mNSC in biocompatible sECMs in vitro and in mouse models of GBM: (11A-11B) Photomicrographs of mNSC expressing GFP-Fluc (mNSC-GFP-Fluc) grown in monolayers (11A) and encapsulated in sECM (11B). (11C) mNSC co-expressing GFP-Fluc and a secretable luciferase, Ss-Rluc (o)) were encapsulated in sECM and cell proliferation and protein secretion were followed by simultaneous Fluc and Rluc imaging of cells and culture medium respectively. Plots and representative images are shown. (11D) mNSC-GFP-Fluc in suspension or encapsulated in sECM were implanted intracranially and mice were imaged serially for mNSC survival by Fluc activity. Plot showing the mNSC survival when implanted in sECM versus suspension in the brain over a period of 4 weeks. Representative images from day 14 mice are shown (p<0.05 versus non-encapsulated mNSC). (11E) mNSC co-expressing GFP-Fluc and Ss-Rluc (o) were encapsulated in sECM, implanted intracranially and cell viability (Fluc signal) and protein secretion (Rluc signal) were followed by simultaneous Fluc and Rluc imaging in vivo respectively. Plot showing the ratio of Rluc signal intensity relative to Fluc signal intensity. Representative images from day 7 mice are shown. (11F-11I) Mice bearing U87-mCherry-Fluc GBMs in the cranial windows were implanted with mNSC-GFP-Rluc encapsulated in sECMs 1 mm away from an established tumor. GFP appears as light grey, LUC as a darker grey. Mice were imaged by intravital microscopy and photomicrographs showing mNSC and tumor cells on day 1 (11F) and on day 4 (11G,11H,11I) post mNSC implantation. Scale bars: 100 µm (11A, 11B, 11H, 11I) and 200 µm (11F, 11G). Original magnifications: ×20 (11A, 11B insets). Data are mean±s.e.m.
Figures 15A, 15B:
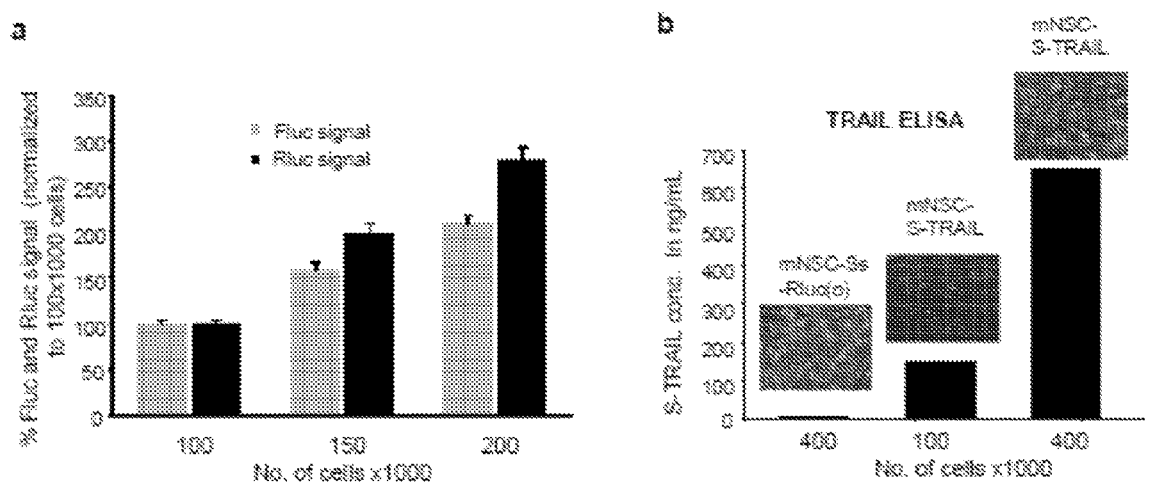
FIGS. 15A-15B depict mNSC-sECM in vitro characterization: (15A) mNSCs were either transduced with LV-GFP-Fluc or LV-Ss-Rluc(o) and different cell numbers were encapsulated in sECM and imaged for cell viability (Fluc activity) and protein secretion (Rluc(o)) activity. Plot revealing the correlation between cell number and Fluc or Rluc activity is shown. (15B) mNSCs were either transduced with LV-Ss-Rluc(o) or LV-S-TRAIL and different cell numbers were encapsulated in sECM and incubated in growth medium and 24 h later ELISA for S-TRAIL was performed on conditioned medium. Representative photomicrographs of encapsulated mNSCs expressing S-TRAIL or Ss-Rluc(o) and plot revealing the correlation between the S-TRAIL concentration in the medium and the number of encapsulated mNSCs.

Characterizing Engineered mNSC Encapsulated in Biocompatible sECMs In Vitro and In Vivo To assess survival of NSC encapsulated in sECMs in vitro, mouse (m)NSC were engineered to either express GFP-Fluc or to co-express GFP-Fluc and a secretable marker, Ss-Rluc(o) using our previously developed diagnostic lentiviral vectors (Shah et al. J Neurosci 2008, Hingtgen et al. Mol Cancer Ther 2008) (FIG. 11A). We confirmed a direct correlation between different sECM encapsulated cell numbers and Fluc activity and Rluc(o) activity in vitro (FIG. 15A). Both engineered mNSC types were encapsulated in sECMs (FIG. 11B). A stable increase in both the cell proliferation (Fluc activity) and protein secretion (Rluc activity) was seen when mNSC co-expressing GFP-Fluc and a secretable luciferase (Ss-Rluc(o)) encapsulated in sECM were cultured over-time (FIG. 11C). To assess the influence of sECMs on cell survival in vivo, mNSC-GFP-Fluc in suspension or encapsulated in sECM were implanted intracranially and mice were imaged serially for mNSC survival by Fluc activity. A significant increase in cell viability was observed in mice bearing sECM encapsulated mNSC as compared to the non-encapsulated mNSC (FIG. 11D). To longitudinally monitor mNSC expressed proteins in vivo, we intracranially implanted sECM encapsulated mNSC co-expressing GFP-Fluc and Ss-Rluc(o) in mice. In vivo, dual bioluminescence imaging showed a stable production of proteins from mNSC over-time (FIG. 11E). In order to follow migration of sECM encapsulated mNSC, mice bearing U87-Fluc-mCherry GBMs in a cranial window were implanted with mNSC-GFP-Rluc encapsulated in sECMs 1 mm away from an established tumor. Intravital imaging revealed that sECM encapsulated NSC migrate out of the sECMs and specifically home to tumors in the brain over a period of 4 days (FIGS. 11F-11I).

Figures 12A, 12B, 12C, 12D, 12E, 12F, 12G:
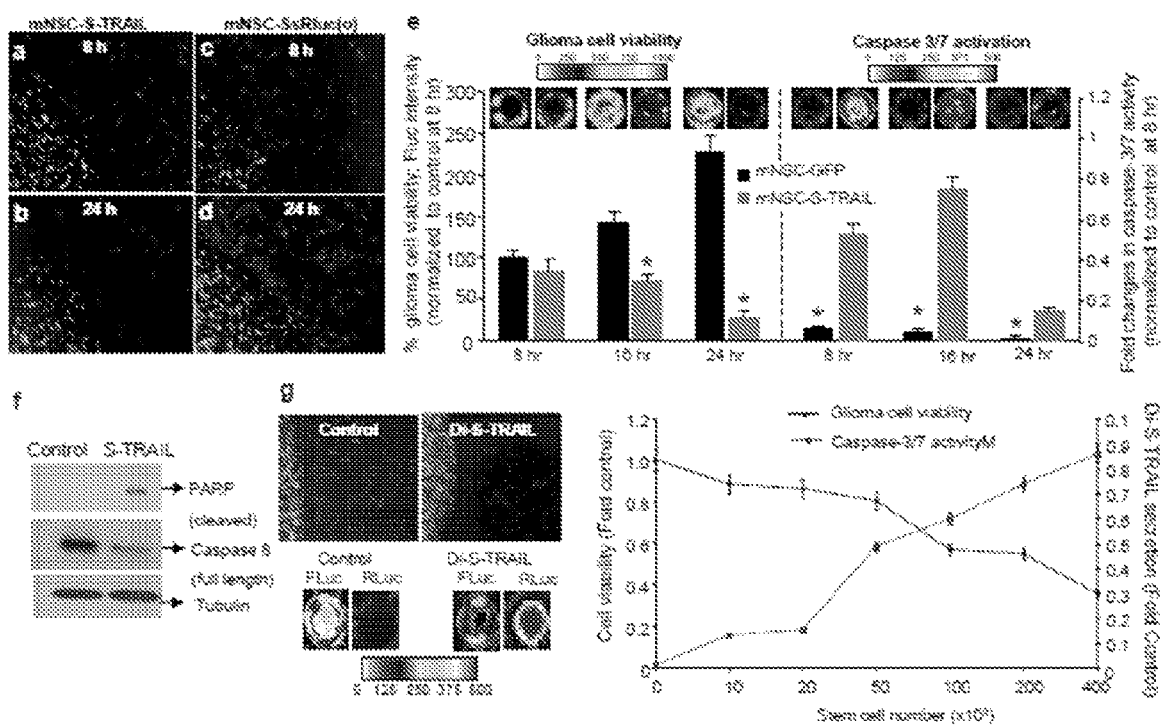
FIGS. 12A-12G depict that mNSC expressing therapeutic S-TRAIL upregulates caspase-3/7 and induces GBM cell death in vitro: (12A-12E) mNSC expressing Ss-Rluc(o) or S-TRAIL were encapsulated in sECMs and placed in the culture dish containing human GBM cells U87-Fluc-mCherry (darker grey). Photomicrographs showing sECM encapsulated mNSC at 8 (12A, 12C) and at 24 (12B, 12D) hrs. Plot showing the tumor cell viability (p<0.05 versus controls) and caspase-3/7 activation (p<0.05 versus mNSC-S-TRAIL) over 24 hours when co-cultured with either sECM encapsulated mNSC-Ss-Rluc(o) or mNSC-S-TRAIL (12E). (12F) Western blot analysis on GBM cells collected at 8 hrs post sECM encapsulated mNSC-S-TRAIL placement in the culture dish. (12G) Representative images and summary graphs demonstrating the effect of the release of Di-S-TRAIL from mNSC encapsulated sECM co-cultured with U87-mCherry-Fluc at increasing stem cell to tumor cell ratios. After 24 hrs of co-culture, levels of Di-S-TRAIL were visualized by Rluc bioluminescence imaging and tumor cell viability was visualized by Fluc bioluminescence imaging. Magnification 10× (12A-12D,12G). Data are mean±s.e.m.
Figure 19:
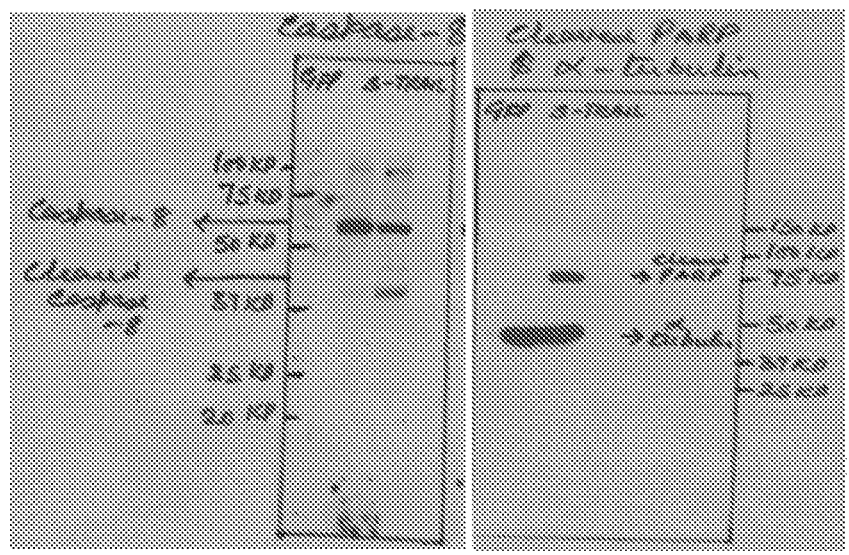
FIG. 19 depicts a western blot analysis showing uncropped Western blots of the data shown in FIG. 12F.

To assess the therapeutic potential of mNSC expressing therapeutic proteins that specifically kill tumor cells, mNSC were engineered to express S-TRAIL, a cytotoxic agent that induces apoptosis specifically in tumor cells, and its diagnostic variant Di-S-TRAIL or controls. S-TRAIL ELISA revealed high TRAIL concentration (150-650 ng/mL) in the culture medium containing mNSC-S-TRAIL cells encapsulated in sECMs (FIG. 15B). A significant reduction in GBM cell viability was seen when mNSC-S-TRAIL cells encapsulated in sECMs were placed in the culture dish containing human GBM cells U87-Fluc-mCherry (FIGS. 12A-12E). The decrease in GBM cell viability was associated with increase in caspase-3/7 activity (FIG. 12E) and changes in caspase-8 (FIG. 12F) and PARP activity (FIG. 12F, FIG. 19). S-TRAIL ELISA confirmed a high TRAIL concentration (150-650 ng ml-1) in the culture medium containing mNSC-S-TRAIL cells encapsulated in sECM (FIG. 15B). To simultaneously monitor release of S-TRAIL from sECM encapsulated mNSC and its effect on GBM cell viability in sECM encapsulated mNSC co-cultured with U87-mCherry-Fluc GBM cells, mNSC were engineered with our recently created diagnostic variant of S-TRAIL (Di-S-TRAIL). Dual bioluminescence imaging showed robust levels of Di-S-TRAIL released from sECM that increased as the stem cell/tumor cell ratio increased and resulted in a significant and dose-dependent decrease in GBM cell viability (FIG. 12G). These results demonstrate that sECM encapsulated engineered mNSC survive longer in mice brains, migrate to tumors in the brain and induce apoptosis in GBM cells.

Figures 13A, 13B, 13C, 13D, 13E, 13F, 13G:
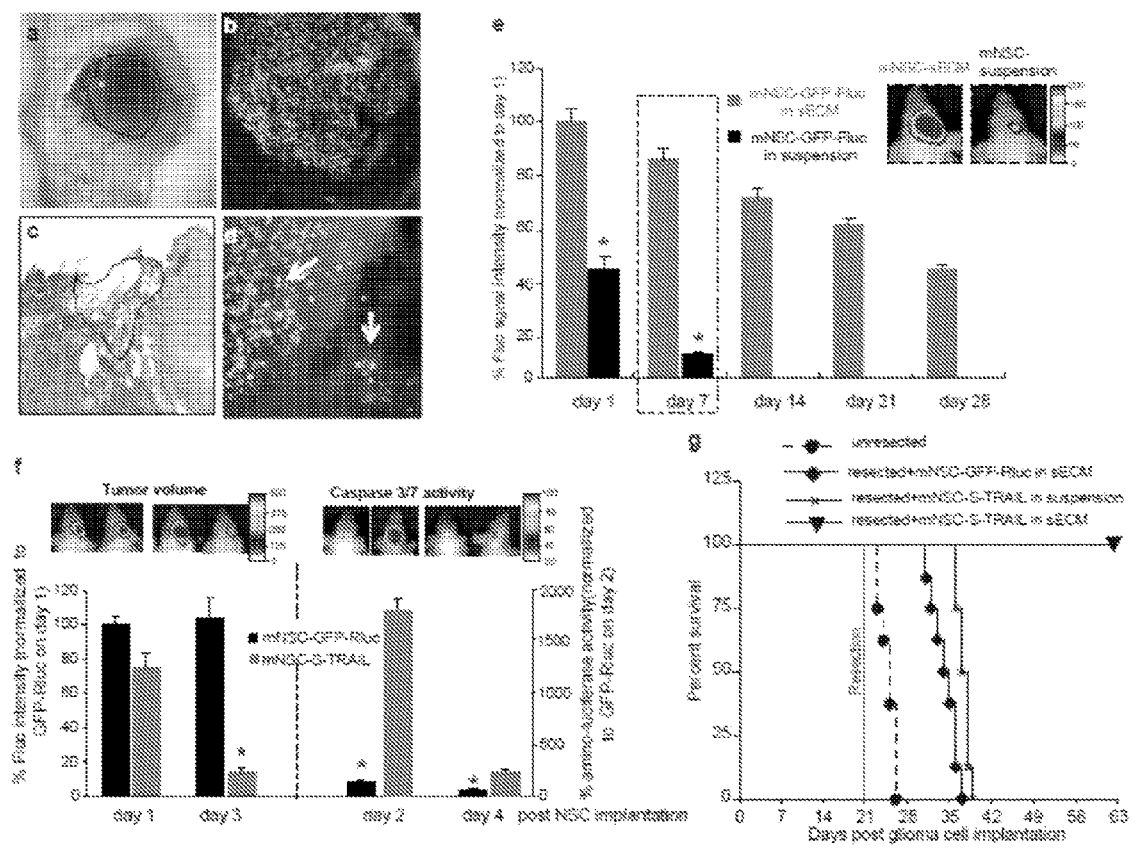
FIGS. 13A-13G demonstrate that sECM encapsulated mNSC-S-TRAIL transplanted into the tumor resection cavity increase survival of mice: (13A-13C) mNSC-GFP-Fluc in suspension or encapsulated in sECM were implanted intracranially in the resection cavity of the mouse model of resection, injected with Angiosense-750 i.v. and mice were imaged by intravital microscopy and by serial Fluc bioluminescence imaging. Photomicrographs showing the light image of the resection cavity containing sECM encapsulated mNSC (outlined area) (13A) and fluorescent (13B) and IHC image of sECM encapsulated mNSC-GFP-Fluc implanted (outlined area) in the resection cavity (13C). (13B) Fluorescence photomicrograph showing mNSCs targeting residual GBM cells in a tumor resection cavity with leaky vasculature. (13C) Hematoxylin and eosin image of sECMencapsulated mNSC-GFP-Fluc cells implanted (outlined area) in the resection cavity. (13D) Higher magnification fluorescence photomicrograph showing mNSCs targeting residual GBM cells indicated by arrows in a tumor resection cavity with leaky vasculature. (13E) Plot and representative figures of the relative mean Fluc signal intensity of mNSC-GFP-Fluc in suspension or encapsulated in sECMs placed in the GBM resection cavity (p<0.05 versus encapsulated mNSC). (13F-13G) mNSC-S-TRAIL or mNSC-GFP-Rluc encapsulated in sECM or mNSC-S-TRAIL in suspension were implanted intracranially in the resection cavity of the mouse model of resection and mice were followed for changes in tumor volume by serial Fluc bioluminescence imaging after aminoluciferin and luciferin injections, respectively, and for survival. TRAIL mediated caspase-3/7 activation and changes in tumor volumes (13G) as assessed by bioluminescence imaging Kaplan Meier survival curves (13F) are shown. Magnification 4× (13A, 13B) 10× (13C, 13D). (In panel 13F, tumor volumes: p<0.05 versus controls; and caspase 3/7 activity: p<0.05 versus mNSC-S-TRAIL)
Figure 16:
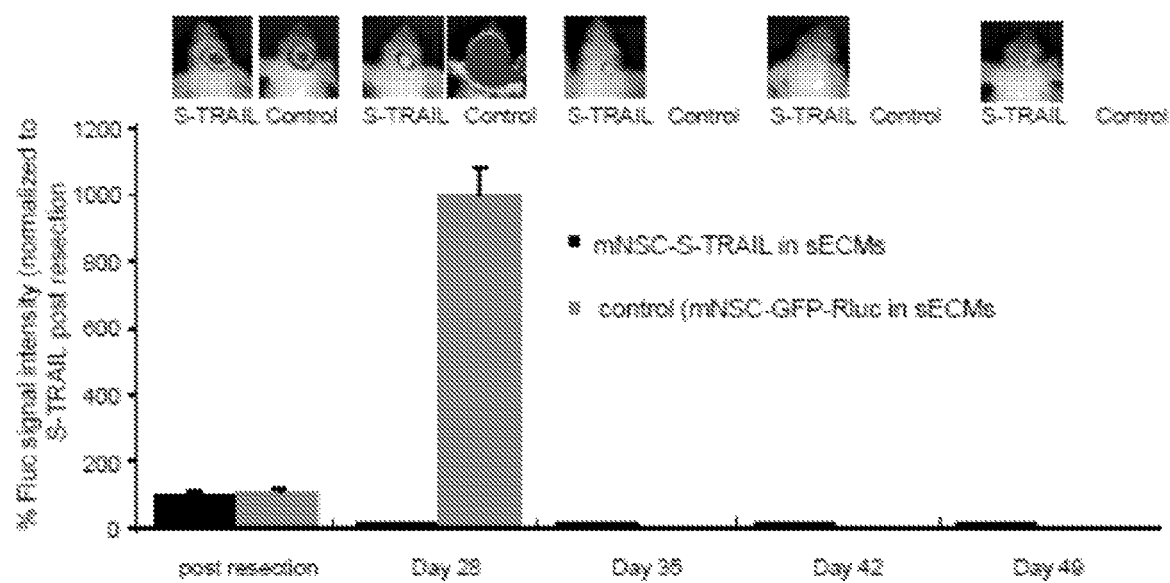
FIG. 16 demonstrates that mNSC expressing therapeutic S-TRAIL placed in the resection cavity reduces the tumors mean Fluc signal intensity over time. Mice were implanted with U87mCherry-Fluc glioma cells in a cranial window, resected and implanted with sECM encapsulated mNSC-S-TRAIL or mNSC-GFP-Rluc. Mice were followed for changes in tumor volume by serial Fluc bioluminescence imaging. Plot reveals the % Fluc signal intensity post tumor resection over 49 days. Representative images are shown. *p<0.05 versus controls at day 28; determined by students t test; data are mean±s.e.m.

Transplantation of 'Armed' mNSC into the Tumor Resection Cavity and In Vivo Imaging of Tumor Regression To assess survival of mNSC encapsulated in sECMs in vivo in mouse models of resection, mNSC-GFP-Fluc were implanted either in suspension or encapsulated in the resection cavity of U87 GBMs. sECM encapsulated mNSC were retained in the tumor resection cavity (FIGS. 13A-13C) at high local concentrations adjacent to the residual tumor cells (FIG. 13D). sECM encapsulated mNSC survival in the tumor resection cavity over a period of 1 month was significantly higher as compared to the non-encapsulated mNSC in the resection cavity (FIG. 13E). Next, to assess the therapeutic potential of sECM encapsulated mNSC-S-TRAIL in mouse resection models of GBM, sECM encapsulated mNSC-S-TRAIL or mNSC-GFP-Rluc were implanted intracranially in a resection cavity of the mouse model of resection and mice were followed for changes in tumor volume by serial Fluc bioluminescence imaging and for survival. As shown in FIG. 13F, sECM-encapsulated mNSC-S-TRAIL induced a dramatic increase in caspase-3/7 activity and greater than an 80% decrease in residual tumor cells as early as 3 days post-seeding that could be followed by simultaneously visualizing caspase-3/7 activation and tumor volumes in real time in vivo. Importantly, sECM-mNSC-S-TRAIL suppressed re-growth of residual tumor cells through 49 days post-resection (FIG. 16). Highlighting the survival benefit of this approach, mice treated with control sECM-encapsulated mNSC-GFP-Rluc demonstrated a median survival of 14.5 days GBM post-resection. In contrast, 100% of mice treated with mNSC-S-TRAIL encapsulated in sECM after GBM resection were alive 42 days post-treatment (FIG. 13G). sECM encapsulation was required for the survival benefit, as mNSC-S-TRAIL delivered in suspension into the resection cavity showed no significant increase in survival (FIG. 13G). These results demonstrate that sECM encapsulated therapeutic mNSC are retained in the tumor resection cavity, result in killing of residual GBM cells that significantly increase survival of mice.

Figures 17A, 17B, 17C, 17D, 17E, 17F, 17G, 17H, 17I, 17J, 17K, 17L:
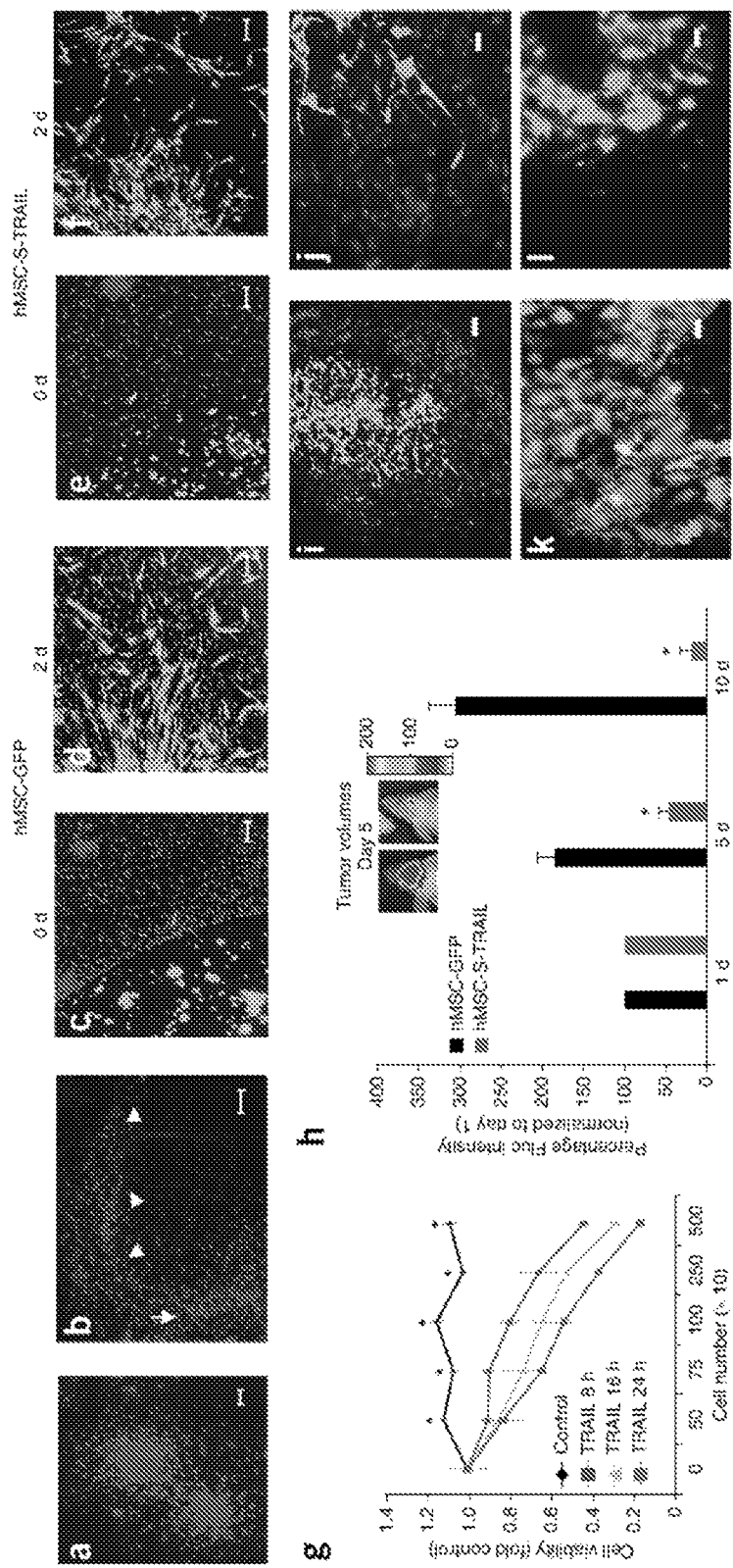
FIGS. 17A-17L demonstrate that ECM-encapsulated therapeutic human MSCs have anti-tumor effects on primary invasive human GBMs in vitro and in vivo. (17A, 17B) Primary invasive GBM8-mCherry-Fluc cells grown as neurospheres in a collagen matrix (17A) and brain section of mice bearing GBM8-mCherry-Fluc tumors, showing the highly invasive nature of GBM8 (17B). Arrow, site of implantation; arrowheads, path of invasion. (17C-17G) hMSCs expressing GFP or S-TRAIL were encapsulated in sECM and placed in a culture dish containing human GBM8-Fluc-mCherry cells. hMSCs were followed for migration out of sECM, and GBM8 cells were followed for their response to S-TRAIL secreted by hMSCs. Photomicrographs show sECM-encapsulated hMSCs on the day of plating (17C, 17E) and 48 h after plating (17D, 17F). (17G) GBM8 cell viability at different time points after culturing with varying numbers of either sECM-encapsulated hMSC-GFP (control) or hMSC-S-TRAIL (TRAIL) cells. *P<0.05 versus TRAIL at 8 h, 16 h and 24 h. (17H-17J) Encapsulated hMSC-S-TRAIL or hMSC-GFP cells in sECM were implanted intracranially in the tumor resection cavity of mice bearing GBM8-mCherry-Fluc cells and mice were followed for changes in tumor volume by serial Fluc bioluminescence imaging and correlative immunohistochemistry. Plot and representative images show the relative mean Fluc signal intensity from mice bearing sECM-encapsulated hMSC-GFP or hMSC-S-TRAIL cells. *P<0.05 versus control (17H). (17I, 17J) Low-magnification (17I) and high-magnification (17J) photomicrographs of serial brain sections of mice showing hMSCs on day 5 after hMSC implantation in the GBM8 resection cavity. (17K, 17L) Representative images showing cleaved caspase-3 staining (purple) on brain sections from mice implanted with hMSC-S-TRAIL cells (17K) and control cells (17L) 5 d after treatment. Scale bars: 100 μm (17A, 17C-17F, 17I), 200 μm (17B) and 50 μm (17J-17L). Data are mean±s.e.m.
Figure 20:
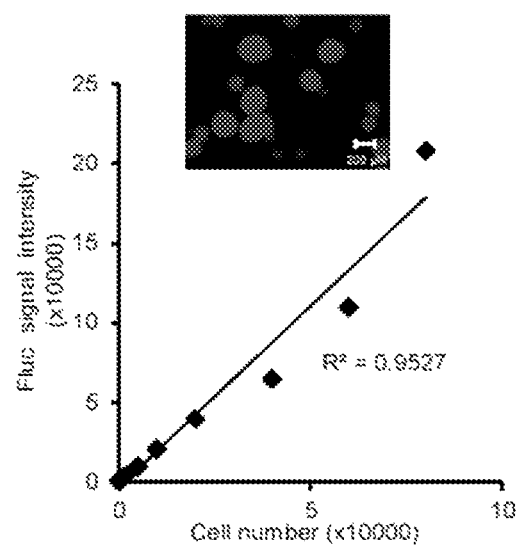
FIG. 20 demonstrates engineered human GBM8 cells for in vitro and in vivo studies. Regression analysis indicating linear correlation between primary human GBM8 cells expressing Fluc-mCherry cell number and Fluc activity. Representative photomicrograph of GBM8-mCherry-Fluc cells in culture is shown. Data was derived from the experiments performed in triplicate.

Several studies have shown that freshly isolated primary glioma lines from clinical specimens more accurately recapitulate the clinical scenario of GBMs. To assess the clinical relevance of sECM-encapsulated stem cell-based therapeutic regimen in a more clinically relevant model, we used a TRAIL-sensitive primary human invasive glioma line, GBM8, and human bone marrow-derived MSCs (hMSCs). We engineered GBM8 cells to express a mCherry-Fluc fusion protein and showed that the GBM8-mCherry-Fluc line retained the tumor cell invasive properties of the parental line in culture (FIG. 17A) and in vivo (FIG. 17B). There was a direct correlation between the Fluc signal intensity and the number of cells in vitro in the ranges tested (FIG. 20). To assess the migration and the therapeutic potential of hMSCs expressing therapeutic proteins that specifically kill tumor cells, we engineered hMSCs to express GFP or S-TRAIL and GFP. In cultures of sECM-encapsulated hMSCs with GBM8 cells, hMSCs expressing GFP only or S-TRAIL migrated out of the sECM and tracked GBM8 cells (FIGS. 17C-17F). Furthermore, hMSC-S-TRAIL cells induced GBM8 cell death in a time- (FIG. 17G) and caspase-3/7-dependent (2.7±0.1 fold increase in caspase-3/7 activity in comparison to hMSC-GFP cells) manner. Next, to assess the therapeutic potential of sECM-encapsulated hMSC-S-TRAIL cells in mouse resection models of primary GBM8 tumors, we implanted sECMencapsulated hMSC-S-TRAIL or hMSC-GFP cells intracranially in a GBM8 tumor resection cavity and followed mice for changes in tumor volume by serial Fluc bioluminescence imaging. The presence of sECM-encapsulated hMSC-S-TRAIL cells resulted in significantly less residual GBM8 cells than in the controls (FIG. 17H). Fluorescence imaging of brain sections revealed the presence of encapsulated hMSCs in the tumor resection cavity and also indicated hMSCs migration to invading glioma cells (FIGS. 17I-17J). Histopathological analysis on brain sections revealed a significantly higher number of cleaved caspase-3-positive cells in hMSC-S-TRAIL-treated mice than in controls (FIGS. 17K-17L; 4.2±0.2 fold increase in the hMSC-S-TRAIL group versus the hMSC-GFP group). These results show that sECM encapsulated engineered human MSCs have therapeutic benefits against primary tumor-derived GBMs.

Conclusions

In this Example, diagnostic and therapeutic mNSCs encapsulated in sECM were tested in a murine model of GBM resection. As demonstrated herein, sECM encapsulation of mNSC significantly increased retention time in the GBM resection cavity, permitted robust tumor-selective migration and allowed secretion of anti-tumor proteins from the sECM encapsulated stem cells in vivo. Mimicking the clinical scenario of GBM resection and subsequent treatment, TRAIL-secreting sECM encapsulated mNSC transplanted in the resection cavity eradicated residual tumor cells, delayed tumor re-growth and significantly increased survival of mice. Furthermore, we demonstrate herein that TRAIL-secreting sECM-encapsulated stem cells transplanted in the resection cavity significantly delayed tumor regrowth in mice bearing both established (U87) and primary invasive (GBM8) GBMs and significantly increased survival of mice bearing established GBMs.

The clinical standard of care for patients suffering from glioblastoma includes surgical debulking (Wen and Kesari, N Engl J Med 2008, Minniti et al. J Neurooncol 2008, Bidros and Vogelbaum Neurotherapeutics 2009), yet nearly all pre-clinical models focus on treating established solid tumors. Previously, a limited number of studies have shown the feasibility of resecting established GBMs in different animal models (Akbar et al. J Neurooncol 2009, de Oliveria et al. Neurooncol 2009). In this study, by integrating fluorescent and bioluminescent markers and extensive optical imaging, we simultaneously confirmed the presence of established tumors, visualized the extent of tumor resection and serially monitored tumor re-growth post-resection. The inclusion of post-resection bioluminescence imaging permitted gross assessment of total tumor removal, while real-time fluorescent microscopy permitted visualization of residual tumor cells and associated blood vessels in resected tumors. In recent years, in addition to the established GBM lines, human brain tumor tissue has been isolated and utilized for pre-clinical studies (Pandita et al. Genes Chromosomes Cancer 2004, Piccirillo et al. J Mol Med 2009, Wakimoto et al. Cancer Res 2009). In developing this study, the use of both established and primary tumor lines that have previously extensively characterized for invasiveness and resistance/sensitivity to TRAIL mediated apoptosis was considered (Hingtgen et al. Mol Cancer Ther 2008, Kock et al. Neoplasia 2007, Sasportas et al. Proc Natl Acad Sci 2009, Pandita et al. Genes Chromosomes Cancer 2004, Wakimoto et al. Cancer Res 2009, Baci-Onder et al., Cancer Res 2010). U87 human glioma cells were utilized in this study for several reasons. The minimal invasiveness of U87 lead to solid intracranial tumors that was essential for resection of the primary mass while allowing residual tumor cells to remain and drive recurrence. Further, the ability of NSC to track U87 (Ehtesham et al. Cancer Res 2002, Jurvansuu et al., Cancer Res 2008) permitted assessment of NSC migration out of the sECM towards GBM micro-deposits. In addition, the sensitivity of U87 to TRAIL-induced apoptosis (Hingtgen et al. Mol Cancer Ther 2008) was vital for determining the therapeutic potential of sECM-encapsulated therapeutic stem cells. Lastly, the robust expression of fluorescent and bioluminescent transgenes following lentiviral transduction by U87 (Hingtgen et al. Mol Cancer Ther 2008, Kock et al. Neoplasia 2007) was essential for the quantitative image-guided resection and tracking the response or tumors to stem cell therapy reported in this study.

Despite extensive pre-clinical evidence demonstrating the potential of cell-based therapy for GBM, no preclinical studies have explored methods to introduce therapeutically "armed" stem cells in GBM resection cavities. This is vital in order to prevent the stem cell "wash-out" and rapid diffusion from the resection cavity by CSF while allowing release of anti-tumor proteins directly into the resection cavity from the transplanted stem cells. Biodegradable sECM formulations are an attractive approach for retention of stem cells in the resection cavity. Previous studies have shown that biodegradable sECM increase the viability of mNSC and their differentiation into neurons in vitro (Pan et al. J Neurosci Res 2009). Recent in vivo studies illustrate transplanted biodegradable scaffolds containing stem (and other neuronal) cells in models of degeneration and hypoxia-ischemia (Orive et al., Nat Rev Neurosci 2009).

In this study sECMs were employed that are based on a thiol-modified hyaluronic acid (HA) and a thiol reactive cross-linker (polyethylene glycol diacrylate) which provides biocompatibility, physiological relevance, and customizability (Xu et al. Prostaglandin Other Lipid Mediat 2009). Additionally, release profiles of sECM used in this study were ideal to permit both migratory stem cells and secreted therapeutic proteins to exit the sECM. These events were confirmed by serial monitoring of diagnostic markers (luciferase and fluorescence) which revealed extensive migration of mNSC out of sECMs towards GBM while secreting high levels of diagnostic proteins. sECM encapsulation dramatically increased the survival of mNSC in resection cavities as compared to non-sECM encapsulated cells over a period of 4 weeks. Without wishing to be bound or limited by theory, the increased survival of sECM encapsulated mNSC is related to the fact that encapsulation can enhance survival of transplanted cells by providing a physiologically relevant environment that promotes attachment to reduce anoikis-mediated death, cell diffusion, and protection from the host immune system (Laflamme et al., Nat Biotechnol 2007, Mooney and Vandenburgh, Cell Stem Cell 2008, Terrovitis et al., J Am Coll Cardiol 2008, Zvibel et al., Cell Transplant 2002). We demonstrate herein that sECM encapsulated engineered mNSC are effective by way of increasing the concentration of therapeutic stem cells at the site of tumor resection to extend the drug exposure time to tumor cells. As long-term survival of NSC in mice brains was critical in order to fully evaluate the therapeutic effects of encapsulated therapeutic NSC, primary mouse NSC were utilized as opposed to human NSC.

The ability of TRAIL to selectively target tumor cells while remaining harmless to most normal cells makes it an attractive candidate for an apoptotic therapy for highly malignant brain tumors. However, sustained levels of TRAIL are key to improving the efficiency and potency of TRAIL-based pro-apoptotic cancer therapy. It has been shown that mNSC do not express TRAIL receptors and are insensitive to TRAIL mediated apoptosis. Using a diagnostic variant of S-TRAIL, the results shown herein clearly reveal that mNSC secreted S-TRAIL is released from sECMs and induces caspase-3 mediated apoptosis in brain tumor cells in vitro. When encapsulated into sECMs and implanted into resected GBM tumors, mNSC-S-TRAIL results in a significant increase in survival of mice bearing GBMs. These results confirm that TRAIL is a potent inhibitor of brain tumor growth, and that encapsulated mNSC-S-TRAIL cytotoxic therapy is highly efficient in inducing apoptosis in residual GBM cells in our mouse model of GBM resection. Furthermore, stem cells have the advantage of offering a continuous and concentrated local delivery of secretable therapeutic molecules like TRAIL, thus reducing non-selective targeting, and allowing higher treatment efficiency and potency for a longer time period. These results demonstrate that ECM encapsulation of mNSC-S-TRAIL is a new approach for delivering cytotoxic therapies to GBM and have the potential to improve patient outcomes.

Figure 18:
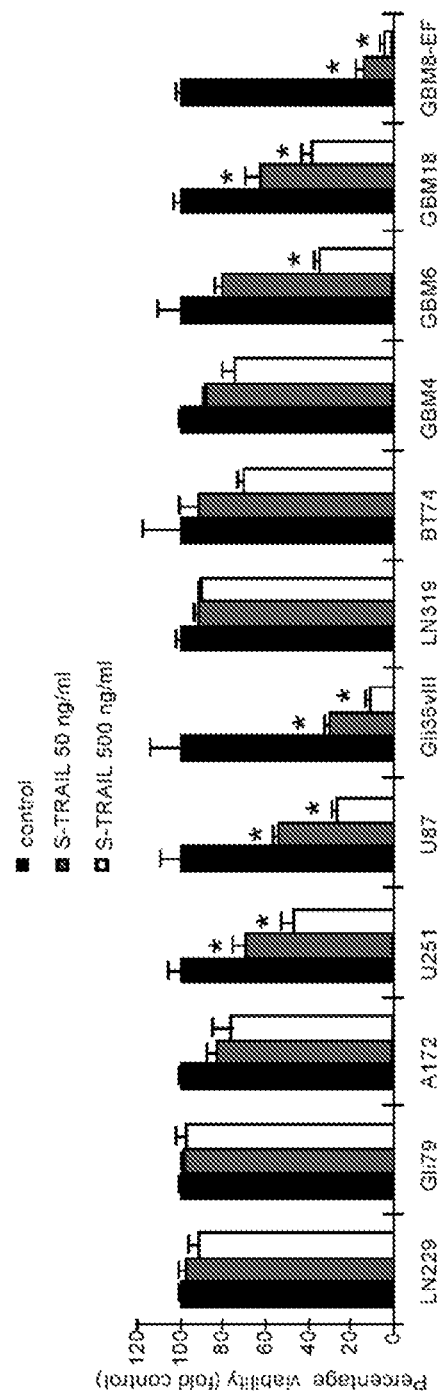
FIG. 18 demonstrates sensitivity/resistance of GBM cells to TRAIL mediated apoptosis: Different established GBM (LN229, Gli79, A172, U251, U87, Gli36vIII, LN319) and primary GBM (BT74, GBM4, GBM6, GBM18, and GBM8-EF) lines were incubated with different concentrations of S-TRAIL, and GBM cell viability was determined 24 h postincubation. Plot revealing the percentage cell viability is shown. *p<0.05 versus control determined by ANOVA; data are mean±s.e.m.

Although TRAIL is a selective and potent anti-tumor agent, many tumor lines, including some established GBM lines, have varying resistance or sensitivity to TRAIL-induced apoptosis, with about 50% of already established GBM lines being resistant to TRAIL (see FIG. 18, for example). Although therapy with sECM-encapsulated TRAIL-secreting stem cells is efficacious for TRAIL-sensitive GBMs, many GBM tumors are likely to be fully resistant to TRAIL-based therapies. To address GBMs that are fully resistant to TRAIL, sensitizing TRAIL resistant GBM cell lines to TRAIL-mediated apoptosis by treatment can be accomplished with agents including, for example, temozolomid, protease inhibitors, cisplatin, proteasome inhibitors, and daidzein. Recent in vivo studies have shown that treatment with irradiation followed by TRAIL-secreting umbilical cord blood-derived MSCs synergistically enhances apoptosis in TRAIL-sensitive and TRAIL-resistant GBM. In addition, stem cells can be engineered to simultaneously secrete different therapeutic proteins that target multiple pathways in GBMs, in some embodiments. Along these lines, we have engineered stem cells to secrete an antiangiogenic agent consisting of three type-1 anti-angiogenic repeats of thrombospondin-1 (aaTSP-1) and shown in a recently published study that prolonged release of aaTSP-1 from stem cells in mice bearing gliomas targets GBM-associated vasculature and increases mouse survival (Van Eekelen, M. et al. Human stem cells expressing novel TSP-1 variant have antiangiogenic effect on brain tumors. Oncogene 29, 3185-3195 (2010)). As TSP-1 is known to normalize vasculature and upregulate death receptors DR4 and DR5 on tumor associated endothelial cells, the use of stem cells expressing both TRAIL and TSP-1, in some embodiments, can be used to augment TRAIL-mediated apoptosis in both GBM cells and associated endothelial cells.

The limited availability of non-invasive methods to monitor multiple molecular events has been one of the main limitations in testing the efficacy of various tumor therapy paradigms. In previous studies, it has been have shown that delivery of viruses (Shah et al. Oncogene 2003), NSC (Shah et al. Ann Neurol 2005) can be followed and GBM burden in vivo can be quantified (Shah et al. Ann Neurol 2005, Kock et al. Neoplasia 2007, Shah et al. Oncogene 2003) using non-invasive bioluminescence imaging. However, combining bioluminescence imaging and confocal intravital microscopy offers great potential to image multiple events in real time. As shown herein, tumor cells and stem cells can be labeled with bimodal imaging markers (bioluminescent and fluorescent) expressed as a single transcript, which allows for expanding the number of events that can be visualized in real-time in vivo and efficiently applied bioluminescence imaging to follow both un-resected and resected intracranial tumors and the fate of NSC in vivo. To follow pharmacokinetics of therapeutic S-TRAIL both in culture and in mouse models of GBM, a N-terminal fusion of S-TRAIL with Rluc(o) has been employed, which was engineered and characterized for its extracellular functionality. In addition, a blood pool agent, angiosense-750, has been used to visualize the tumor associated vasculature. Clearly, the inclusion of non-invasive molecular imaging allows characterization of multiple events in sECM-NSC therapy with enhanced spatial and temporal resolution.

In recent years, primary GBM lines have been created from isolated human brain tumor tissue and used for preclinical studies. Several studies have shown that xenografts of these primary cell lines often recapitulate clinical GBM more faithfully than established GBM cell lines, thus providing more insights and a more stringent test of promising new anti-GBM therapies. In developing the studies described herein, we initially used an established glioma line, U87, that our laboratory and others have extensively characterized for in vivo tumor formation and assessment of target therapeutics in mouse models of brain tumors. Most of the established glioma lines, including U87, form solid intracranial tumors in most cases. This was essential for resection of the primary mass and for study of the effect of sECMencapsulated mouse stem cells on the residual tumor cells after resection. However, to test the efficacy of sECM-encapsulated stem cell therapy in mouse models of GBM that recapitulate all the features of the human cancer, we used the primary cell line GBM8. We and others have shown GBM8 cells form highly invasive tumors upon intracerebral implantation into mic, thus recapitulating most of the features of human GBM. Although primary invasive lines are more predictive, they introduce the technical difficulty of resecting invasive tumor cells from the brain. To circumvent this, we implanted ten times as many GBM8-mCherry-Fluc cells as used by us in previous reports to create an initial solid tumor mass which could then be resected. In addition to a more clinically relevant tumor model, we also used bone marrow-derived hMSCs that have been extensively used in past and ongoing clinical trials and offer the potential of autologous transplantation, thus overcoming the limitation of immune rejection. Pairing the clinically relevant GBM and hMSC lines allowed us to perform extensive studies investigating the effect of encapsulated therapeutic hMSCs in invasive mouse model of GBM resection. Our results described herein clearly demonstrate that hMSC-S-TRAIL cells rapidly attenuated progression of GBM8 tumors in the brains of mice.

Although most studies, including our previous studies in mouse models of GBM, have shown that human bone marrow-derived MSCs offer the potential of autologous transplantation and have antitumor therapeutic potential, some studies have suggested tumor-promoting properties in mouse tumor model, and mass formation in an experimental autoimmune encephalomyelitis model in mice. As the tumorigenic potential of different stem cell types is a concern, the use of alternative stem cell sources, including adipose tissue-derived MSCs49 and skin-derived reprogrammed induced pluripotent NSCs (Mattis, V. B. & Svendsen, C. N. Induced pluripotent stem cells: a new revolution for clinical neurology? Lancet Neurol. 10, 383-394 (2011).) from patients, can be used in some embodiments of the compositions and methods described herein. In some embodiments, the incorporation of suicide genes, such as HSV-TK, into therapeutic human stem cell types can be used to allow the eradication of therapeutic stem cells after GBM treatment.

The studies shown herein reveal the fate and therapeutic efficacy of engineered and sECM encapsulated mNSC in a mouse model of GBM resection. Using the compositions and methods described herein, advances can be made in the way stem cells can be engineered and used clinically in brain tumor patients. In some embodiments of the methods described herein, neurosurgical removal of the main tumor mass at the time of surgery can be combined with implantation of patient's own reprogrammed cells or mesenchymal stem cells, therapeutically engineered with anti-tumor agent (s) and encapsulated in sECM, into the resection cavity of the tumor. These cells would result in killing of both residual and invasive tumor cells with the ultimate goal of improving patient outcomes. The results shown herein also have a major impact in translating stem cell based therapies for the treatment of a number of other brain pathologies.

Example 3

Additional Multimodal TRAIL Agents

Path to Clinics Using Multimodal Molecules

The HSV-TK (Herpes simplex virus-thymidine kinase) gene has been explored as a reporter and/or suicide gene previously. Both gene therapy with HSV-TK and the use of this gene as a marker are currently applied in patients with various forms of cancer. Specifically, therapy has been performed by intratumoral injection of HSV-TK carriers (like viruses) followed by systemic ganciclovir injection and noninvasive positron emission tomography (PET) imaging of HSV-TK expression has been performed by using [$^{18}$F] FHBG (a fluorine-18 labeled penciclovir analog) radiotracer.

Based on our multimodal TRAIL agent molecule, Rluc (o)TRAIL, described herein is a multimodal molecule that can be used in clinical settings. Specifically, this can involve fusion of a secretable HSV-TK to the N-terminus of TRAIL to create a HSV-TK-TRAIL. This molecule can have enhanced cancer cell killing properties because of the expression of both HSV-TK and TRAIL and in addition to diagnostic properties that allow it to be tracked in mouse models of different cancers by either delivering it systemically as a purified protein or via stem cells as a secretable protein.

Characterizing HSV-TK(L2)TRAIL in Culture and In Vivo

Generation of lentiviral vectors: Lentiviral vectors, pLV-CSC-IG bearing an IRES-GFP (Internal ribosomal entry site-green fluorescent protein) element can be used as a backbone and all restriction sites can be engineered into the primers. To generate fusion secretable HSV-TK and S-TRAIL fusion proteins, HSV-TK are initially PCR amplified with forward primers including the 60 bp signal sequence of Flt3-ligand using LV-HSV-TK DNA as template. In addition S-TRAIL can be PCR amplified including signal sequence of Linker 2 (L2) (as described herein) as the forward primer and using LV-S-TRAIL as template. HSV-TK cDNA can be N-terminally fused to S-TRAIL cDNA and cloned into pLV-CSC-IG, thus resulting in a LV-HSV-TK(L2)TRAIL construct. This lentiviral construct can be packaged into virions in 293T/17 cells using a helper virus-free packaging system as described previously.

Characterization of LV-HSV-TK(L2)-TRAIL in vitro and in vivo: All the experiments designed for Rluc(O)TRAIL fusion protein described herein can be performed. In this study, the bioluminescence imaging, as described herein can be replaced with PET imaging both in vitro and in vivo which is described below.

In vitro assay: The activity of the TK fusion proteins in the crude cell lysates of mammalian cells (293T and NSC expressing HSV-TK(L2)TRAIL can be determined using [18F]FHBG as a substrate. Since cell culture medium may contain free thymidine, all samples for enzyme activity assays can be pre-treated with 80 units thymidine phosphorylase for 30 min at 378 C, to hydrolyze any thymidine that could inhibit the TK reaction with [18F]FHBG. TK activity will be determined by incubating [18F]FHBG in the reaction mixture at 378 C (0.17 nM, specific activity, 54,000 GBq/mmol). Samples of this mixture are loaded on a Whatman DE-81 filter at different time points 25 ml. The negatively charged phosphorylated [18F]FHBG can be bound to these filters. Each filter will be washed three times and radioactivity of the filters can be counted with a gamma counter. At the end of the experiment, 50 ml of reaction mixture can be loaded on a filter and the activity of this filter is measured without washing (reflects both unchanged and phosphorylated [18F]FHBG). The unwashed filter can be used to normalize the activity bound on the washed filters. [18F]FHBG phosphorylation can be calculated by dividing the radioactivity (cpm) of the washed filters by the radioactivity of the unwashed filters.

In vivo PET imaging: Mice bearing tumors can be either injected intravenously with purified HSV-TK(L2)TRAIL or NSC expressing HSV-TK(L2)TRAIL as described for Rluco(L2)TRAIL and in vivo PET imaging can be performed after the intravenous administration of 18F-FHBG (3764 MBq) given 24 hrs after HSV-TK(L2)TRAIL administration. PET can be performed at 3 h after the intravenous administration of the label. Two emission images of 10 min each can be acquired at 30 min and 4 h later. After acquisition of the emission data, a transmission scan can be performed in a single mode using a rotating 370-MBq 137Cs source placed outside the field of view. To determine the site of the 18F-FHBG activity, color-coded coronal emission images can be superimposed on inverted gray-scaled transmission images. PET imaging can be performed every week for a period of 1 month. After each imaging session, the mice can be euthanized and their brains harvested and placed into a well automatic g-counter (1480 Wizard 3"; Wallac/PerkinElmer).

Assessing therapeutic efficacy of HSV-TK(L2)TRAIL in vivo: In order to compare the therapeutic efficacy of TRAIL and HSV-TK(L2)TRAIL in mice bearing gliomas, mice can be implanted in NSC expressing either S-TRAIL or HSV-TK(L2)TRAIL and changes in tumor volumes can be followed by Fluc bioluminescence imaging as described herein.

Materials and Methods

Generation of Lentiviral Vectors

Lentiviral vectors, pLV-CSC-IG bearing an IRES-GFP (Internal ribosomal entry site-green fluorescent protein) element (Sena-Esteves et al J Virol Methods 2004), were used as a backbone and all restriction sites were engineered into the primers. To generate the fusions LV-TRFL, LV-TRRL, and LV-TRGp, S-TRAIL and luciferases were PCR amplified using LV-S-TRAIL (Shah et al Cancer Res. 2004), LV-GFP-Fluc (Shah et al. 2008), LV-RLuc-DsRed2 (Shah et al. 2008), or pGLuc-Basic (New England Biolabs, Ipswich Mass.) respectively as templates. The resulting S-TRAIL fragment was digested with NheI and BamHI, while luciferase fragments were digested with BamHI/XhoI. Both fragments were ligated in-frame into NheI/XhoI digested pLV-CSC-IG vector. LV-GpTR, LV-$GpL_1$ TR, and LV-$GpL_2$TR were created by PCR amplification of GpLuc and digestion with NheI and EcoV. The S-TRAIL fragment was PCR amplified and 2, 6, or 12 amino acid linkers were incorporated into the S-TRAIL forward primer. The resulting S-TRAIL fragment was digested with EcoV/XhoI and both fragments ligated into NheI/XhoI digested pLV-CSC-IG vector. To generate fusion proteins with altered signal sequence GpLuc or $RLuc_O$ fragments were PCR amplified with forward primers including the 60 bp signal sequence of Flt3-ligand and reverse primer containing EcoV and XhoI restriction sites using pGLuc-Basic (New England Biolabs) or optimized RLuc as templates. The fragments were digested NheI/XhoI and ligated into NheI/XhoI digested pLV-CSC-IG vector resulting in LV-SGpLuc and LV-SR-$Luc_O$. LV-$SGpL_2$TR and LV-$SRL_OL_2$TR were created inserting an S-TRAIL fragment containing L2 digested with EcoV/XhoI into the LV-SGp or LV-$SRL_O$ vectors digested with EcoV/XhoI. All lentiviral constructs were packaged as lentiviral vectors in 293T/17 cells using a helper virus-free packaging system as described previously (Kock et al Neoplasia 2007). Briefly, lentiviral vectors were produced by transient transfection of 293T cells. Cells ($15 \times 10^6$) were seeded in 150 $mm^2$ tissue culture plates 24 hrs before transfection in DMEM with 10% FBS, and cells were washed with fresh medium 4 hrs before transfection. Transfection was performed by calcium phosphate precipitation method using 18 µg of transfer plasmid DNA, transfer vectors constructed above, and the lentiviral helper plasmids pCMVΔ8.91 (18 µg) and glycoprotein expression plasmid pVSVG (12 µg; Clontech). Cells were washed with fresh medium 16-18 hrs after transfection, and vector supernatants were harvested 48 hrs after transfection. The supernatants were filtered (0.45 µm) and loaded in a Beckman Quick-Seal ultracentrifuge tube (Beckman Coulter, Fullerton, Calif.) and centrifuged at 28,000×g for 90 min. Pellets were resuspended in PBS and stored at −80° C. Titers were determined by counting fluorescent transduced 293T cells.

In Example 2, the following lentiviral vectors were used: LV-GFP, LV-GFP-Fluc, LV-GFP-Rluc, LV-Fluc-DsRed2 (Shah et al. J Neurosci 2008), Pico-mCherry-Fluc, LV-Ss-Rluc (o), LV-S-TRAIL (Kock et al. Neoplasia 2007) and LV-Di-S-STRAIL. Both LV-S-TRAIL and LV-Di-S-TRAIL has an IRES-GFP (Internal ribosomal entry site-green fluorescent protein) element in the backbone. All lentiviral constructs were packaged as lentiviral vectors in 293T/17 cells using a helper virus-free packaging system. Stem cells and GBM cells were transduced with LVs at varying multiplicity of infection (MOI) by incubating virions in a culture medium containing 4 µg/ml protamine sulfate (Sigma) and cells were visualized for fluorescent protein expression by fluorescence microscopy. Following expansion in culture, both stem cells and GBM cells were sorted by fluorescence activated cell sorting or flow cytometry (FACSAria Cell-Sorting System, BD Biosciences). The effects of different concentrations of S-TRAIL on established and primary GBM cell viability were measured using an ATP-dependent luminescence reagent (CellTiterGlo, Promega).

Cell Lines and Cell Culture

U251, Gli36-EGFRvIII, Gli36-EGFRvIII-FD human glioma cells and 293T cells were grown as described previously (Shah et al. 2008, Kock et al Neoplasia 2007). Primary mouse neural stem cells (Stem Cell Technologies, Vancouver, BC. Canada s were grown as previously described (Reynolds and Weiss, Dev. Biol., 1996) in Neurocult® NSC Basal media (Stem Cell Technologies) supplemented with proliferation supplements (Stem Cell Technologies) and EGF (20 ng/mL, R&D Systems, Minneapolis, Minn.). Adherent cultures were established by culturing mNSC on tissue culture plates coated with laminin and poly-ornithine (Sigma, St. Louis, Mo.). 293T, mNSC, and glioma cells were transduced with LVs by incubating virions in a culture medium containing 4 µg/ml protamine sulfate (Sigma).

Western blot analysis, ELISA, Viability, Caspase 3/7 activation: 24 h after infection of 293T, treatment of glioma cells with media containing luciferase/S-TRAIL fusions, or non-treated mNSC and glioma cells, cells were collected in NP-40 lysis buffer and equal amounts of protein (30 µg) were denatured, separated by SDS-PAGE, transferred to nitrocellulose membrane, blocked, and incubated over night at room temperature with antibodies against TRAIL (R&D Systems, Minneapolis, Minn.), DR4 (Sigma), human caspase-8 (Cell Signaling Technologies, Danvers, Mass.), or cleaved PARP (Cell Signaling Technologies). After incubation, the blots were washed and further incubated for 1 h with peroxidase-conjugated secondary antibody (Santa Cruz Biotechnology, Santa Cruz, Calif.) in TBS-T. Blots were developed using enhanced chemiluminescence reagents (Amersham, Piscataway, N.J.). Membranes were then exposed to film for 30 s to 30 min, and quantified using NIH Image (National Institute of Health, Bethesda, Md.).

In Example 2, human glioma lines U87, LN229, A172, U251, Gli36vIII, Gli79, LN319 and U87 and primary GBM8-EF, GBM4, GBM6, GBM18 and BT74 cells were grown. Primary mouse neural stem cells were grown in NSC Basal medium (Stem Cell Technologies) supplemented with proliferation supplements (Stem Cell Technologies) and epidermal growth factor (20 ng ml-1, R&D Systems). Adherent cultures were established by culturing mNSCs on tissue culture plates coated with laminin and poly-ornithine (Sigma). Human bone marrow-derived MSCs were grown as described previously.

Human GBM cells, U87 were incubated with conditioned medium from sECM encapsulated mNSC expressing S-TRAIL or Ss-Rluc(o) for 18 hrs, lysed and centrifuged at 30,000 g for 30 min at 4° C. Equal amounts of total cell protein (30 µg) were denatured, separated by SDS-PAGE, and transferred to nitrocellulose membrane, blocked and incubated for 1 h at room temperature with rabbit polyclonal antibodies to proteins: (a) cleaved PARP and (b) caspase-8 (Cell Science, MA). Blots were developed using enhanced chemiluminescence reagents (Amersham). Membranes were then exposed to film for 30 s to 30 min.

For ELISA, eighty-percent confluent 6-well dishes of transduced 293T cells were washed with PBS and incubated in 3 mL OptiMEM (Gibco/Invitrogen, Carlsbad, Calif.) for 24 h. S-TRAIL concentration in the conditioned culture medium was measured by ELISA with the TRAIL Immunoassay Kit (Biosource International, Camarillo, Calif.) according to the manufacturer's protocol, using recombinant human TRAIL expressed in *Escherichia coli* as a standard.

To determine the effects of S-TRAIL fusion proteins on glioma cells, Gli36-EGFRvIII cells ($0.7 \times 10^6$) were incubated with conditioned media from 293T equally transduced with LV vectors encoding luciferase/S-TRAIL fusion proteins. Twenty-four hours after treatment, remaining cells were washed and resuspended in 500 µl of media. The metabolic activity of the cells was determined using a luminescent adenosine triphosphate (ATP)-based assay (CellTiter GLO; Promega, Madison, Wis.) on 25 µl of cells from the suspension according to the manufacturer's instructions. Additionally, caspase 3/7 activation was determined using the luciferase-based Caspase GLO assay (Promega) on 25 µl of cells from the suspension according to the manufacturer's instructions.

To investigate the effects of TRAIL on mNSC viability, mNSC ($0.1 \times 10^6$ cells) were treated with increasing concentrations (0-100 ng/mL) of purified S-TRAIL for 24 hours. After incubation, cells were collected in 500 µl, and cell viability was determined using 50 µl of the cell suspension as described above.

Bioluminescent Imaging of S-TRAIL Fusion Activity In Vitro

For imaging of S-TRAIL-luciferase fusion protein secretion, culture media was collected from 293T or different stem cell lines transduced with LV encoding various fusion proteins. The culture medium containing secreted fusion proteins or the cells were collected 24 h after refreshing. The luciferase activity in both cells and medium was determined by incubating the medium or cells with 1 µg/ml coelenterazine for GpLuc- and RLuc-containing fusions or 150 µg/ml D-luciferin for the FLuc-containing fusion, and imaged for 1 min using a cryogenically cooled high efficiency CCD camera system. Post processing and visualization were performed as described previously (Shah et al., Ann Neurol, 2005).

To determine the correlation between the number of transduced cells and the bioluminescence signal, cells were seeded in different concentrations and substrates for luciferases (1 µg/ml coelenterazine for RLuc and GpLuc; 1.5 µg/ml D-luciferin for FLuc) were added to the medium. Luciferase activity was measured using a luminometer at 1 sec/well. To determine the duration of transgene expression, different stem cell lines were transduced with $SRL_OL_2TR$. On days 0, 2, 7, and 14 post-transduction, cells ($1 \times 10^5$ cells) were collected, combined with coelenterazine (1 µg/ml), and luciferase activity was determined using a luminometer.

To determine relative levels of $SRL_OL_2TR$ secretion, different stem cell lines were transduced with LV-$SRL_OL_2TR$ and plated at increasing concentrations in 96 well plates. 24 hrs after transduction, equal volumes of media were collected, mixed with coelenterazine (1 µg/ml), and luciferase activity was determine using a luminometer.

For co-culture experiments different stem cell lines were transduced with appropriate MOI. 48 hrs after transduction, stem cells were plated at increasing numbers ($0-1.5 \times 10^4$) in 96 well plates. 24 hours after seeding stem cells, Gli36-EGFRvIII or U251 cells ($5 \times 10^3$) expressing mCherryFluc were overlayed on the seeded stem cell. After co-culture for 24 hours, media was transferred to a new plate, combined with coelenterazine (1 µg/ml) and imaged to visualize levels of $SRL_OL_2TR$. At the same time, 1.5 µg/ml D-luciferin for FLuc was added to the remaining glioma cells and glioma cell viability was determined by bioluminescence imaging and measuring in a luminometer.

Bioluminescent Imaging of S-TRAIL Fusion Activity In Vivo

In Example 1, to monitor the pharmacokinetics of S-TRAIL secretion in vivo, SCID mice (SCID; 3 weeks of age; Charles River Laboratories) were implanted with $4 \times 10^6$ U251-FD, U251-FD-SGpL$_2$TR, or U251-FD-SRL$_O$L$_2$TR subcutaneously in SCID mice (n=4). Mice were then serially imaged for GpLuc or RLuc activity on day 1, 3, and 15 by injecting mice with 100 µg of coelenterazine imaged photon emission determined using a cryogenically cooled high efficiency CCD camera system. To determine tumor volume, mice were injected with 2 mg D-luciferin and FLuc imaging was performed on day 2, 7, and 15. To simultaneously visualize tumor size and release of GpLuc or RLuc with modified secretion sequence, U251 glioma cells were transduced with LV encoding FlucDsRed2, followed by infection with equal MOI of either LV-SGpLuc or LV-SRLuc$_O$. $5 \times 10^6$ cells were implanted in duplicate subcutaneously in SCID mice (n=6). GpLuc and RLuc imaging were performed to visualize secretion of modified proteins on days 1, 5, and 10 as described above, followed 8 hours later by Fluc imaging to visualize tumor size as above.

In Example 1, to investigate the kinetics of tumor localization, mice were implanted with $4 \times 10^6$ Gli36-EGFRvIII-FD. Twenty-four hours later, mice were injected with 2 mg D-luciferin and FLuc imaging was performed to identify tumor location. Twenty-four hours later, mice were injected with media containing $SRL_OL_2TR$ by either intravenous infusion or direct injection around the established tumor. Five minutes post-injection, mice were injected with 100 µg of coelenterazine and imaged every 5 minutes for 40 minutes, and at 24 hours post-injection. In a separate set of mice, animals were sacrificed 1 hour post-media injection, the liver, lung, tumor kidney, urine, and blood were collected and imaged ex vivo. The tissue was weighed and data expressed relative to tissue weight. In a separate set of mice, FLuc imaging was performed 48 hours post-media injection to determine the effects of $SRL_OL_2TR$ on subcutaneous tumor growth.

In Example 2, to simultaneously visualize survival of encapsulated mNSC and release of Ss-Rluc(o), mNSC expressing GFP-Fluc and Ss-Rluc(o) were implanted in the frontal lobe of nude mice (n=6) as described above. For dual-luciferase imaging 7, 14, 21 and 28 hours after implantation, mice were injected with 100 ug of coelenterazine/mouse via tail vein and imaged for Ss-Rluc (o) activity as described previously (Shah et al. Ann Neurol 2005). Eighteen hours later, when there was no residual coelenterazine/Rluc activity, mice were injected with 1 mg D-luciferin/mouse intraperitoneally and imaged for Fluc activity after 5 minutes, as described above. Post processing and visualization were performed as described previously (Shah et al. Ann Neurol 2005) To simultaneously visualize tumor volumes and caspase-3/7 activity, mice bearing U87-mCherry-Fluc tumors were resected and implanted with encapsulated mNSC-TRAIL or mNSC-GFP-Rluc in the resection cavity. Tumor volumes were followed by imaging mice for Fluc activity as described above. For imaging apoptosis induced by S-TRAIL expression, mice were given an intraperitoneal (i.p.) injection of highly purified Caspase-Glo 3/7 reagent (Promega, Madison, Wis.; 5 mg in 150 µL DMSO) and imaged for caspase-3 dependent luciferase activity for 5 minute after administration of Caspase-Glo 3/7 reagent. Post processing and visualization were performed as described previously (Shah et al. Ann Neurol 2005).

Immunocytochemistry and Immunohistochemistry

To assess the differentiation potential of cultured mNSC, cells were plated on laminin/polyornithine coated coverslips and incubated in Neurocult media containing differentiation supplements (Stem Cell Technologies) for 10 days. Following differentiation, cells were washed 2× with PBS and fixed with 4% paraformaldehyde for 20 minutes. The cells were then permeabilized and incubated with anti-Nestin (Millipore, Billireca, Mass.), anti-GFAP (Chemicon), and anti-Olig2 (Chemicon) antibodies for 1 hour at 37° C. The cells were washed and incubated with Alexa dye 555 nm (Invitrogen) for 1 hour, washed, mounted, and examined microscopically.

To investigate the differentiation potential of $SRL_OL_2TR$-secreting mNSC, a separate cohort of mice were implanted with a mix of mNSC expressing $SRL_OL_2TR$ and unlabelled Gli36-EGFFvIII glioma cells. On day 4 post-implantation, mice were perfused, brains were removed, and 30 µM sections of the brains were generated using a vibratome. Floating brain sections were immunostained with antibodies against mouse nestin, GFAP, Tuj-1 (Covance, Princeton, N.J.), and Ki67 (DAKO, Carpinteria, Calif.), followed by incubation with Alexa dye 555 nm secondary antibodies, mounting, and visualization by confocal microscopy.

To investigate the migration of transduced mNSCs towards gliomas, Gli36-EGFRvIII-FD were stereotactically implanted into the frontal lobe of mice. On day 3 post-implantation, transduced mNSC expressing GFP-RLuc were implanted 1 mm lateral to the gliomas. Mice were sacrificed 2, 5, and 10 days after mNSC implantation. The brains were collected, sectioned, mounted, and cells expressing fluorescent markers were visualized using confocal microscopy.

Tissue Processing

Mice bearing tumors in the cranial window or mice with resected tumors or mice with resected tumors and implanted with sECM encapsulated mNSC were perfused with formalin and brains were removed and sectioned. The tissue sections were dehydrated in xylene and ethanol, immersed in PBS and stained with hematoxylin and Eosin (H&E). Photomicrographs of both IHC and H&E slides were taken using the Nikon E400 light microscope (Nikon Instruments Inc, Melville, N.Y.) attached to a SPOT CCD digital camera (Diagnostics Instruments, Inc., Sterling Heights, Mich.)

sECM Encapsulated mNSC: Cell Viability, ELISA and Release of Secreted Proteins:

The sECM components, Hystem and Extralink (Glycosan Biosystems, Salt Lake City, Utah) were reconstituted according to the protocol provided by Glycosan Biosystems. Specifically, 1, 2 or $4 \times 10^5$ mNSC expressing either a) GFP-Fluc and Ss-Rluc (o) or b) S-TRAIL were resuspended in Hystem (11 µl) and Extralink (9 µl) was added to cross-link the matrix as described in the protocol. After 20 minutes (gelation time) at room temperature (25 C), the mNSC-sECM hydrogel was placed in the center of different sizes (35 or 60 mm) of glass-bottom dishes.

To determine the correlation between the number of U87-Fluc-mCherry or sECM encapsulated mNSC expressing GFP-Fluc and Ss-Rluc(o) and bioluminescence signal, different numbers of mNSC were encapsulated in sECMs and U87-mCherry-Fluc cells were seeded in different concentrations and D-luciferin (1.5 ug/ml) was added to the medium and luciferase activity was measured using a cryogenically cooled high efficiency CCD camera system (Roper Scientific, Trenton, N.J., USA). Each experiment was performed in triplicate. To simultaneously assess mNSC viability and release of mNSC-secreted proteins out of sECM, mNSC expressing GFP-Fluc and Ss-Rluc(o) were encapsulated into sECM and followed by Fluc and Rluc bioluminescence imaging in vitro as described herein over a period of 12 days. To assess TRAIL concentration, the conditioned medium from sECM-mNSC expressing Ss-Rluc(o) or S-TRAIL was collected and ELISA was performed as described previously (Kock et al. Neoplasia 2007).

Statistical Analysis

Data were analyzed by Student t test when comparing 2 groups and by ANOVA, followed by Dunnetts post-test when comparing greater than 2 groups. Data were expressed as mean±SEM and differences were considered significant at $P<0.05$. Survival times of mice groups were compared using logrank test.

Intracranial mNSC Survival and Tumor Progression

To assess the survival of transduced mNSC in the brain, $1\times10^6$ mNSC transduced with LV-GFP-FLuc were mixed with Gli36-EGFRvIII ($0.1\times10^6$) and stereotactically implanted (from bregma, ML: 2.5 mm, SI: 2 mm) (n=4 in each case) in mice as described previously (Shah et al. 2008). FLuc imaging was performed 2, 6, 9, and 12 days post-injection by giving mice intraperitoneal injection of 2 mg of D-luciferin and collecting photon emission over 5 minutes with a cooled charge-coupled device camera. Images were processed as described previously (Shah et al. 2008). To determine the effects of SRLOL2TR on intracranial gliomas, Gli36-EGFRvIII-FD and mNSC expressing SRLOL2TR were harvested at 80% confluency and a mix of glioma cells ($5\times10^5$) and transduced mNSC ($1\times10^6$) (n=4 in each case) was implanted stereotactically (from bregma, ML: 2.5 mm, SI: 2 mm) (n=4 in each case). Mice were injected intraperitoneally with 4.5 mg/mouse of D-luciferin on days 1, 3, 6, 9, 13, and 21 and imaged as described above. To monitor SRLOL2TR from mNSC, the same mice were imaged for RLucO activity on days 2, 6, 9, and 12 by injecting 100 µg of coelenterazine intravenously, and 5 minutes later photon emission was determined over 7 minutes. All images were processed as described previously (Shah et al. 2008).

Creation of a Mouse Model of Resection

Athymic nude mice (6-8 weeks of age; Charles River Laboratories, Wilmington, Mass.) 25-30 g in weight (n=8 in each group) were used for the intracranial xenograft GBM model. One week prior to GBM cell implantation, mice were immobilized on a stereotactic frame and a small circular portion of the skull (~7 mm diameter) was removed, and the dura was gently peeled back from the cortical surface. U87 expressing Fluc-mCherry were harvested at 80% confluency and implanted stereotactically ($7.5\times10^4$ or $1.5\times10^5$ (n=16 in each case) in the right frontal lobe and the skin was sutured together. On the day of tumor resection (day 14: for mice implanted with $7.5\times10^4$ tumor cells; and day 21: for mice implanted with $1.5\times10^5$ cells post tumor cell implantation; n=16 in each group), mice were imaged by Fluc bioluminescence imaging (n=16 from each group) and intravital microscopy (n=3 in each group) as described previously (Shah et al. J Neurosci 2008, Arwent et al. Cancer Res 2007). For intravital microscopy, angiosense-750 (Visen Medical) was injected and mice were imaged to visualize tumor volumes and associated vasculature as described previously (Van Eekelen et al. Oncogene 2010). For tumor resection, mice (n=8 from each group) were immobilized on a stereotactic frame, the skin was opened and the superficial tumor was exposed. A dissecting Leica surgical microscope with 20× magnification was used for mechanical resection to reduce the tumor volume up to the tumor-tissue interface, leaving margins of the dura intact. Finally, the wound was copiously irrigated and the skin closed with 4-0 Vicryl suture. Mice were imaged by bioluminescence imaging and intravital microscopy post-resection. Ex-vivo analysis on resected tumors was performed by incubating tumors with 1.5 µg/ml D-luciferin in PBS and by bioluminescence imaging. The studies described herein used 140 female mice.

In Vitro Imaging of S-TRAIL Secretion, Tumor Cell Viability and Caspase3/7 Activity In Example 2, mNSCs expressing Ss-Rluc(o) or S-TRAIL ($1\times10^5$) were encapsulated in sECM and placed in a 35 mm plate as described above. Human GBM cells, U87-mCherry-Fluc ($2\times10^5$) were plated around the sECM-NSC and cell viability at different time points (8-24 hours) was measured by quantitative in vitro bioluminescence imaging as described herein. GBM cells were also assessed at different time points (8-24 hours) for caspase-3/7 activity with a caged, caspase 3/7-activatable DEVD-aminoluciferin (Caspase-Glo 3/7, Promega, Madison, Wis., USA) as described previously (Shah et al. Ann Neurol 2005). For co-culture experiments, increasing numbers ($0-4\times10^5$) of mNSC expressing Di-S-TRAIL were encapsulated in sECM, plated and 24 hrs later, U87-mCherry-Fluc ($1\times10^5$) were seeded around the sECM encapsulated mNSC. After co-culture for 24 hrs, media was transferred to a new plate, combined with coelenterazine (1 µg/ml) and imaged to visualize levels of Di-S-TRAIL. At the same time, 1.5 µg/ml D-luciferin for FLuc was added to the remaining GBM cells and GBM cell viability was determined by bioluminescence imaging and measuring in a luminometer. Similarly, hMSCs expressing GFP or S-TRAIL ($1\times10^5$) were encapsulated in sECM and placed in a 35-mm plate, GBM8-mCherry-Fluc cells ($2\times10^5$) were plated around the sECM-encapsulated hMSCs, and cell viability and caspase3/7 activity were measured by quantitative in vitro bioluminescence imaging at different time points (15-24 h) as described herein above.

sECM-mNSC Survival and Migration Studies:

In Example 2, to compare sECM encapsulated and non-encapsulated mNSC survival in athymic nude mice, GFP-Fluc expressing mNSC ($5\times10^5$/mouse) were either resuspended in PBS or encapsulated in sECMs and implanted stereotaxically (n=5 in each case) in the right frontal lobe (from bregma, AP: −2 mm, ML: 2 mm V (from dura): 2 mm) and mice were imaged on weeks 1-4 for Fluc activity as described below. To compare sECM encapsulated and non-encapsulated mNSC survival in the tumor resection cavity, mice implanted with U87-Rluc-DsRed2 tumors in the cranial window were imaged for Rluc activity by injecting 100 ug of coelenterazine/mouse via tail vein (described in detail herein), resected and implanted with GFP-Fluc expressing mNSC ($5\times10^5$/mouse) either resuspended in PBS or encapsulated in sECM (n=5 in each case). To encapsulate mNSC expressing GFP-Fluc, mNSC were resuspended with the two different components of sECM as described above and 10 min later, the mNSC-sECM encapsulated mix was placed in the resection cavity immediately after tumor resection and the skin was closed with 4-0 Vicryl suture. Mice were imaged on week 1-4 for Fluc activity as described below and intravital microscopy as described above. To study the migration of sECM encapsulated mNSC toward GBMs, U87-mCherry-Fluc cells ($5\times10^4$) were implanted stereotaxically into the right frontal lobe in cranial windows of nude mice (n=10) and 7 days later, encapsulated mNSC-GFP-Fluc (n=5) or saline (n=4) were injected into the right frontal lobe of tumor-bearing mice. mNSC migration was followed by intravital microscopy as described earlier (Shah et al. J Neurosci 2008).

To study the effect of therapeutic mNSC-S-TRAIL encapsulated in sECM in the resection model, mice (n=32) bearing U87-mCherry-Fluc GBMs in the cranial window were imaged for Fluc activity on the day of resection (Day 21 post tumor cell implantation), divided into 4 groups (n=8 in each group) by distributing mice of matching tumor sizes (indicated by the Fluc signal intensity) equally across all groups, and resected (n=24) as described above. Mice were immediately imaged for Fluc signal intensity post-resection. sECM encapsulated mNSC-S-TRAIL (n=8), mNSC-GFP-Rluc (n=8) or non-encapsulated mNSC-S-TRAIL (n=8) were placed in the tumor resection cavity and mice were followed for survival over time (including un-resected controls, n=8). Tumor volumes in the mNSC-S-TRAIL and mNSC-GFP-Rluc group were imaged by Fluc bioluminescence imaging as described earlier (Sasportas et al. Proc Natl Acad Sci 2009). To study the effects of therapeutic hMSC-S-TRAIL cells encapsulated in sECM in the primary invasive GBM8 resection model, mice (n=14) bearing GBM8-mCherry-Fluc tumors in the cranial window were imaged for Fluc activity on the day of resection (day 7 after tumor cell implantation) and divided into two groups (n=7 in each group) as described above. sECM-encapsulated hMSC-S-TRAIL (n=7) or hMSC-GFP (n=7) cells were placed in the tumor resection cavity and tumor volumes were imaged by Fluc bioluminescence imaging.

Western Blot Analysis.

In Example 2, human U87 GBM cells were incubated with conditioned medium from sECM-encapsulated mNSCs expressing S-TRAIL or Ss-Rluc(o) for 18 h, lysed and centrifuged at 30,000 g for 30 min at 4° C. Equal amounts of total cellular protein (30 µg) were denatured, separated by SDS-PAGE, transferred to nitrocellulose membrane, blocked and incubated for 1 h at 25° C. with rabbit polyclonal antibodies to cleaved PARP and caspase-8 (Cell Science). Blots were developed using enhanced chemiluminescence reagents (Amersham). Membranes were then exposed to film for 30 s to 30 min.

Collagen Invasion Assay

In Example 2, human GBM8-Fluc-mCherry cells created from the GBM8-EF line were grown as spheres and resuspended in rat tail collagen, type 1 (BD Biosciences). The solution was then allowed to solidify in a culture dish and the cells were supplemented with the growth medium. Collagen-embedded GBM8-Fluc-mCherry cells were imaged at days 0 and 5 to visualize dispersal of GBM8-Fluc-mCherry cells into the collagen matrix from the primary sphere.

Dual Bioluminescence Imaging In Vivo.

In Example 2, to simultaneously visualize survival of encapsulated mNSCs and release of Ss-Rluc(o), mNSCs expressing GFP-Fluc and Ss-Rluc(o) were implanted in the frontal lobe of nude mice (n=6) as described herein above. For dual luciferase imaging 7, 14, 21 and 28 d after implantation, mice were injected with 100 µg of coelenterazine per mouse through the tail vein and imaged for Ss-Rluc (o) activity. Eighteen hours later, when there was no residual coelenterazine-Rluc activity, mice were injected with 1 mg d-luciferin per mouse intraperitoneally and imaged for Fluc activity 5 min later as described herein above. Postprocessing and visualization were performed. To simultaneously visualize tumor volumes and caspase-3/7 activity, mice bearing U87-mCherry-Fluc tumors were resected and implanted with encapsulated mNSC-TRAIL or mNSC-GFP-Rluc cells in the resection cavity. Tumor volumes were followed by imaging mice for Fluc activity as described herein above. For imaging apoptosis induced by S-TRAIL expression, mice were injected intraperitoneally with highly purified Caspase-Glo 3/7 reagent (5 mg in 150 µl DMSO) and imaged for caspase-3-dependent luciferase activity for 5 min after administration of the Caspase-Glo 3/7 reagent. Postprocessing and visualization were performed. All images are the visible light image superimposed with bioluminescence images with a scale in photons $min^{-1}$ $cm^{-2}$.

Tissue Processing

Mice bearing tumors in the cranial window or mice with resected tumors or mice with resected tumors and implanted with sECMencapsulated mNSCs or hMSCs were perfused with formalin and brains were removed and sectioned. Cleaved caspase-3 immunohistochemical staining on brain sections was performed. Photomicrographs of immunohistochemistry and hematoxylin and eosin slides were taken using a Nikon E400 light microscope attached to a SPOT CCD digital camera (Diagnostics Instruments).

Statistical Analysis.

Data were analyzed by Student t-test when comparing two groups and by ANOVA, followed by Dunnett's post-test, when comparing more than two groups. Data are expressed as mean±s.e.m., and differences were considered significant at $P<0.05$. Survival times of groups of mice were compared using a log-rank test.

TABLE 1

Composition and acitivity of luciferase and S-TRAIL fusion proteins: − (no activity); ++++ (highest activity)

| Construct Name | Fusion | Diagnostic Extra-cellular In Vitro Activity | Therapeutic In Vivo Activity | In Vitro Activity | In Vivo Activity |
|---|---|---|---|---|---|
| TRRL | S-TRAIL-RLuc | − | N/A | − | N/A |
| TRFL | S-TRAIL-FLuc | − | N/A | − | N/A |
| TRGp | S-TRAIL-GpLuc | ++ | N/A | − | N/A |
| GpTR | GpLuc-S-TRAIL | + | N/A | + | N/A |
| $GpL_1TR$ | GpLuc-L1-S-TRAIL | ++ | N/A | + | N/A |
| $GpL_2TR$ | GpLuc-L2-S-TRAIL | +++ | N/A | +++ | N/A |
| $SGpL_2TR$ | S-GpLuc-L2-S-TRAIL | ++++ | + | ++++ | ++++ |
| $SRL_oL_2TR$ | S-$RLuc_o$-L2-S-TRAIL | +++ | ++++ | +++ | ++++ |

REFERENCES

Akbar, U. et al. Delivery of temozolomide to the tumor bed via biodegradable gel matrices in a novel model of intracranial glioma with resection. *J Neurooncol* 94, 203-12 (2009).

Arwert, E. et al. Visualizing the dynamics of EGFR activity and antiglioma therapies in vivo. *Cancer Res* 67, 7335-42 (2007).

Ashkenazi A, Holland P, Eckhardt S G. Ligand-based targeting of apoptosis in cancer: The potential of recombinant human apoptosis ligand 2/Tumor necrosis factor-related apoptosis-inducing ligand (rhApo2L/TRAIL). J Clin Oncol 2008; 26: 3621-3630.

Baci-Onder, T., Wakimoto, H., Cameron, C. and Shah, K. Evaluating the efficacy of a dual PI3K/mTOR inhibitor and stem cell delivered TRAIL in mouse models of glioma. *Cancer Research* (2010 in press).

Bidros, D. S. & Vogelbaum, M. A. Novel drug delivery strategies in neuro-oncology. *Neurotherapeutics* 6, 539-46 (2009).

Bremer E, Samplonius D, Kroesen B J et al. Exceptionally potent anti-tumor bystander activity of an scFv:sTRAIL fusion protein with specificity for EGP2 toward target antigen-negative tumor cells. Neoplasia 2004; 6: 636-645.

Corsten M F, Shah K. Therapeutic stem-cells for cancer treatment: Hopes and hurdles in tactical warfare. Lancet Oncology 2008; 9: 376-384.

de Oliveira, M. S. et al. Anti-proliferative effect of the gastrin-release peptide receptor antagonist RC-3095 plus temozolomide in experimental glioblastoma models. *J Neurooncol* 93, 191-201 (2009).

Ehtesham, M. et al. Induction of glioblastoma apoptosis using neural stem cell-mediated delivery of tumor necrosis factor-related apoptosis-inducing ligand. *Cancer Res* 62, 7170-4 (2002).

Hingtgen S, Ren X, Terwilliger E et al. Targeting multiple pathways in gliomas with stem cell and viral delivered S-TRAIL and Temozolomide. Mol Cancer Ther 2008; 7: 3575-3585.

Kelley S K, Harris L A, Xie D et al. Preclinical studies to predict the disposition of Apo2L/tumor necrosis factor-related apoptosis-inducing ligand in humans: Characterization of in vivo efficacy, pharmacokinetics, and safety. J Pharmacol Exp Ther 2001; 299: 31-38.

Kock N, Kasmieh R, Weissleder R, Shah K. Tumor therapy mediated by lentiviral expression of shBcl-2 and S-TRAIL. Neoplasia. 2007; 9:435-442

Jurvansuu, J. et al. Transmembrane protein 18 enhances the tropism of neural stem cells for glioma cells. *Cancer Res* 68, 4614-22 (2008).

Laflamme, M. A. et al. Cardiomyocytes derived from human embryonic stem cells in pro-survival factors enhance function of infarcted rat hearts. *Nat Biotechnol* 25, 1015-24 (2007).

Lin J H. Applications and limitations of interspecies scaling and in vitro extrapolation in pharmacokinetics. Drug Metab Dispos 1998; 26: 1202-1212.

Minniti, G. et al. Radiotherapy plus concomitant and adjuvant temozolomide for glioblastoma in elderly patients. *J Neurooncol* 88, 97-103 (2008).

Mooney, D. J. & Vandenburgh, H. Cell delivery mechanisms for tissue repair. *Cell Stem Cell* 2, 205-13 (2008).

Orive, G., Anitua, E., Pedraz, J. L. & Emerich, D. F. Biomaterials for promoting brain protection, repair and regeneration. *Nat Rev Neurosci* 10, 682-92 (2009).

Pan, L., Ren, Y., Cui, F. & Xu, Q. Viability and differentiation of neural precursors on hyaluronic acid hydrogel scaffold. *J Neurosci Res* 87, 3207-20 (2009).

Pandita, A., Aldape, K. D., Zadeh, G., Guha, A. & James, C. D. Contrasting in vivo and in vitro fates of glioblastoma cell subpopulations with amplified EGFR. *Genes Chromosomes Cancer* 39, 29-36 (2004).

Piccirillo, S. G., Binda, E., Fiocco, R., Vescovi, A. L. & Shah, K. Brain cancer stem cells. *J Mol Med* 87, 1087-95 (2009).

Ray P, Wu A M, Gambhir S S. Optical bioluminescence and positron emission tomography imaging of a novel fusion reporter gene in tumor xenografts of living mice. Cancer Res 2003; 63: 1160-1165.

Reynolds B A, Weiss S. Clonal and population analyses demonstrate that an EGF-responsive mammalian embryonic CNS precursor is a stem cell. Dev Biol. 1996; 175:1-13.

Sasportas L S, Kasmieh R, Wakimoto H et al. Assessment of therapeutic efficacy and fate of engineered human mesenchymal stem cells for cancer therapy. Proc Natl Acad Sci USA 2009; 106: 4822-4827.

Sena-Esteves M, Tebbets J C, Steffens S, Crombleholme T, Flake A W. Optimized large-scale production of high titer lentivirus vector pseudotypes. J Virol Methods. 2004; 122:131-139

Shah, K., Tang, Y., Breakefield, X. & Weissleder, R. Real-time imaging of TRAIL-induced apoptosis of glioma tumors in vivo. *Oncogene* 22, 6865-72 (2003).

Shah K, Tung C H, Yang K, Weissleder R, Breakefield X O. Inducible release of TRAIL fusion proteins from a proapoptotic form for tumor therapy. Cancer Res. 2004; 64:3236-3242.

Shah K, Bureau E, Kim D E, et al. Glioma therapy and real-time imaging of neural precursor cell migration and tumor regression. Ann Neurol. 2005; 57:34-41

Shah K, Hingtgen S, Kasmieh R, et al. Bimodal viral vectors and in vivo imaging reveal the fate of human neural stem cells in experimental glioma model. J Neurosci. 2008; 28:4406-4413.

Shen J, Wu Y, Shi L et al. Construction and characterization of two versions of bifunctional EGFP-sTRAIL fusion proteins. Appl Microbiol Biotechnol 2007; 76: 141-149.

Singec I, Jandial R, Crain A et al. The leading edge of stem cell therapeutics. Annu Rev Med 2007; 58: 313-328.

Terrovitis, J. et al. Ectopic expression of the sodium-iodide symporter enables imaging of transplanted cardiac stem cells in vivo by single-photon emission computed tomography or positron emission tomography. *J Am Coll Cardiol* 52, 1652-60 (2008).

van Eekelen, M. et al. Human stem cells expressing novel TSP-1 variant have anti-angiogenic effect on brain tumors. *Oncogene* (2010).

Venisnik K M, Olafsen T, Loening A M et al. Bifunctional antibody-*Renilla* luciferase fusion protein for in vivo optical detection of tumors. Protein Eng Des Sel 2006; 19: 453-460.

Venisnik K, Olafsen T, Gambhir S et al. Fusion of *Gaussia* luciferase to an engineered anti-carcinoembryonic antigen (CEA) antibody for in vivo optical imaging. Mol Imaging Biol 2007; 9: 267-277.

Wakimoto, H. et al. Human glioblastoma-derived cancer stem cells: establishment of invasive glioma models and treatment with oncolytic herpes simplex virus vectors. *Cancer Res* 69, 3472-81 (2009).

Wen, P. Y. & Kesari, S. Malignant gliomas in adults. *N Engl J Med* 359, 492-507 (2008).

Wiley S R, Schooley K, Smolak P J et al. Identification and characterization of a new member of the TNF family that induces apoptosis. Immunity 1995; 3: 673-682.

Xu, X., Yang, G., Zhang, H. & Prestwich, G. D. Evaluating dual activity LPA receptor pan-antagonist/autotaxin inhibitors as anti-cancer agents in vivo using engineered human tumors. *Prostaglandins Other Lipid Mediat* 89, 140-6 (2009)

Zvibel, I., Smets, F. & Soriano, H. Anoikis: roadblock to cell transplantation? *Cell Transplant* 11, 621-30 (2002).

I claim:

1. A method of treatment and bioluminescent visualization for a subject having a malignant condition comprising administering a therapeutically effective amount of a pharmaceutical composition comprising a soluble TRAIL fusion protein comprising, in the following N-terminal to C-terminal order, a reporter module, a linker module of at least 8 amino acids, and a therapeutic TRAIL module, wherein said therapeutic TRAIL module comprises an extracellular domain of human TRAIL of SEQ ID NO: 1, and a pharmaceutically acceptable carrier.

2. The method of claim 1, wherein the malignant condition is a glioblastoma.

3. The method of claim 1, further comprising administering to the subject, one or more additional chemotherapeutic agents, biologics, drugs, or treatments as part of a combinatorial therapy.

4. The method of claim 3, wherein the chemotherapeutic agent, biologic, drug, or treatment is selected from the group consisting of: radiation therapy, tumor resection surgery, gemcitabine, cisplastin, paclitaxel, carboplatin, bortezomib, AMG479, vorinostat, rituximab, temozolomide, rapamycin, ABT-737, and PI-103.

5. The method of claim 1, wherein the pharmaceutical composition is administered at a surgical site.

6. The method of claim 5, wherein the surgical site is a tumor resection site.

7. The method of claim 1, wherein the linker domain comprises the amino acid sequence of SEQ ID NO: 4.

8. The method of claim 1, wherein the therapeutic TRAIL module comprises amino acids 39-281 of SEQ ID NO: 1.

9. The method of claim 1, wherein the therapeutic TRAIL module comprises amino acids 95-281 of SEQ ID NO: 1.

10. The method of claim 1, wherein the therapeutic TRAIL module comprises amino acids 114-281 of SEQ ID NO: 1.

11. The method of claim 1, wherein the therapeutic TRAIL module consists of amino acids 114-281 of SEQ ID NO: 1.

12. The method of claim 1, wherein the soluble TRAIL fusion protein is encoded by a human stem cell comprising a nucleic acid sequence encoding the soluble TRAIL agent.

13. The method of claim 12, wherein the human stem cell is encapsulated in a matrix or scaffold.

* * * * *